US011185411B2

(12) United States Patent
Gregg et al.

(10) Patent No.: US 11,185,411 B2
(45) Date of Patent: Nov. 30, 2021

(54) CARDIAC VALVE DELIVERY DEVICES AND SYSTEMS

(71) Applicant: Cephea Valve Technologies, Inc., San Jose, CA (US)

(72) Inventors: Peter Gregg, Santa Cruz, CA (US); Dan Wallace, Santa Cruz, CA (US); Evelyn Haynes, Santa Cruz, CA (US); Aaron Grogan, Scotts Valley, CA (US); Crissly Crisostomo, San Jose, CA (US); Max Pfeifle, San Jose, CA (US)

(73) Assignee: Cephea Valve Technologies, Inc., Santa Clara, CA (US)

( * ) Notice: Subject to any disclaimer, the term of this patent is extended or adjusted under 35 U.S.C. 154(b) by 176 days.

(21) Appl. No.: 16/461,216

(22) PCT Filed: Nov. 16, 2017

(86) PCT No.: PCT/US2017/062045
§ 371 (c)(1),
(2) Date: May 15, 2019

(87) PCT Pub. No.: WO2018/094069
PCT Pub. Date: May 24, 2018

(65) Prior Publication Data
US 2019/0374342 A1      Dec. 12, 2019

Related U.S. Application Data

(60) Provisional application No. 62/424,051, filed on Nov. 18, 2016.

(51) Int. Cl.
*A61F 2/24* (2006.01)
*A61F 2/966* (2013.01)
*A61F 2/95* (2013.01)

(52) U.S. Cl.
CPC .......... *A61F 2/2436* (2013.01); *A61F 2/9661* (2020.05); *A61F 2/9517* (2020.05); *A61F 2002/9665* (2013.01)

(58) Field of Classification Search
CPC ...... A61F 2/2436; A61F 2/966; A61F 2/9517; A61F 2002/9665; A61F 2002/9511; A61F 2/2439; A61F 2/9661
See application file for complete search history.

(56) References Cited

U.S. PATENT DOCUMENTS

| 5,554,183 A | 9/1996 | Nazari |
| 8,970,948 B2 | 3/2015 | Connolly et al. |

(Continued)

FOREIGN PATENT DOCUMENTS

| CN | 105188612 A | 12/2015 |
| CN | 105744915 A | 7/2016 |

(Continued)

OTHER PUBLICATIONS

International Search Report for PCT/US2017/062045 dated Mar. 26, 2018.

(Continued)

*Primary Examiner* — Richard G Louis
(74) *Attorney, Agent, or Firm* — Lerner, David, Littenberg, Krumholz & Mentlik, LLP

(57) ABSTRACT

A delivery device includes a handle, a central elongate member extending from the handle, a sheath configured to slide over and relative to the central elongate member, a distal tether retainer at a distal end of the central elongate member, a proximal tether restraining mechanism positioned along the central elongate member distal of the handle and proximal of the distal tether retainer, and a (Continued)

plurality of tethers. The tethers are configured to extend from the proximal tether restraining mechanism to the distal tether retainer.

13 Claims, 87 Drawing Sheets

(56) References Cited

U.S. PATENT DOCUMENTS

| | | | |
|---|---|---|---|
| 2006/0265045 A1 | 11/2006 | Shiu et al. | |
| 2007/0203575 A1* | 8/2007 | Forster | A61F 2/2439 623/2.11 |
| 2008/0071343 A1* | 3/2008 | Mayberry | A61F 2/954 623/1.11 |
| 2008/0234797 A1 | 9/2008 | Styrc | |
| 2010/0094314 A1 | 4/2010 | Hernlund et al. | |
| 2014/0330368 A1 | 11/2014 | Gloss et al. | |
| 2014/0343670 A1 | 11/2014 | Bakis et al. | |
| 2015/0142101 A1 | 5/2015 | Coleman et al. | |
| 2016/0158000 A1 | 6/2016 | Granada et al. | |
| 2016/0250051 A1 | 9/2016 | Lim et al. | |

FOREIGN PATENT DOCUMENTS

| | | |
|---|---|---|
| JP | 2016518948 A | 6/2016 |
| WO | 2016168609 A1 | 10/2016 |
| WO | 2016183523 A1 | 11/2016 |
| WO | 2016183526 A1 | 11/2016 |
| WO | 2017218877 A1 | 12/2017 |

OTHER PUBLICATIONS

Australian Search Report for Application No. 2017363069, dated Aug. 13, 2019, 1 pg.
Extended European Search Report including Written Opinion for EP17870871.5 dated May 26, 2020; 9 pages.
Search Report from Chinese Office for Application N. 2017800838453 dated Sep. 28, 2020; 2 pages.
Search Report from Chinese Office for Application No. 2017800838453 dated Mar. 26, 2021; 2 pages.

* cited by examiner

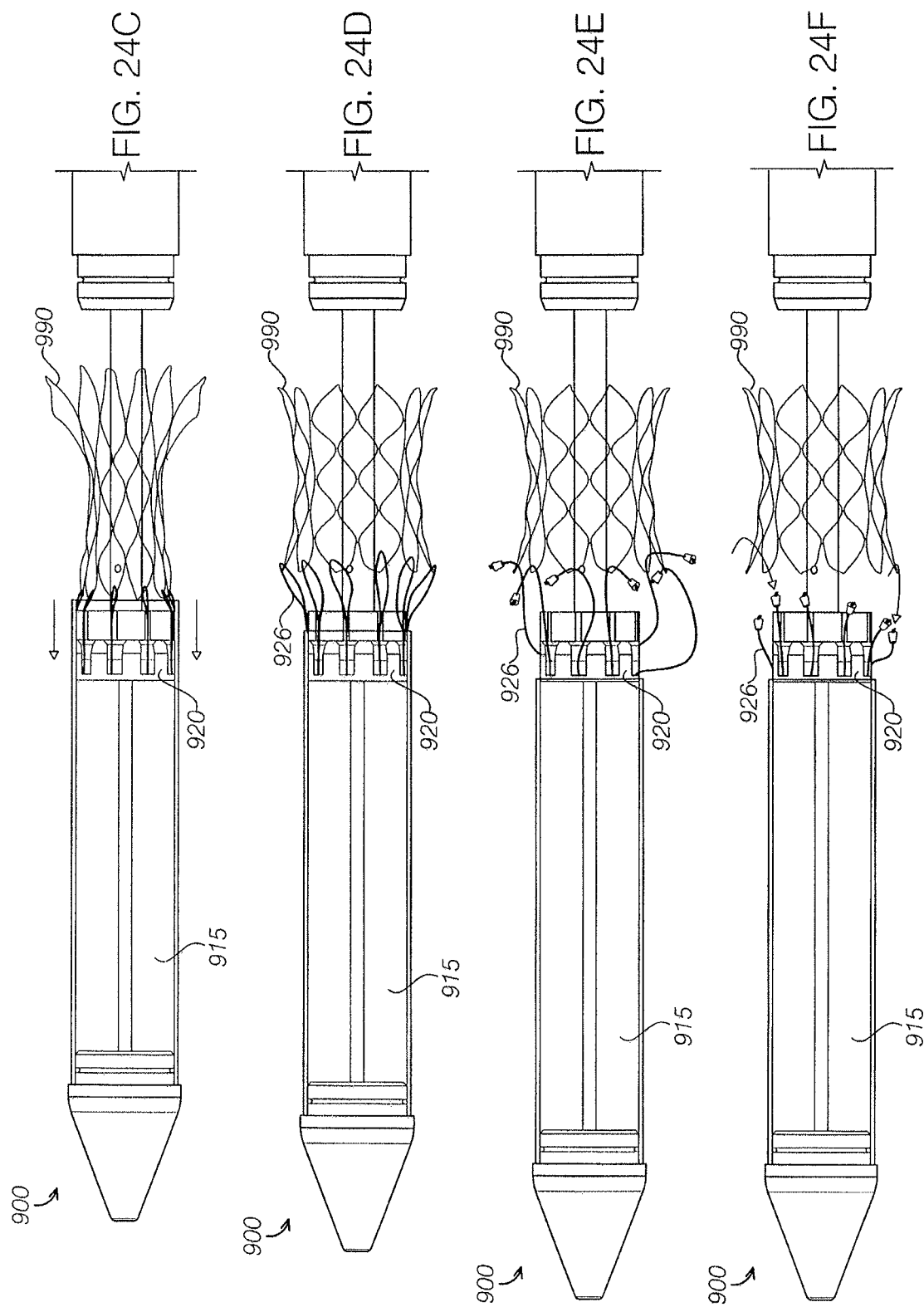

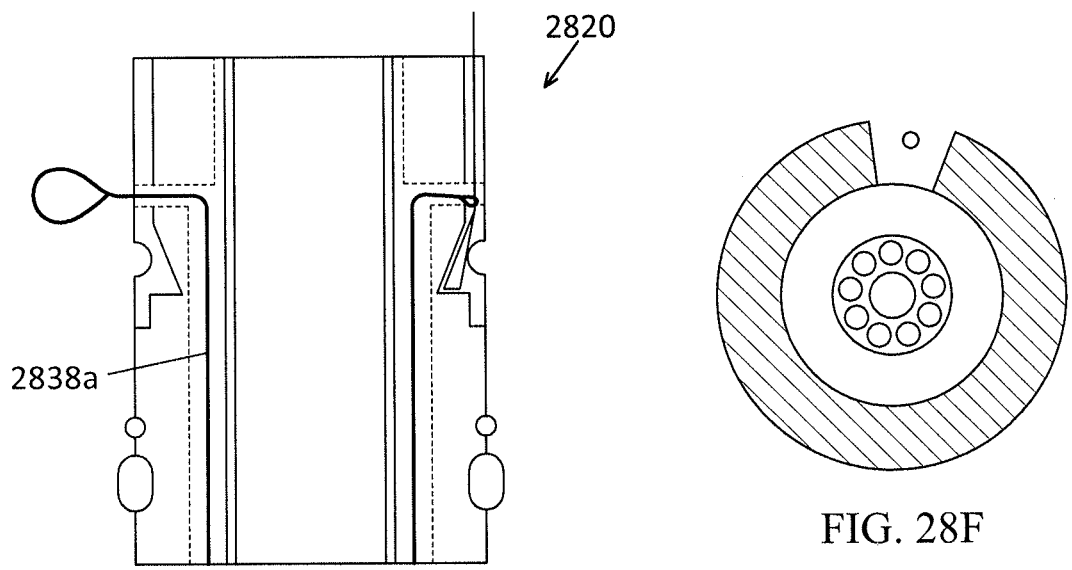
FIG. 28D
FIG. 28F
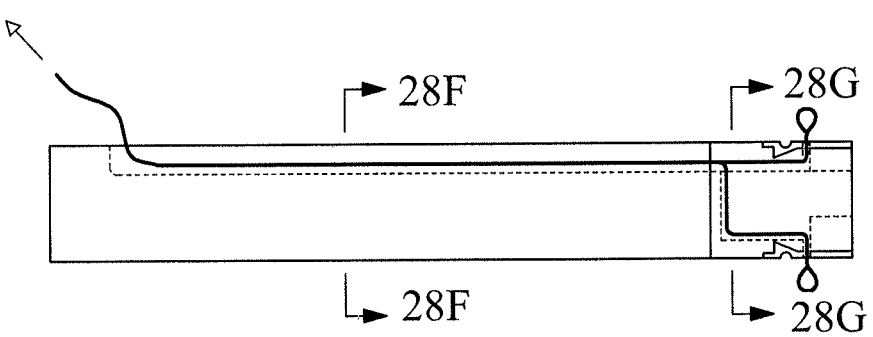
FIG. 28E
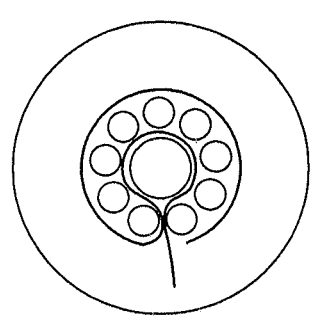
FIG. 28H
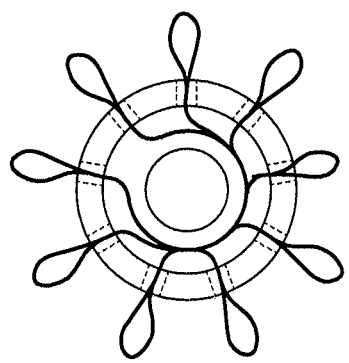
FIG. 28G

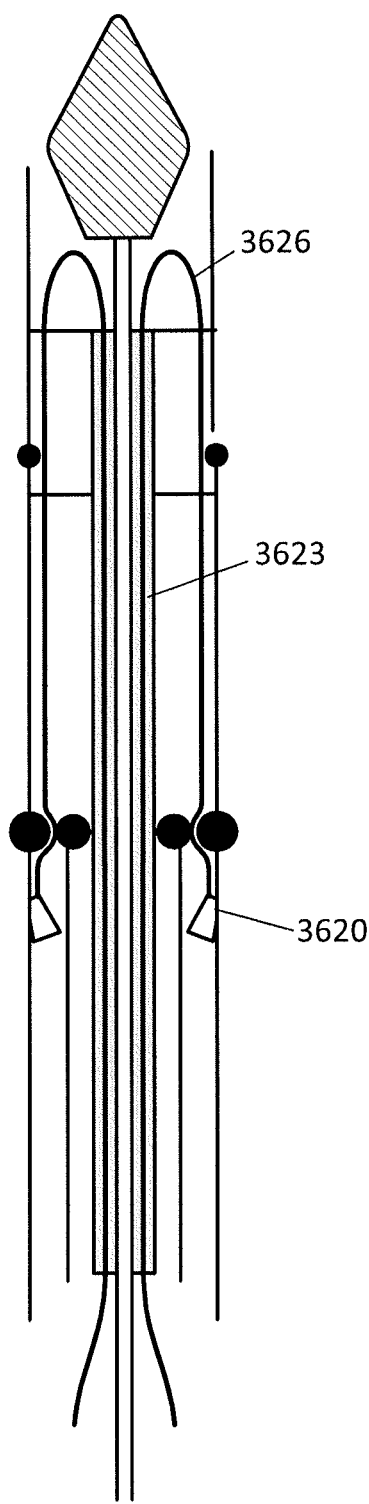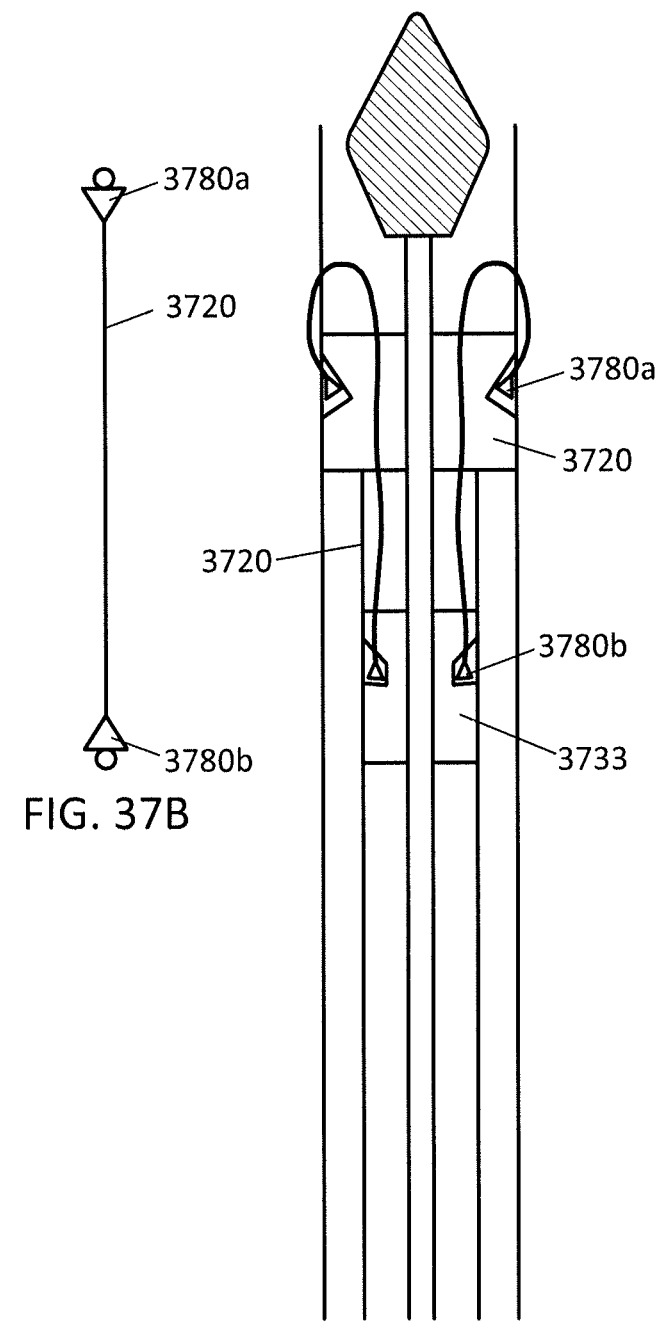
FIG. 36
FIG. 37B
FIG. 37A

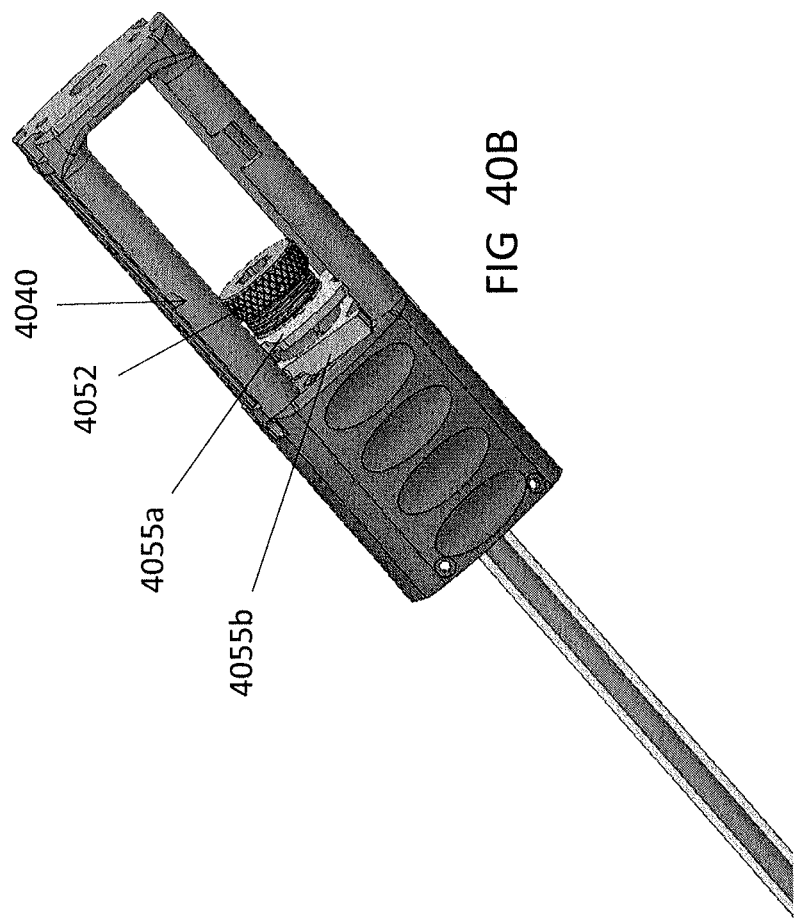

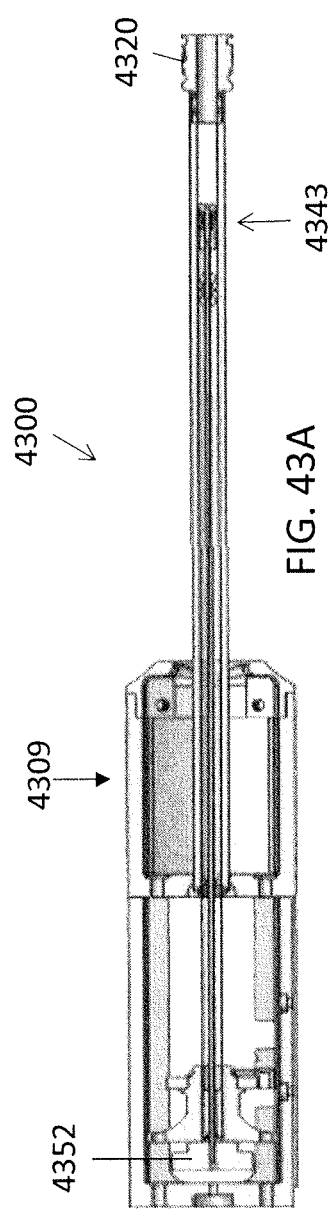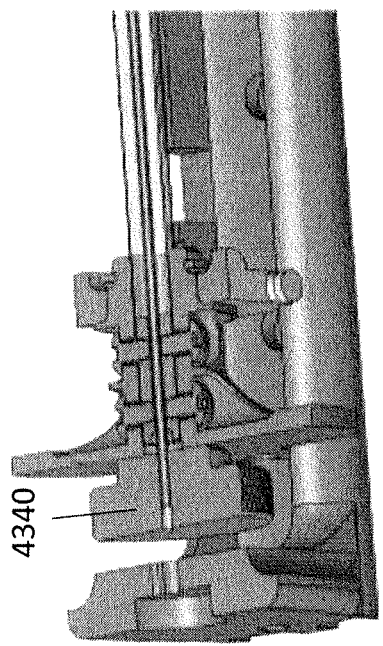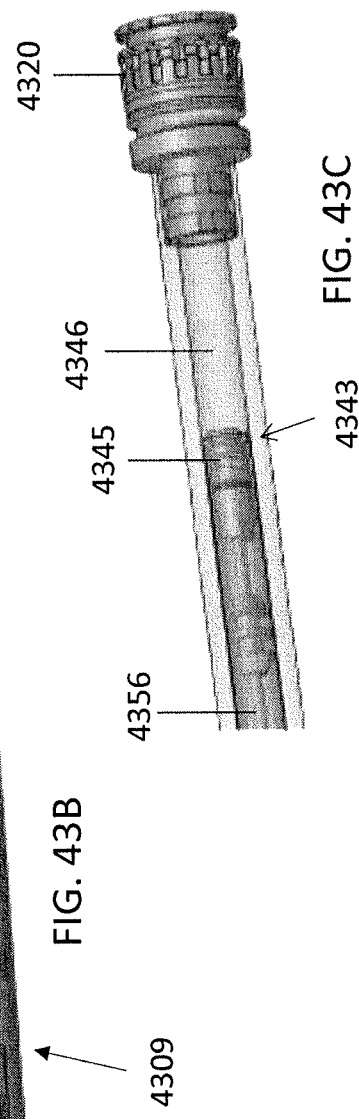

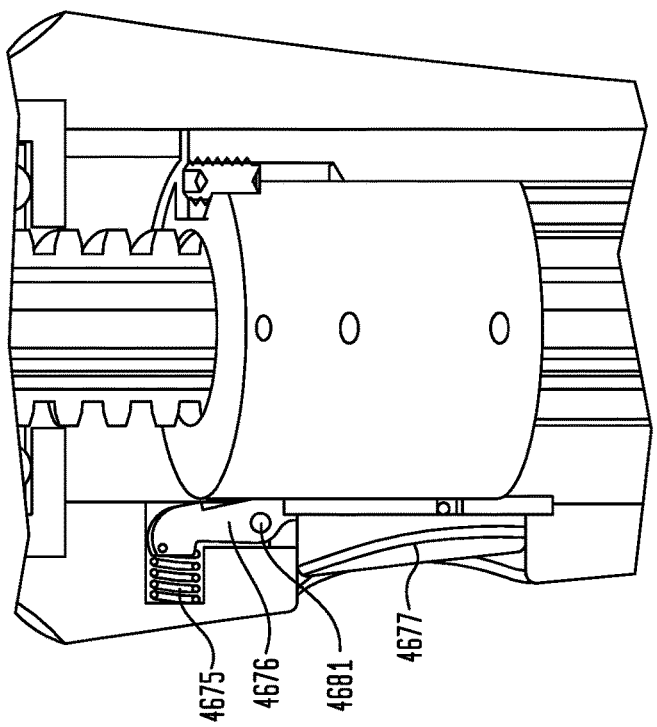
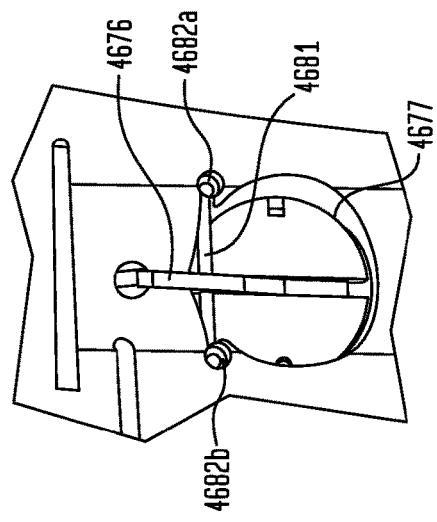
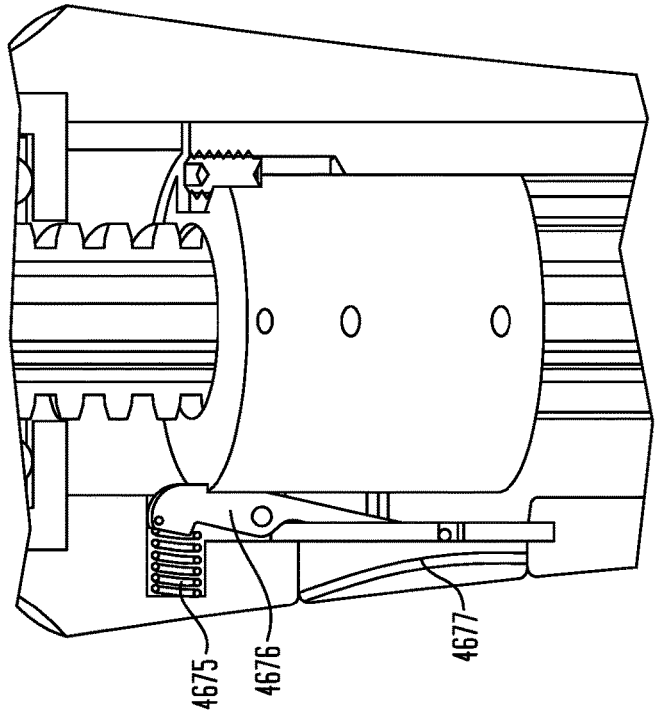

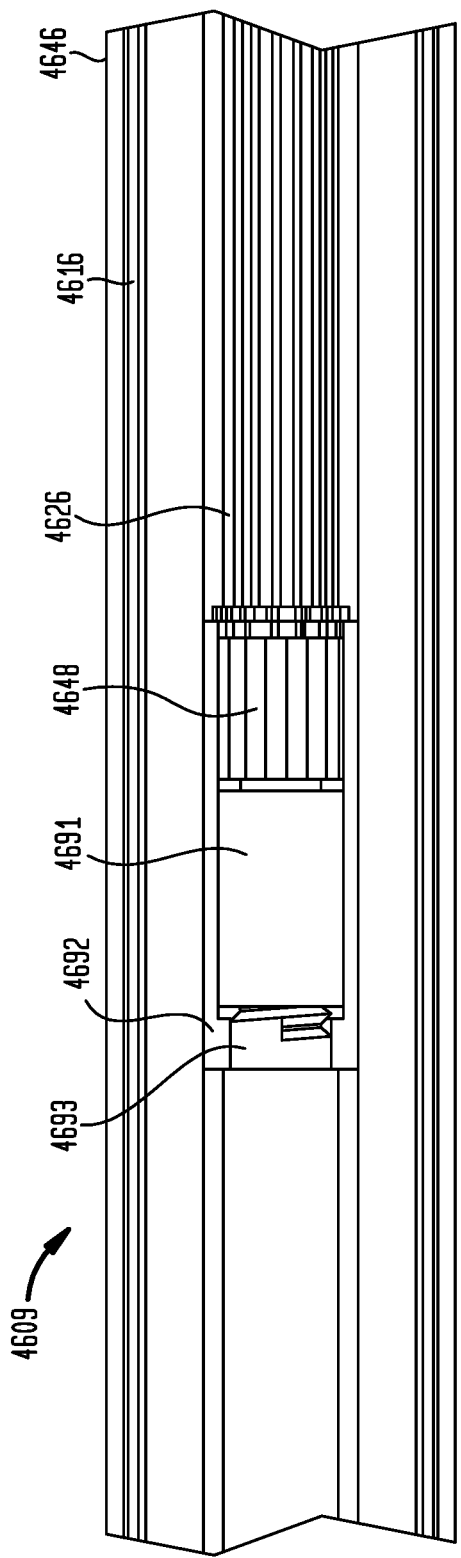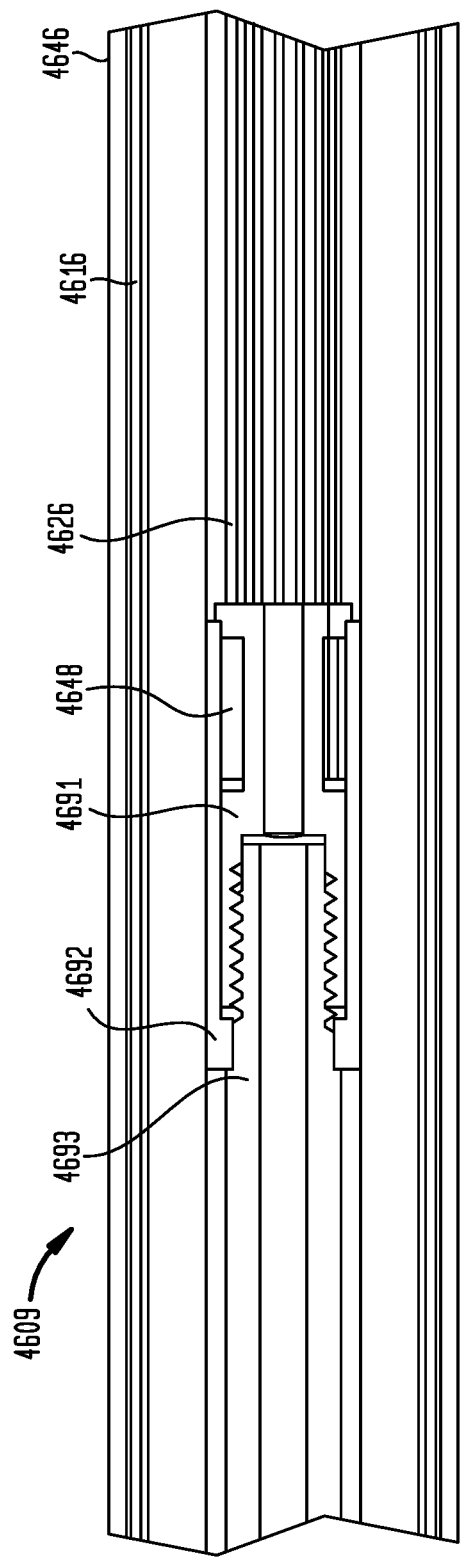

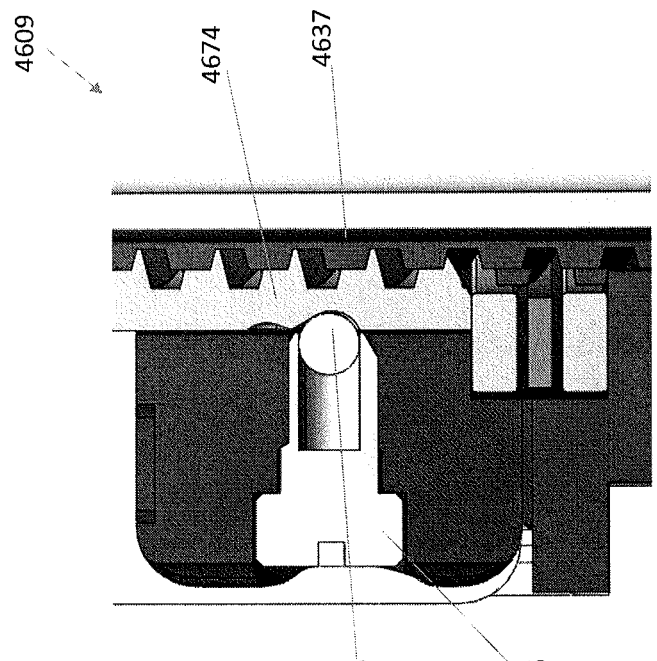
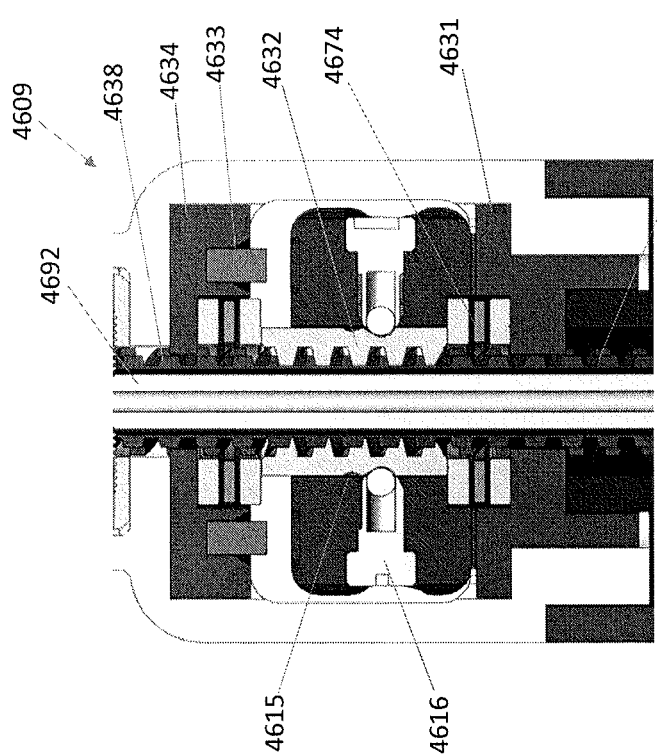
FIG. 46S
FIG. 46R

CARDIAC VALVE DELIVERY DEVICES AND SYSTEMS

CROSS REFERENCE TO RELATED APPLICATIONS

This application is a national phase entry under 35 U.S.C. § 371 of International Patent Application No. PCT/US2017/062045, filed on Nov. 16, 2017, published in English, which claims priority to U.S. Provisional Application No. 62/424,051, filed on Nov. 18, 2016, the entireties of which are hereby incorporated by reference herein.

This application maybe related to International Patent Application No. PCT/US2016/032546, filed May 13, 2016 and titled "CARDIAC VALVE DELIVERY DEVICES AND SYSTEMS," which is incorporated by reference herein in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates generally to the treatment of cardiac valve disorders, such as mitral valve replacement. In particular, this application is directed towards devices for delivering and placing replacement mitral valves.

BACKGROUND

The mitral valve lies between the left atrium and the left ventricle of the heart. Various diseases can affect the function of the mitral valve, including degenerative mitral valve disease and mitral valve prolapse. These diseases can cause mitral stenosis, in which the valve fails to open fully and thereby obstructs blood flow, and/or mitral insufficiency, in which the mitral valve is incompetent and blood flows passively in the wrong direction.

Patients suffering from such diseases can be treated with prosthetic valve replacements, such as mitral valve replacements. These replacements can be implanted through minimally invasive or cardiopulmonary bypass surgical techniques.

Prosthetic valve replacement procedures can be difficult, and various factors are generally taken into account when placing the valve. First, the prosthetic valve should be placed at the same or very nearly the same angle as the native valve. A valve that is off axis could cause turbulent blood flow and/or potential para-valvular leaks. Second, the prosthetic valve should ideally have concentricity. This means that the valve is placed in the same center as the native valve. An off center deployment or valve placement could affect the mechanism of neighboring valves or the heart's conductive system. Finally, the prosthetic valve should be at the proper depth within the patient's heart with respect to the location of the native valve, as otherwise, the prosthetic valve may interfere with the conductive nature of the heart as well.

A safe and efficient delivery system and method for replacement of a cardiac valve that addresses some or all of these concerns is described herein.

SUMMARY

In general, in one embodiment, a delivery device includes a handle, a central elongate member extending from the handle, a sheath configured to, slide over and relative to the central elongate member, a distal tether retainer at a distal end of the central elongate member, a proximal tether restraining mechanism positioned along the central elongate member distal of the handle and proximal of the distal tether retainer, and a plurality of tethers. The tethers are configured to extend from the proximal tether restraining mechanism to the distal tether retainer.

This and other embodiments can include one or more of the following features. The proximal tether restraining mechanism can be between 1 and 3 inches away from the distal tether retainer. The proximal tether restraining mechanism can include a mini clamp mechanism positioned within the sheath. The mini clamp mechanism can include a set of washers around which proximal ends of the plurality of tethers are wound. The delivery device can further include a screw and nut within the sheath and sandwiching the washers, and the nut can be configured to rotate relative to the screw to allow the washers to pull apart and release the proximal ends of the tethers. The proximal tether restraining mechanism can include one or more crimps positioned within the sheath. There can be a separate crimp for each tether. There can be a single crimp fitting configured having a plurality of holes extending therethrough, and each hole can be configured to house a separate tether. The proximal tether restraining mechanism can be configured to move axially to tighten or loosen the tethers. The handle can further include a tether control configured to axially move the proximal tether restraining mechanism. The tether control can be a knob. The knob can be configured to move axially from a proximal position to a distal position, and the proximal position can provide free spinning of the knob, and the distal position can provide ratcheting of the knob. The knob in the proximal position can be configured to rotate in both a first direction and a second direction to provide tightening and loosening of the plurality of tethers. The knob in the distal position can be configured to rotate only in the first direction to provide tightening of the plurality of tethers but not loosening of the plurality of tethers. The delivery device can further include a sheath control configured to axially slide the sheath relative to the central elongate member. The distal tether retainer can include a plurality of pockets therein. The plurality of tethers can each include a feature on the distal end thereof configured to fit within a pocket of the plurality of pockets to hold the distal end in place. The proximal tether restraining mechanism can be an annular tether retainer having a plurality of pockets therein. The plurality of tethers each include a feature on the proximal end thereof configured to fit within a pocket of the plurality of pockets to hold the proximal end in place. The proximal tether restraining mechanism can include at least one coiled spring configured to hold proximal ends of the plurality of tethers.

In general, in one embodiment, a delivery device includes a handle, a central elongate member extending from the handle, a first sheath configured to slide over and relative to the central elongate member, and a second sheath positioned over the first sheath. The second sheath has a first configuration and a second configuration. The second sheath in the first configuration can be axially fixed relative to the central elongate member and axially movable relative to the first sheath. The second sheath in the second configuration can be axially fixed relative to the first sheath and axially movable with the first sheath relative to the central elongate member.

This and other embodiments can include one or more of the following features. The second sheath can include a marker thereon configured to align with a center of a mitral valve. The marker can be an annular ring that extends radially outwards relative to a remainder of the second sheath. The handle can include a control configured to control movement of the first sheath. The control can be a knob. The delivery device can further include a tether retainer at a distal end of the central elongate member and a plurality of tethers extending axially to the tether retainer. The first and second sheath can be configured to move proximally to expose the tether retainer only upon activation of a release mechanism on the handle. The release mechanism can be a latch. The handle can further include a tether control configured to tighten or loosen the plurality of tethers. The second sheath can be configured to transition from the first configuration to the second configuration when the first sheath is pulled proximally so that a distal end of the first sheath and a distal end of the second sheath are aligned.

In general, in one embodiment, a delivery device includes a handle, a central elongate member extending from the handle, a sheath, and control knob, and a torque bar. The sheath is configured to slide over and relative to the central elongate member. The control knob is on the handle and is configured to rotate to move the sheath axially relative to the central elongate member. The torque bar is configured to be attached and detached from the control knob during use. The torque bar extends radially outwards relative to the control knob when attached.

This and other embodiments can include one or more of the following features. The control knob can include a plurality of radial notches, and the torque bar can be configured to fit between two of the plurality of radial notches. The torque bar can include one or more posts configured to mate with the control knob. The knob can be configured to rotate in a first direction to move the sheath distally and in a second direction to move the sheath proximally. The torque knob can be configured to abut a portion of the handle to prevent rotation in the second direction. The delivery device can further include a tether retainer at a distal end of the central elongate member and a plurality of tethers extending to the tether retainer. The sheath can be configured to slide axially to expose or cover the tether retainer.

In general, in one embodiment, a delivery device includes a central elongate member, a sheath configured to slide over the central elongate member, a plurality of tethers extending through the central elongate member, a plurality of hypotubes extending through the elongate member, a handle, and a control. Each tether is configured to loop through a portion of a prosthetic valve. Each of the hypotubes is configured to house a tether and to curve proximally when extended out of the elongate central member. The handle is connected to the elongate member, the sheath, and the plurality of tethers. The control is on the handle and is configured to move the sheath proximally and distally over the central elongate member to extend the plurality of hypotubes distally out of the elongate central member and to loosen the tethers from the prosthetic valve.

In general, in one embodiment, a method of delivering a prosthetic mitral valve includes extending a prosthetic delivery device into a heart with the prosthetic mitral valve collapsed within a sheath of the delivery device, sliding the sheath to expose at least a proximal anchor of the prosthetic valve, loosening a plurality of tethers of the delivery device that are coupled to the proximal anchor to allowing the proximal anchor to self-expand to an expanded annular configuration on a first side of the mitral valve annulus, pushing the proximal anchor distally with a plurality of curved hypotubes of the delivery device that house the tethers, and allowing a distal anchor of the prosthetic valve to self-expand on a second side of the mitral valve annulus after allowing the proximal anchor to self-expand. The expansion of the distal anchor causes the distal anchor to move towards the proximal anchor and capture tissue of the mitral valve annulus between the proximal anchor and the distal anchor.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 24C shows the distal inner sheath of the delivery device of FIG. 24A extended in a position where proximal end petals are deployed.

FIG. 24D shows the distal inner sheathe extend at an even more distal position relative to FIG. 24C such that an entire prosthetic valve has been deployed.

FIG. 24E shows the distal inner sheath of FIG. 24A extended in the farthest distal end position such that pockets of a tether retainer are exposed and allow the tether ends to be freed.

FIG. 24F shows the tether ends of the device of FIG. 24A being retracted to allow the delivery device now to be removed.

FIG. 28D is a cross-section taken along the longitudinal axis of the device of FIG. 28A.

FIG. 28E another view of the device of FIG. 28A.

FIG. 28F is a cross section of FIG. 28E.

FIG. 28G is another cross-section of FIG. 28E.

FIG. 28H is another cross-section of FIG. 28E.

FIG. 36 shows an exemplary delivery device in which the tethers are attached to a movable mandrel.

FIG. 37A-37B show an exemplary delivery in which there are two tether retainers for holding both the proximal and distal ends of the tethers.

FIGS. 40A-40B show an exemplary delivery device including a tether clamping mechanism.

FIGS. 43A-43C show an exemplary delivery device including a mini clamp mechanism.

DETAILED DESCRIPTION

The delivery devices described herein can be used to deliver and deploy a wide variety of replacement heart valves, such as prosthetic mitral valves. Exemplary prosthetic valves that can be delivered and deployed with the delivery devices described herein include the expandable prosthetic valves described in U.S. Pat. No. 8,870,948, filed Jan. 31, 2014 and titled "SYSTEM AND METHOD FOR CARDIAC VALVE REPAIR AND REPLACEMENT," in International Patent Application No. PCT/US2016/032550, filed May 13, 2016 and titled "REPLACEMENT MITRAL VALVES," and in U.S. patent application Ser. No. 14/677,320, filed Apr. 2, 2015 and titled "REPLACEMENT CARDIAC VALVES AND METHODS OF USE AND MANUFACTURE," all of which are incorporated by reference herein. For example, the delivery devices herein are configured to be able to delivery and deploy a replacement heart valve, such as a mitral valve, that includes distal and proximal anchors.

Replacement heart valves can be collapsed into a delivery configuration so they can fit within the delivery devices described herein. The replacement heart valves can be delivered to the treatment site within the delivery device and then deployed. The delivery device can be configured such that the distal and proximal anchors can be sequentially deployed as desired from a collapsed configuration to an expanded configuration. If necessary, the replacement valves can be repositioned, re-sheathed (partially or completely) if necessary, and then re-deployed.

In some embodiments, the delivery devices described herein can be used to deliver a cardiac valve prosthesis through a surgical route (e.g., during a cardiopulmonary bypass) or through a transatrial route (e.g., by making a small incision in the patient's body and passing the prosthesis through the apex of the heart to, for example, the mitral valve). In such a surgical or transatrial delivery method for a mitral valve replacement, the distal-most anchor is delivered to the ventricle while the proximal-most anchor is delivered to the atrium.

Figure 1:
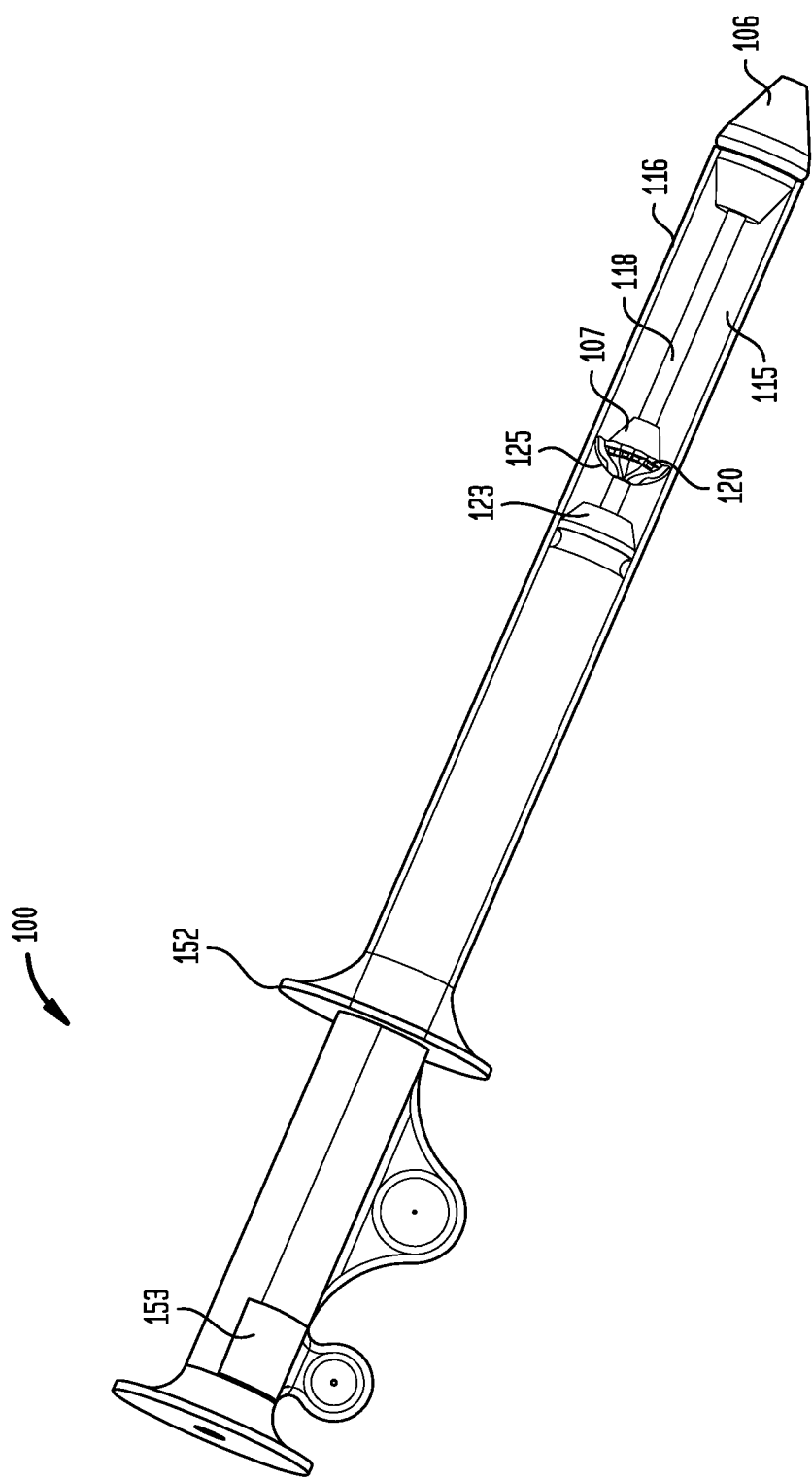
FIG. 1 is shows an exemplary prosthetic valve delivery device.

FIG. 1 illustrates an exemplary delivery device 100 that is configured to deliver and deploy a mitral valve prosthesis, e.g., through a transatrial delivery method. The delivery device 100 allows self-expansion of a distal portion of the prosthesis, such as a distal anchor, and controlled deployment of a proximal portion of the prosthesis, such as a proximal anchor. The delivery device 100 includes a central control assembly that includes a central hub 107, which has a lumen extending therethrough. Disposed within and secured within the lumen of the central hub 107 is central stem 118, which extends further distally than the central hub 107, and whose distal region is coupled to nosecone 106. The central control assembly further includes a retaining member 120 secured to the central stem 118 for controlling expansion of the valve prosthesis. Retaining member 120 is configured to interact with a proximal region of the prosthesis (not shown for clarity) and, with the use of sheath 116 as described below, facilitate a controlled deployment of the proximal region of the prosthesis.

Delivery device 100 further includes an outer sheath 116 coupled to sheath control 152. The central control assembly is disposed within sheath 116, and the system is configured so that sheath 116 can be axially moved (proximally and distally) relative to the central control assembly. The distal region 123 of central hub 107, the proximal end of nosecone 106, and the inner surface of sheath 116 define a prosthesis delivery region 115, which is configured to receive and retain therein a prosthesis in a collapsed configuration for delivery.

While the prosthesis is not shown for clarity, in this configuration of the delivery device, the expandable prosthesis would be in a collapsed configuration inside delivery region 115 due to the radial constraint provided by sheath 116. When collapsed, the proximal portion of the prosthesis interacts with, e.g. is attached to, raised elements 125 of retaining member 120. The proximal portion of the prosthesis can include a plurality of self-expandable cells, arcs, or arches (generally referred to herein as cells), such as those features described in application Ser. No. 14/677,320, U.S. Pat. No. 8,870,948, and International Patent Application PCT/US2016/032550, incorporated by reference above. The cells of the proximal portion of the prosthesis (e.g., the proximal anchor), when collapsed, interface with raised elements 125 such that they are looped around raised elements 125. Raised elements 125 project radially outward, extending further radially than valleys 119, which are in between adjacent raised elements 125 and whose configuration is defined by the configuration of the projecting raised elements 125. The raised elements 125 are configured and sized so that when sheath 116 is positioned over the raised elements 125 (i.e., is disposed radially outwardly relative thereto), the space between the inner surface of sheath 116 and the radially outermost surface of raised elements 125 does not allow the cells of the proximal portion of the prosthesis to pass through the space. Raised elements 125 and sheath 116 are therefore sized and configured to maintain the proximal-most portions of the prosthesis proximal to raised elements 125 while the rest of the prosthesis is positioned distal to the raised elements 125. This prevents the proximal portion of the prosthesis from expanding sooner than desired as the sheath is being retracted proximally during deployment of the prosthesis.

The sheath 116 and raised elements 125 are also sized and configured to allow the self-expandable proximal portion of the valve prosthesis to expand radially outward only after the distal end of the sheath 116 has been retracted far enough proximally relative to raised elements 125. Upon removal of sheath lock 153, sheath 116 can be retracted proximally relative to central control assembly to expose the prosthesis and allow for self-expansion. That is, when the distal end of sheath 116 is retracted proximally past raised regions 125, the expandable proximal portion of the prosthesis will expand to its expanded configuration since the radially constraint of the sheath has been removed.

Figure 2A:
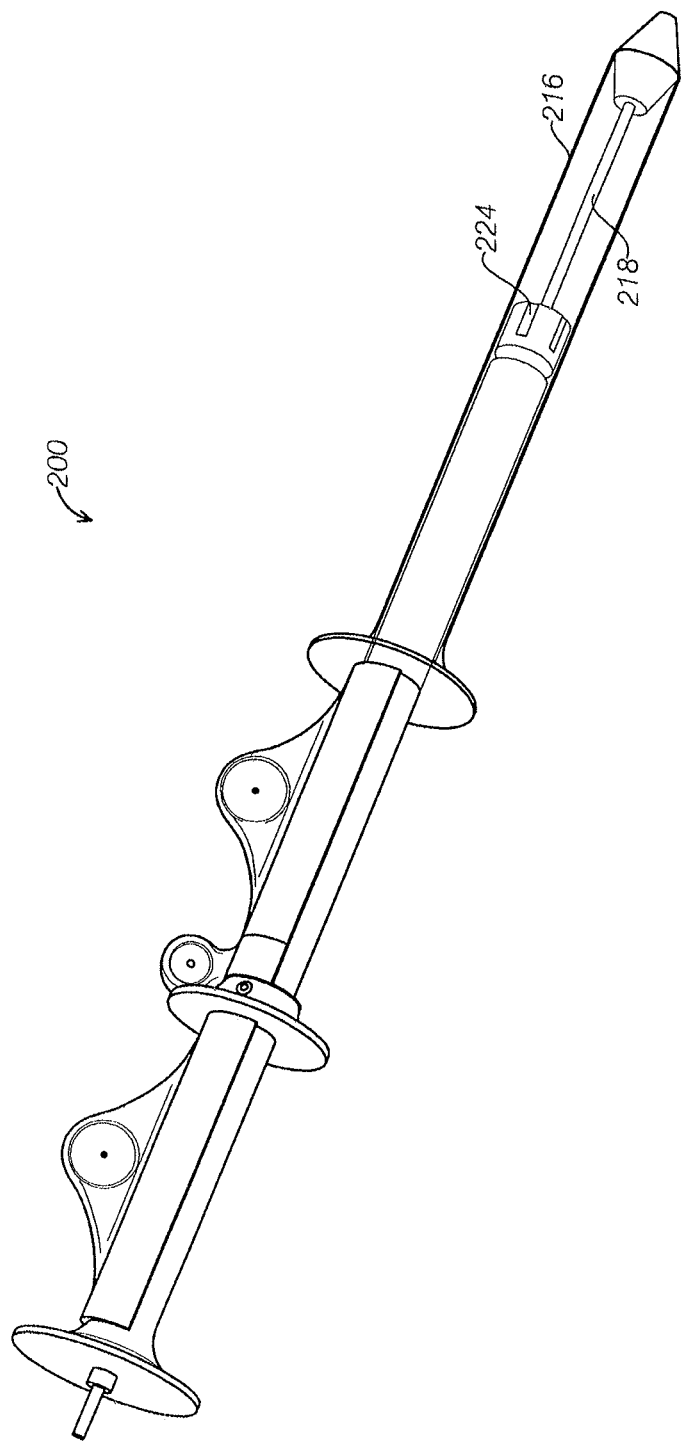
FIG. 2A shows another embodiment of a prosthetic delivery device.
Figure 2B:
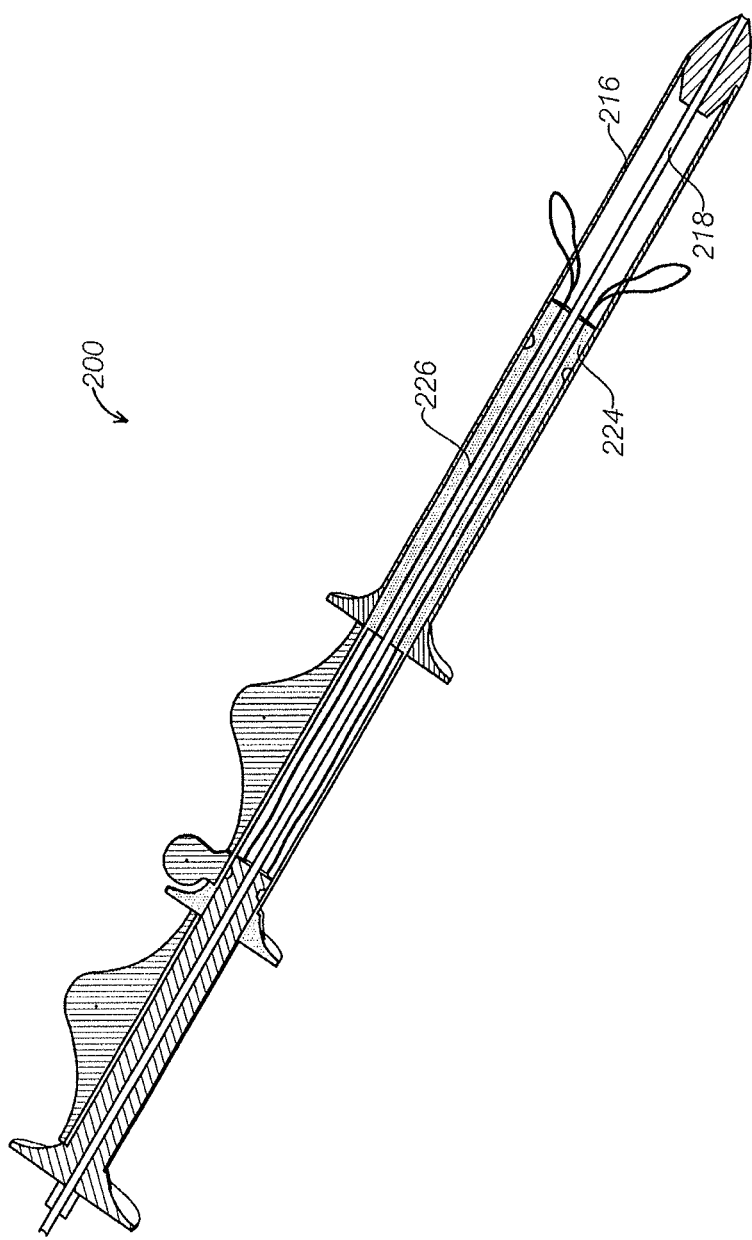
FIG. 2B is a cross-section of FIG. 2A.

FIGS. 2A-2B show a delivery device 200 that is configured to control the expansion of the proximal portion of the anchor (as is the embodiment in FIG. 1) while allowing for recapture and/or movement of the proximal anchor was deployed. The delivery device 200 thus includes a central stem 218, a proximally retractable sheath 216, and a central control assembly. The central control assembly includes a plurality of looped tethers 226 (see FIG. 2B) extending therethrough and an annular member with constraining elements 224 extending therearound.

The tethers 226 extend down the center of the device 100. The tethers 226 form a loop at the distal end through which the constraining elements 224 extend. In use, the looped tethers 226 can be extended through portions of a prosthetic valve, such as the proximal anchor, and then the ends of the tethers 226 can loop around the constraining elements 224 (which are held in place by the sheath 216, as described below). The tethers 226 can be configured to be loosened using controls in the handle. When the loops of the tether 226 are loosed, the proximal end, of the prosthetic valve can expand, and when the loops are tightened, the proximal end of the prosthetic valve can collapse. Exemplary materials for the tethers 226 include polymers such as Force Fiber HDPE tether, a wire of nitinol, tungsten or stainless steel, or a braided tungsten or stainless steel cable.

The constraining elements 224 can be formed, for example, of a shape memory material and are configured to extend through the loops of tether 226, as described above. In some embodiments, the constraining elements 224 include a plurality of shape memory, e.g., nitinol, flaps or strips that are held down by the sheath 216, but open, release, or expand when the sheath 216 is retracted. The sheath 216 can thus retain the plurality of constraining elements 224 in closed or captured configurations, thereby ensuring that the tethers remain looped through the valve.

FIGS. 2A and 2B show the sheath 216 extended fully distally over the stem 218. In this configuration, the valve prosthesis would be fully enclosed within the sheath 216, i.e., with the distal portion of the valve prosthesis held in the collapsed configuration by the sheath 216 and with the proximal portion of the valve prosthesis held in the collapsed configuration by the tightened tethers 226, which are in turn held in place by the constraints 224.

Figure 3:
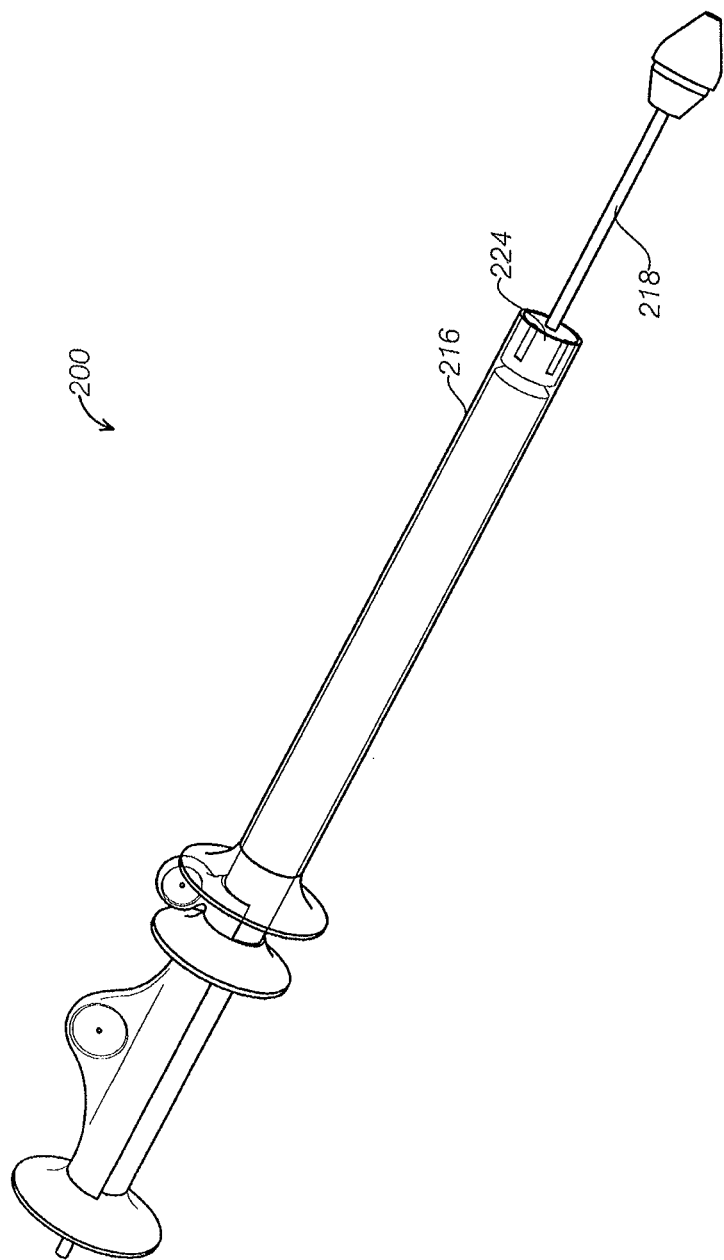
FIG. 3 shows the delivery device of FIG. 2A with the sheath partially proximally withdrawn.

FIGS. 2A-6 illustrate a sequence of using the device 200. Thus, FIG. 3 shows the delivery device 200 after sheath 216 has been partially proximally withdrawn relative to the central stem 218 such that the distal end of the sheath 216 is substantially aligned with the distal end of the annular member with constraining elements 224. In this position, the distal end of the prosthesis, e.g., the distal anchor, would be allowed to self-expand and/or deploy. However, because the distal end of the sheath 216 is still distal to the capture elements 224, the capture elements 224 are still in their closed configuration, thereby maintaining their hold on the tethers 226.

Figure 4:
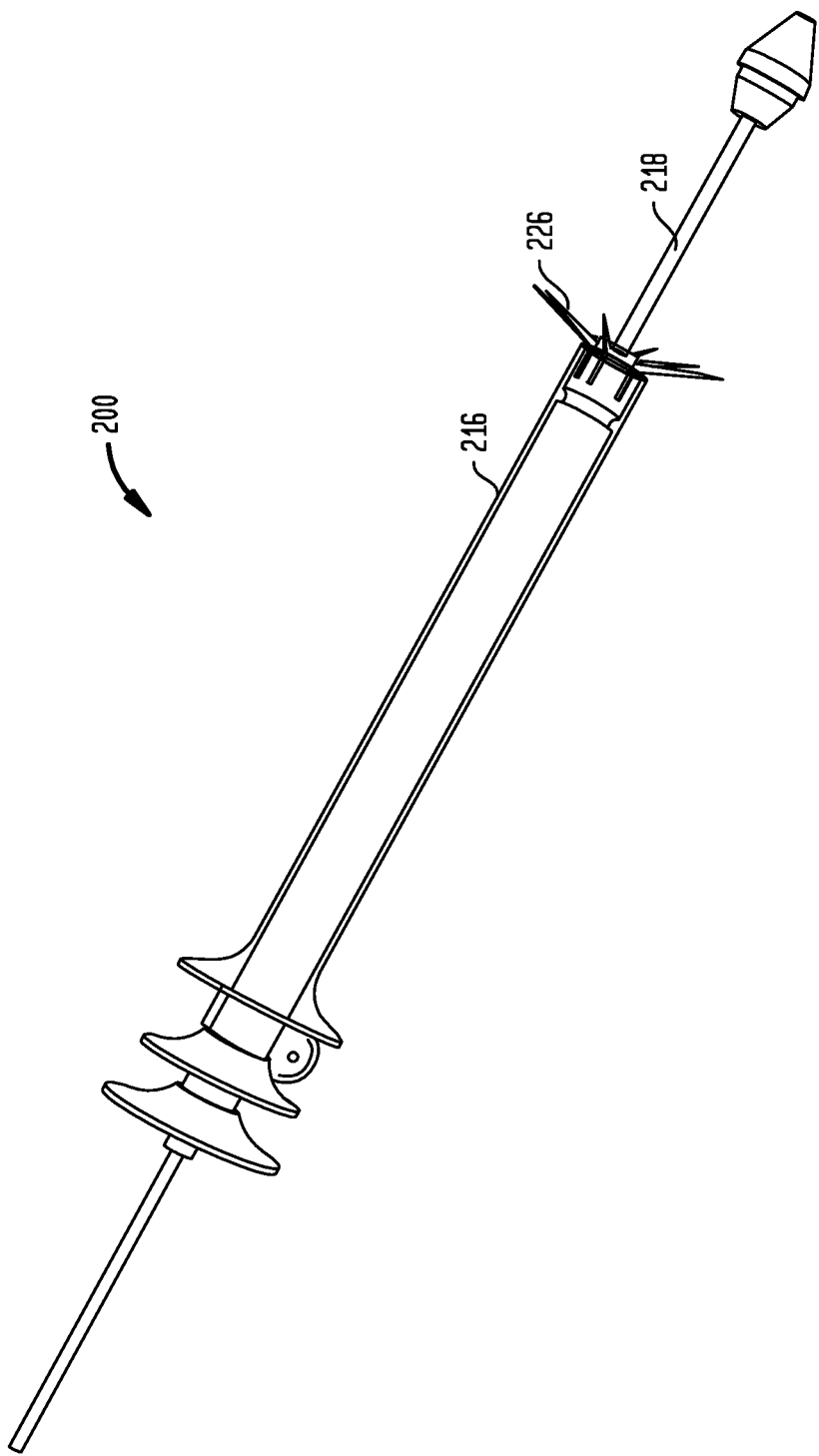
FIG. 4 shows the delivery device of FIG. 2A with the tethers exposed.

FIG. 4 shows the delivery device after tethers 226 are distally advanced by distally advancing the proximal most handle 109. Distally advancing the looped tethers 226 loosens the loops relative to the prosthesis and allows the proximal portion of the prosthesis to be expanded. Tethers 226, however, are still in position relative the proximal side to collapse the proximal anchor if needed.

Figure 5:
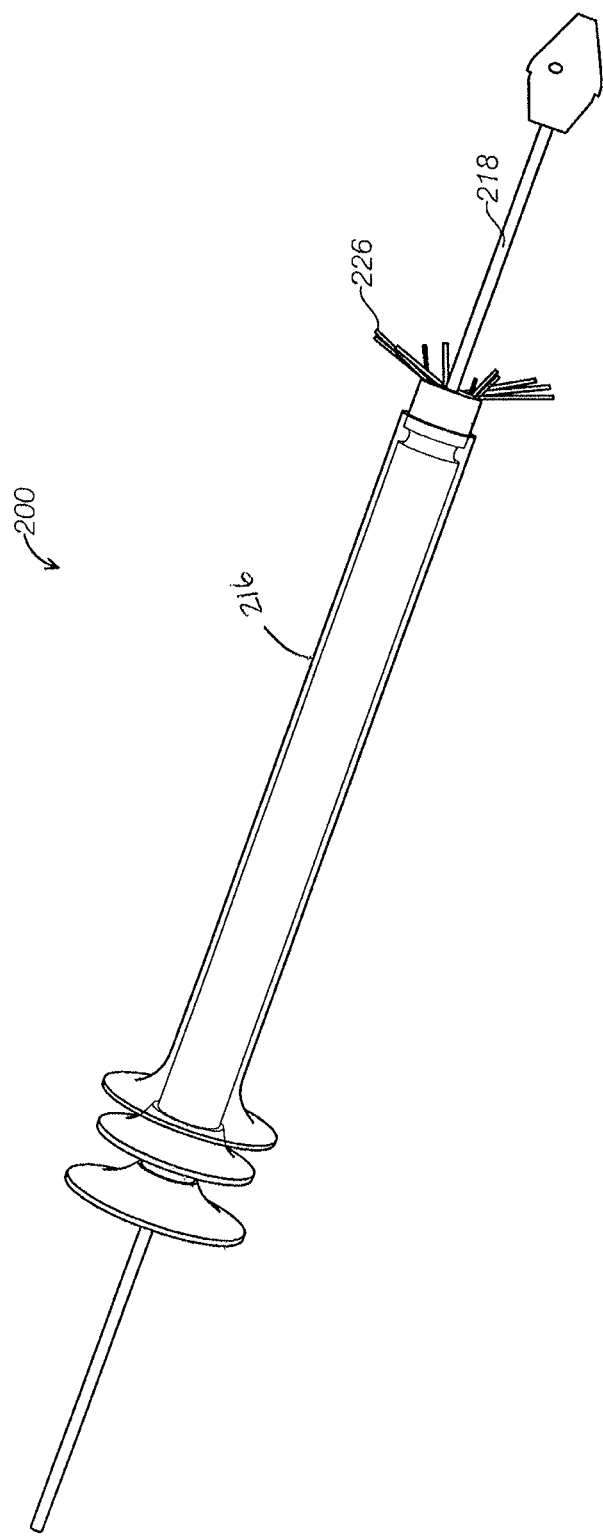
FIG. 5 shows the delivery device of FIG. 2A with the tethers partially retracted.

Thus, referring to FIG. 5, the tethers 226 can advantageously be pulled distally, thereby tightening the tethers 226 and collapsing the proximal anchor (e.g. for movement and/or optimal placement of the prosthesis). FIG. 5 thus shows the tethers 226 tightened, which would in turn recollapse the proximal portion of the prosthesis. If needed, the entire valve can be retrieved back inside sheath 216, where the delivery device looks like what is shown in FIG. 2 after sheath has been advanced distally.

Figure 6:
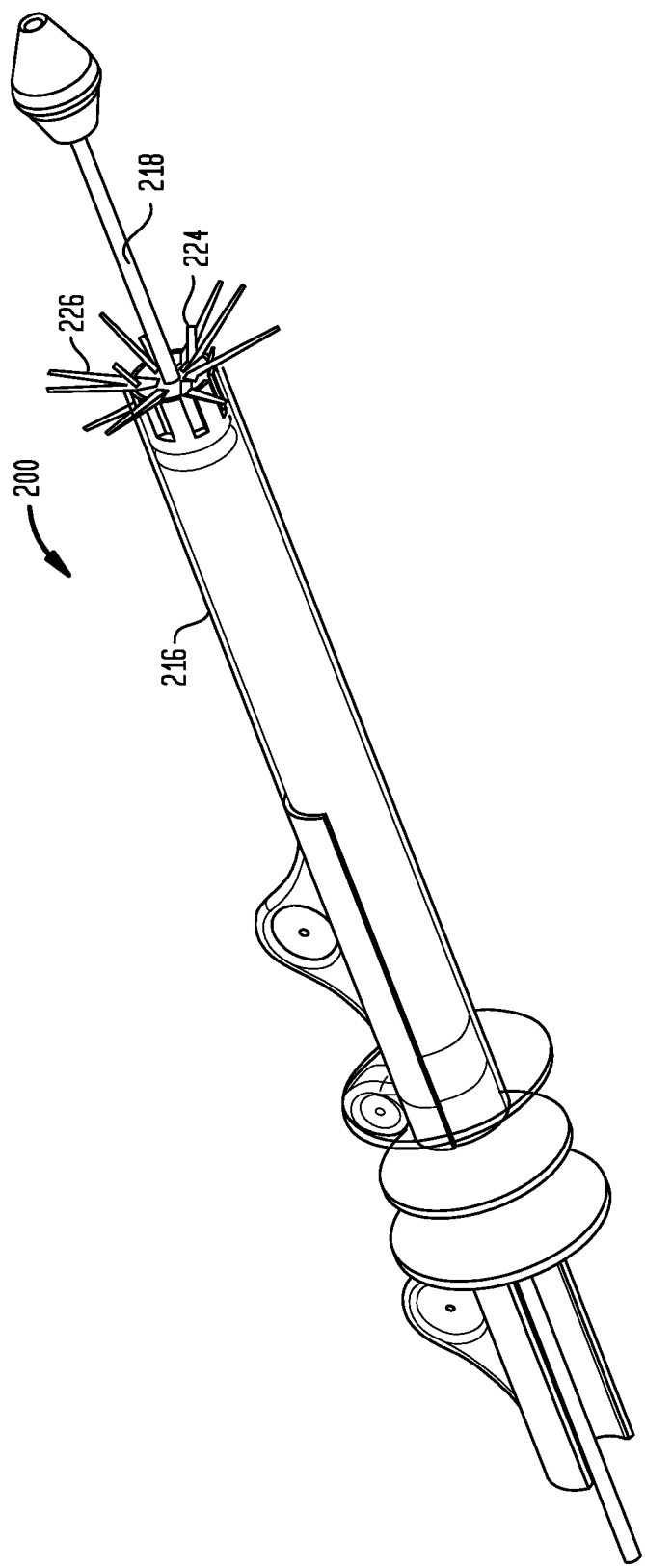
FIG. 6 shows the delivery device of FIG. 2A with the tethers and retaining elements fully released.

Referring to FIG. 6, to fully deploy and release the prosthesis (i.e., after positioned properly with the tethers 226 still attached), the sheath 216 can be pulled distally past the constraining members 224, thereby causing the tethers 226 to pop out of the constraining members 224.

Figure 7:
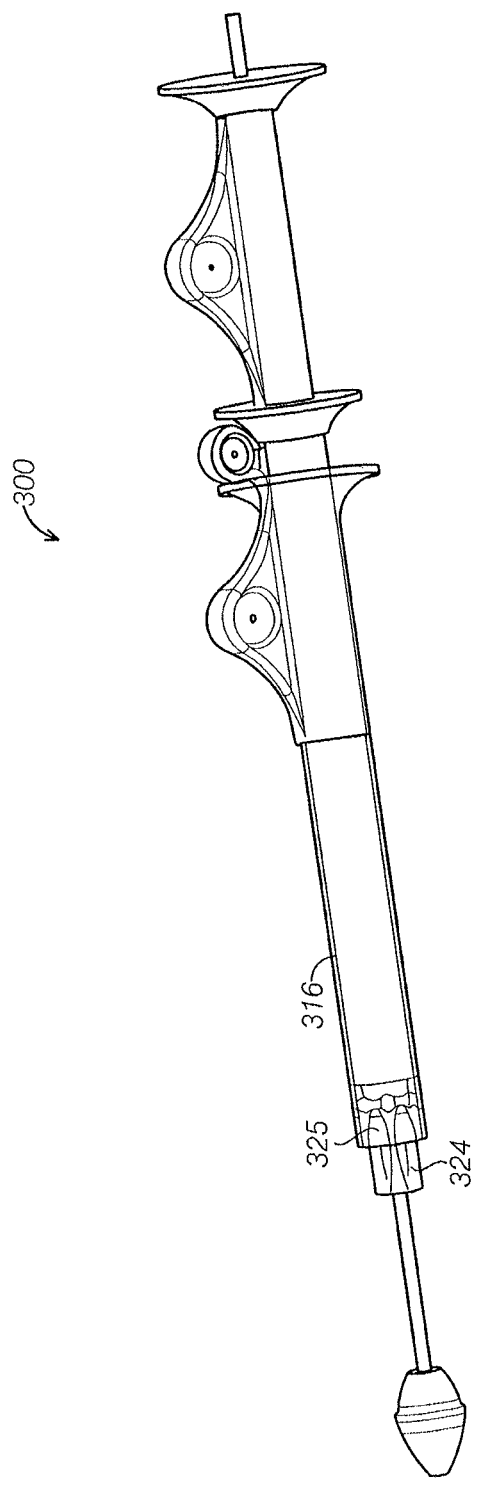
FIG. 7 shows another embodiment of a prosthetic valve delivery device.

FIG. 7 shows another embodiment of a delivery device 300 that is similar to the embodiment in FIGS. 2-6. In this embodiment, however, capture elements 324 do not have shape memory configurations. In this embodiment, capture elements 324 are configured to passively change configurations from a closed or capture configuration to an open or release configuration. Each of the retaining elements 324 is configured to mate with, or be keyed with, an indentation 325 of the central assembly. In this embodiment, the capture elements 324 have a substantially triangular shape. The mating configurations (with the sheath 316 thereover) keeps the capture elements 324 mated with the indentations 325. When sheath 316 is retracted past the capture elements 324, the capture elements 324 will not automatically revert to an open configuration due to the material properties of the retaining elements 324. Rather, they will be forced to an open configuration due to the self-expanding properties of the proximal portion of the prosthesis. Tethers or other additional restraining elements can again be used to further control the expansion of the proximal portion of the prosthesis, as is described in the embodiment of FIGS. 2-6.

Figure 8:
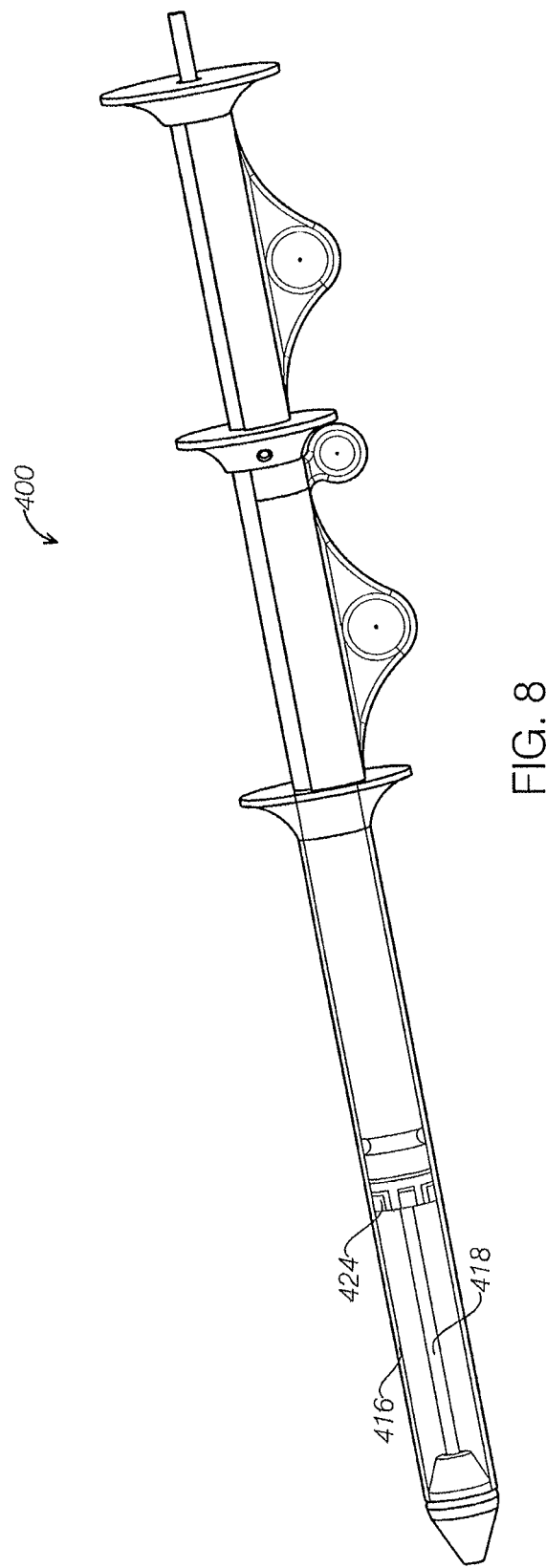
FIG. 8 shows another embodiment of a prosthetic valve delivery device.

FIG. 8 illustrates another delivery device 400. The delivery device 400 includes a central stem 418 and a sheath 416, similar to as described with respect to other devices described herein. Further, capture elements 424 function similar to capture elements 324.

Figure 9:
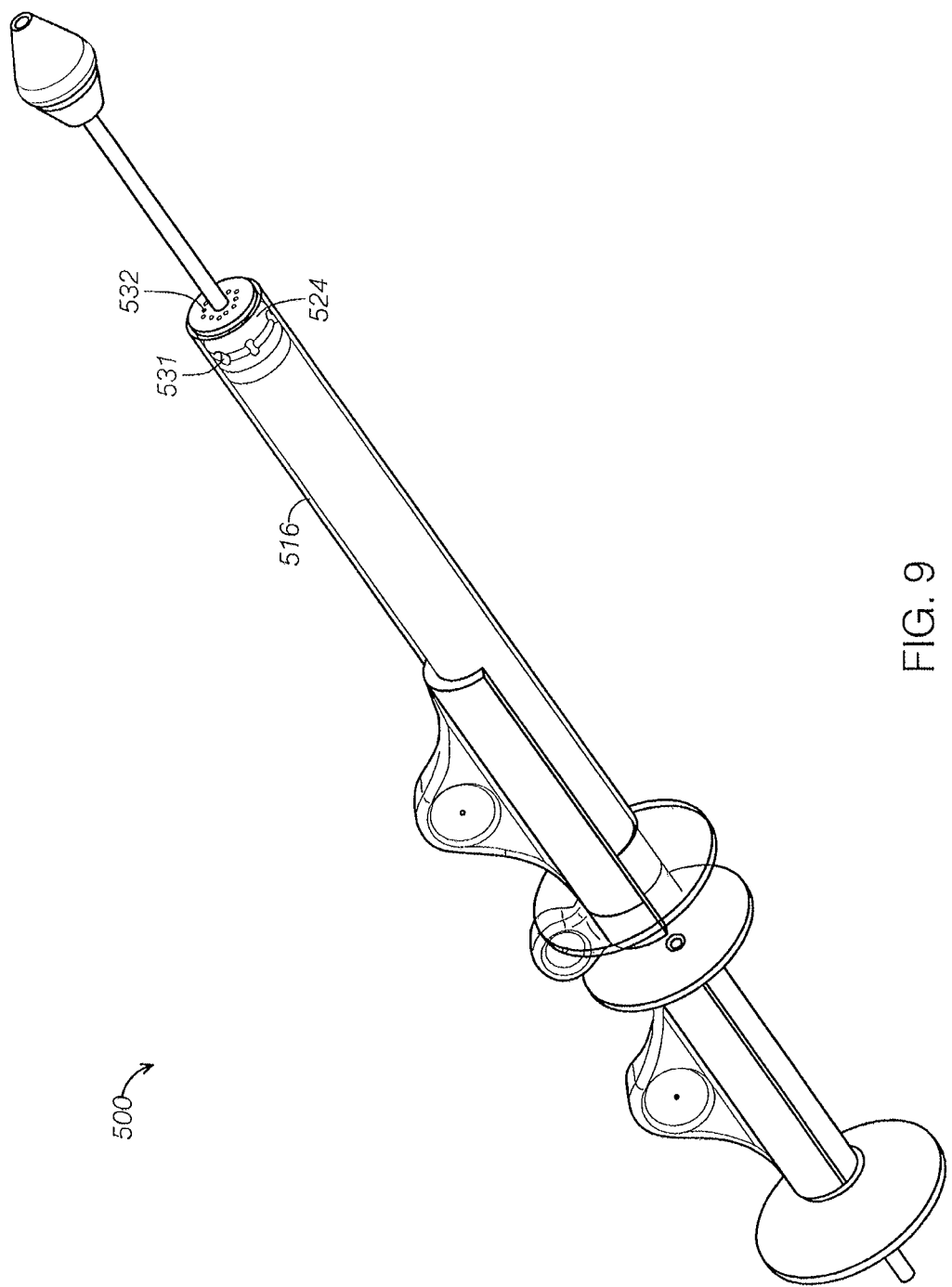
FIG. 9 shows another embodiment of a prosthetic valve delivery device.

FIG. 9 illustrates an alternative delivery device 500 having a tether ends retainer 524 with pockets 531 therein configured to hold the ends of a tether (i.e., rather than having the tether loop around a capture element). The details of such a tether ends retainer 524 are described further below with respect, for example, to FIG. 11A. The tethers extend through tether lumens 532. In some embodiments, the ends of the tethers (or sutures, wires, or other controllable restraining elements) can include a radiopaque marker in a region configured to change position when the proximal portion has been released from the restraining elements. For example, the radiopaque marker can be in a region that is configured to "open." By including a marker on the portion that is configured to change position when the proximal portion has been released (and optional expanded), visualization can be used to determine when the proximal portion has been released by the restraining elements and expanded.

Figure 11A:
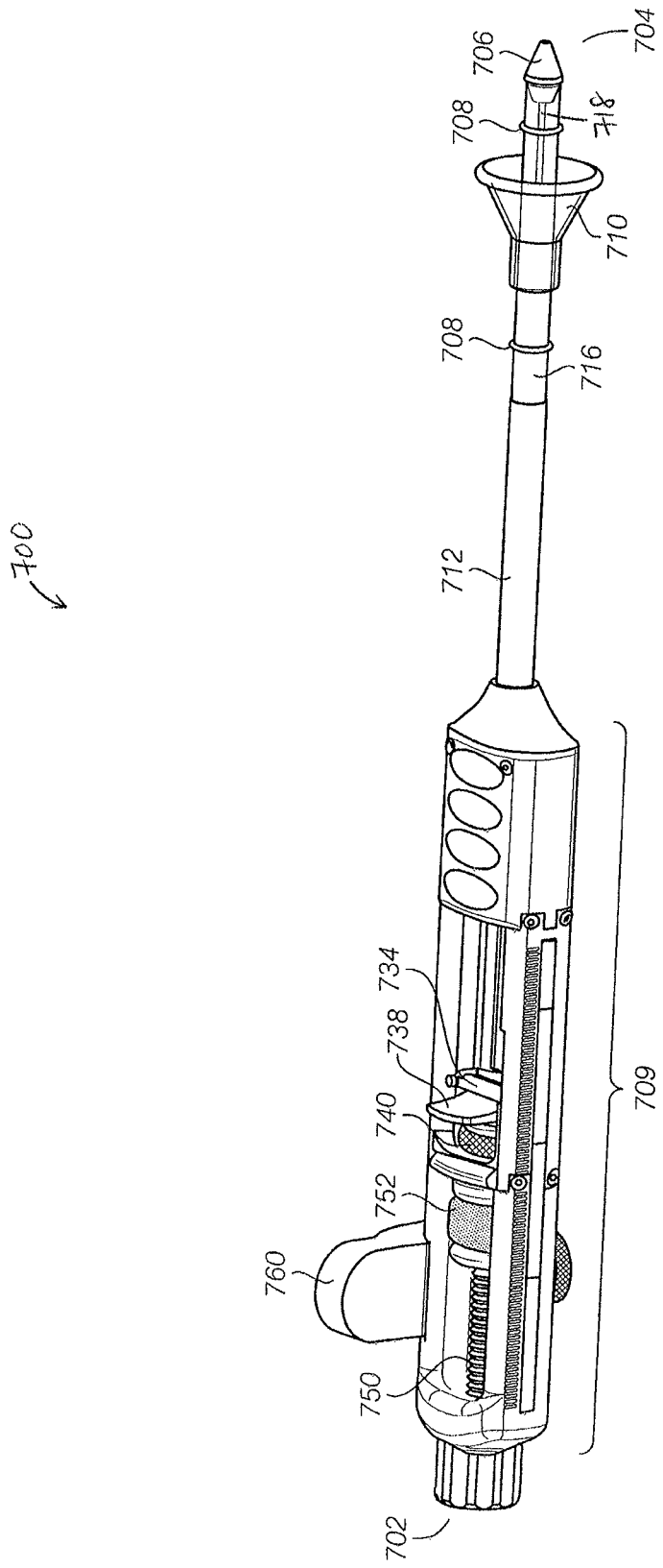
FIG. 11A shows another embodiment of a prosthetic valve delivery device.
Figure 11B:
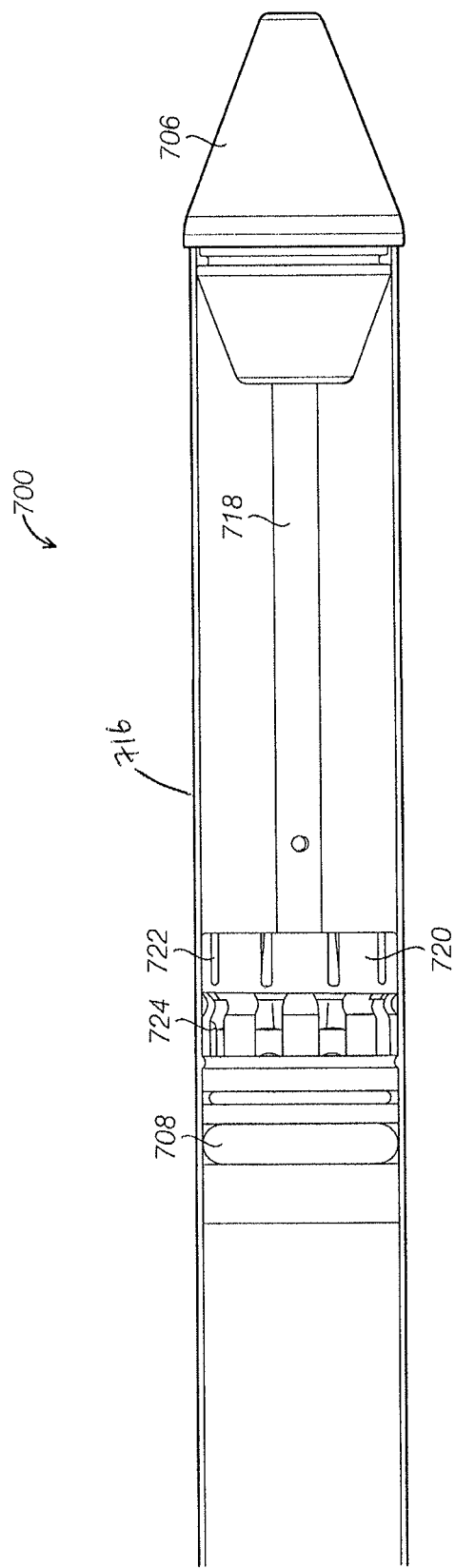
FIG. 11B shows a close-up of the delivery device of FIG. 11A without an outer sleeve and a tether loading cone.
Figure 11C:
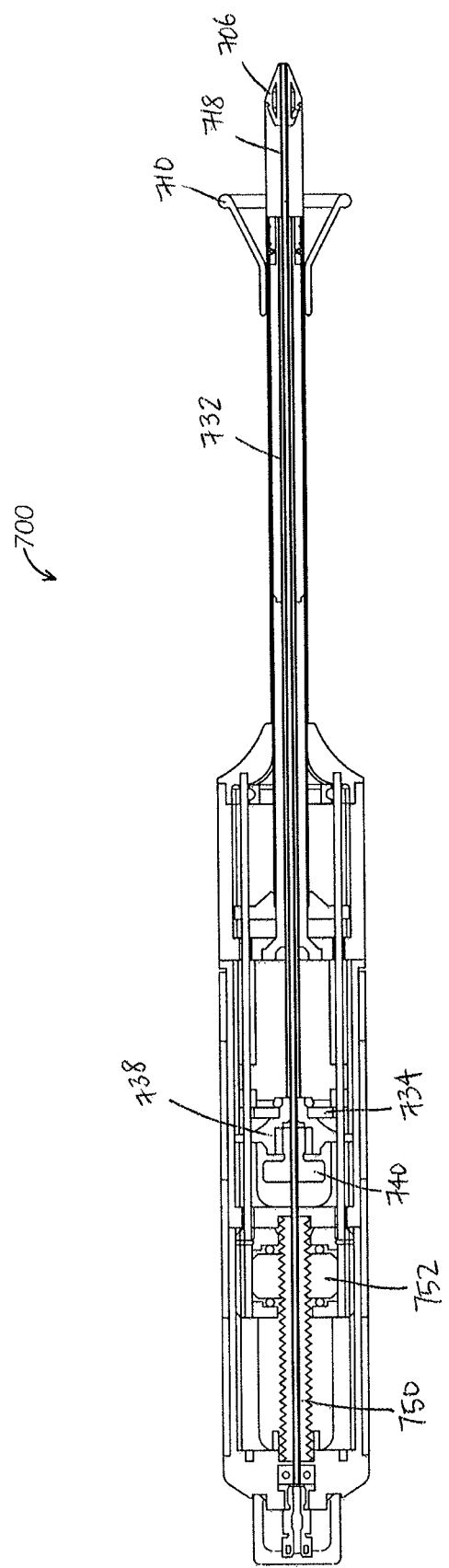
FIG. 11C shows a cross-section of the delivery device of FIG. 11A along its longitudinal axis without a grasper.

FIG. 11A shows another embodiment of a prosthetic valve replacement delivery device 700. The delivery device 700 includes a device proximal end 702 and a device distal end 704. As can be seen from FIGS. 11A-11C, the delivery device 700 has an elongated portion that terminates at a nosecone 706 at the device distal end 704. The nosecone 706 is coupled to a central stem 718, which is in turn coupled to a tether ends retainer 720 (described in detail below). The elongated portion includes an outer sheath 712 and an inner sheath 716. The central stem 718 also couples to a series of tether/suture maintaining hypodermic tubes that are able to slide along the central stem 718 (the hypodermic tubes will be further described below). The inner sheath 716 is configured to slide relative to the central stem 718 (extend and retract) to cover or expose certain retaining features of the delivery device, e.g., the tether ends retainer 720, (see FIG. 11B) as well as aid with maintaining the prosthetic valve within the delivery device 700 prior to deployment. The device proximal end 702 includes a handle 709 for holding onto the delivery device. Other components maintained within the proximal portion of the delivery device 700 will be discussed below. FIG. 11B shows a close-up of the distal end the delivery device 700, where it is more apparent that the nosecone 706 is attached to the central stem 718 and the central stem 718 is coupled to a tether ends retainer 720. FIG. 11C shows a cross-sectional view of the delivery device 700.

As best shown in FIG. 11B, the nosecone 706 is located at the device distal end 704 of the delivery device 700 and includes a tapered distal tip. The nosecone 706 is configured to aid with inserting the delivery device 700 into a position within a patient's heart for successful valve placement. The nosecone 706 tip has a small surface area such that if the nosecone 706 touches any portion of the patient's heart, less damage will be done to the heart. The nosecone 706 tip is also rounded or blunt so as to decrease the risk of puncturing the patient's heart if the nosecone tip contacts the surface of the heart.

Tethers 726 (see FIG. 20) aid with maintaining the prosthetic valve within the device 700. In most cases, the tethers are made of suture materials. The proximal ends are maintained with a clamping mechanism 771 (including the tether control lever 738) while the distal ends are maintained within the tether retainer 720. The lengths of tether extend along and around the center stem 718, and each thread through a separate tubular structure. The tether ends that couple to the tether retainer 720 further include a feature for coupling the tether ends to the tether retainer 720, as is further discussed below.

Figure 16A:
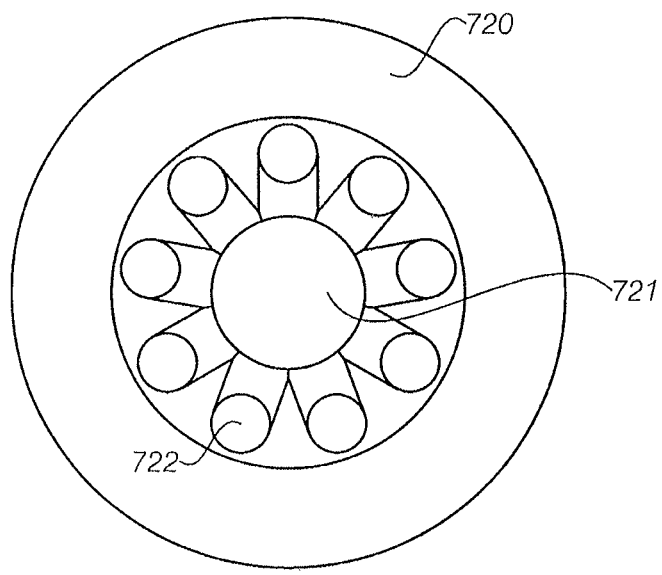
FIG. 16A and FIG. 16B show a tether ends retainer from on top and angled side view.
Figure 16B:
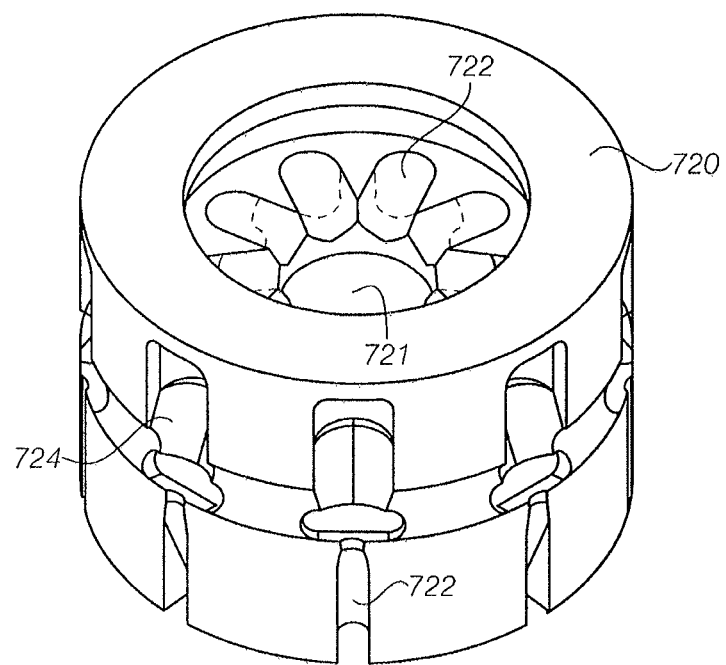

The distal ends of the tethers are configured to loop through the proximal end, such as the prosthetic anchor, of the prosthetic valve. The distal ends of the tethers, once looped through the prosthetic anchor, are maintained by the tether retainer 720. The tether retainer 720 in relation to the delivery device 700, to the central stem 718 and the nosecone 706, can be seen in FIG. 11B. FIG. 16 also shows the tether retainer 720 unattached and by itself from two different angles. The tether retainer 720 has a substantially annular or cylindrical shape and has dimensions that allow it to fit within the inner sheath 716. The tether retainer 720 includes a tether retainer center aperture 721 and an array of apertures 723 within its internal core. The tether retainer center aperture 721 maintains the tether retainer 720 within the delivery device 700. The tethers can be threaded through the array of apertures 723, one tether per aperture. A series of hypotubes 732 (see FIG. 13C) are aligned with each of the apertures 723. Each single tether is threaded through a hypotube 732 prior to exiting through the array of apertures. The hypotubes 732 allows the individual tethers to be evenly spaced about the delivery device 700 and prevents asymmetric arrangement of the tethers around the central stem 718. Symmetric loading ensures symmetric tensioning of the proximal end petals of the prosthetic valve, improving the loading of the device and the release characteristics. In this embodiment, there are nine apertures and nine hypotubes that maintain individual tethers at an even spacing within the delivery device body. In other examples, there may be more or fewer apertures and hypotubes for maintaining individual or multiple tether lines.

Figure 20A:
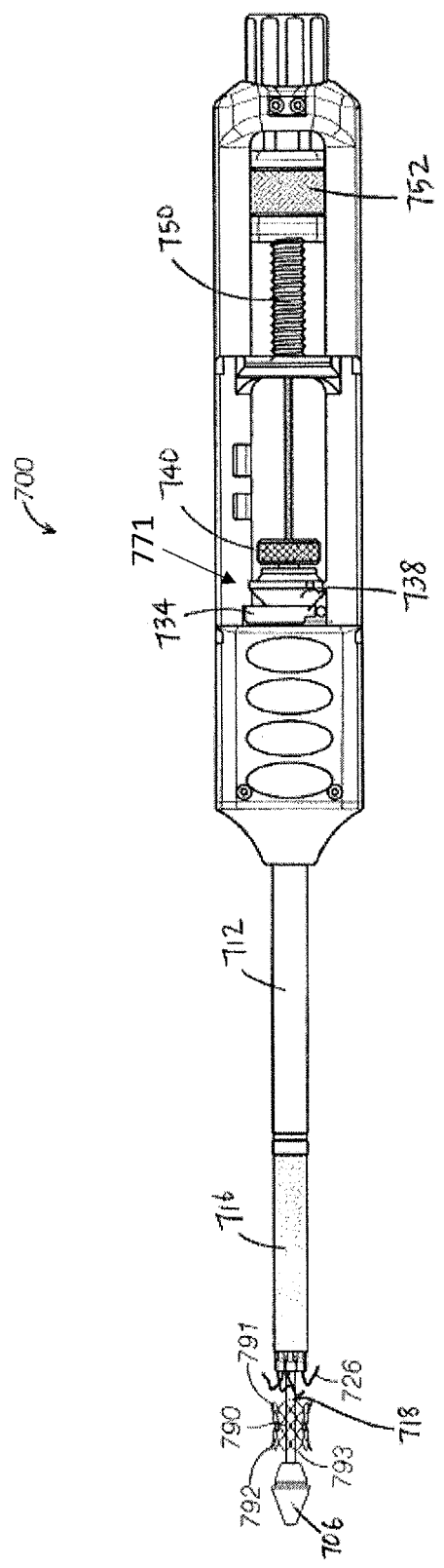
FIG. 20A shows the delivery device of FIG. 11A having a prosthetic valve inserted onto the distal end but uncoupled to the delivery device.
Figure 20B:
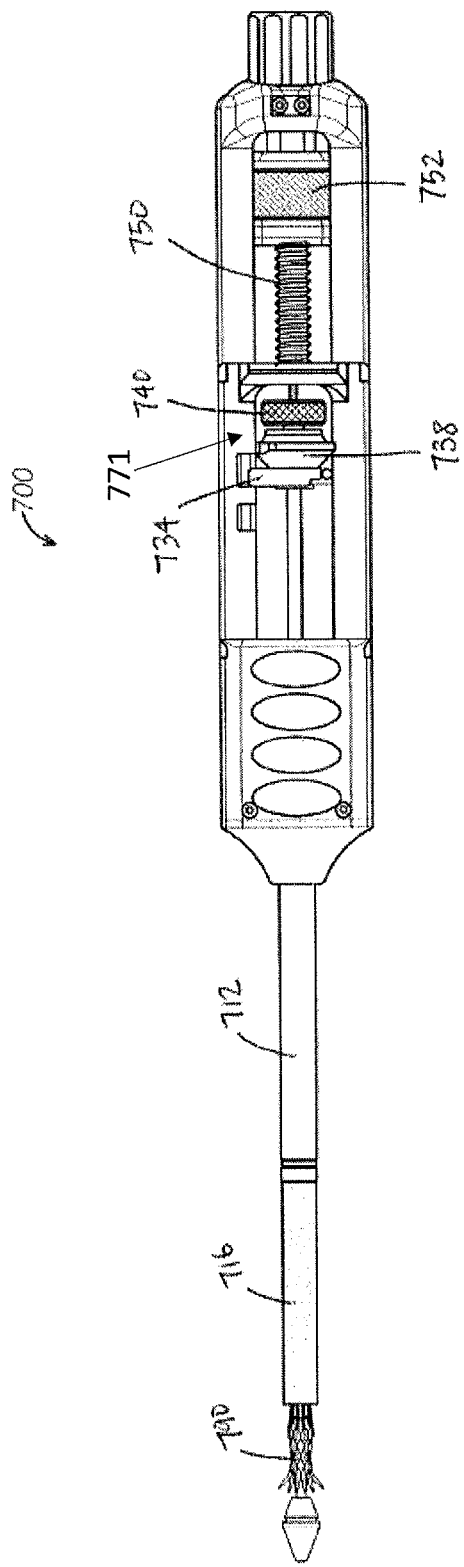
FIG. 20B shows the delivery device of FIG. 11A having the prosthetic valve attached at its proximal end but not drawn into the delivery device.

Once all the tethers have been looped around the proximal end petals of the prosthetic valve, the free tether ends are brought back to the tether retainer 720. As can be seen from FIG. 16B, the outer surface of the tether retainer 720 includes a series of evenly spaced tether pockets 724 that are in fluid connection with corresponding series of tether slots 722. FIG. 20A shows the delivery device 700 having free tether 726 ends. Each tether 726 distal end can include a truncated cone, where an infinity knot at each tether end maintains the tether within the corresponding truncated cone. The truncated cones can be tapered distally to proximally. Each truncated cone may be inserted into one of the pockets 724 and then each tether maintained within the corresponding slot 722. The inner sheath 716 may be extended distally to cover the tether pockets 724. This aids with keeping the tether ends within the tether pockets 724.

The truncated cones on the distal end of the tethers may be made of any suitable rigid materials. The truncated cones are designed such that they easily release from the tether retainer 720. The geometry of the truncated cone are configured specifically to fit the tether pockets 724. The tether pockets 724 may also include additional features for maintaining the truncated cones of the tether ends when under tension. Further, the feature in the distal ends of the tethers need not be conical, but can be spherical or otherwise have a different shape. Materials for the distal features may include plastics, stainless steel, non-reactive polymers and so forth. Further, materials for the distal features may be chosen to maximize radio-opacity to aid confirmation of location/release under imaging during trans-atrial procedures. In one example, the distal features are fabricated at least partially from tantalum.

The tether retainer 720 may also have a groove at its proximal end for an O-ring 708. The O-ring is to prevent excessive blood from penetrating rest of the delivery device during a procedure. Moreover, the proximal end of the tether retainer 720 may have a diameter slightly less than that of the distal end. This allows the tether retainer 720 when fitted with the O-ring to still fit within the inner sheath 716.

The tethers 726 are used to control the prosthetic valve within the delivery device and aid with placement of the prosthetic valve at the mitral valve site. The series of distal tether ends are maintained within the tether retainer 720. Referring to FIG. 11A, the series of proximal end tethers are held by tether (atrial) control lever 738. The tether control lever 738 includes a series of apertures 739 for holding the proximal tether ends, where appropriate knots at the proximal tether ends hold the tethers in place. Alternatively, proximal tether ends may include a knot holding feature that prevents the tether end from slipping through the tether control lever 738. The tether control lever 738 is a lever that allows the operator to easily adjust the tension on the tether ends with their thumb. Once the tether ends have been threaded through the proximal end petals of the prosthetic valve and slotted into the tether pockets 724, the operator may tension the tether by pulling back on the tether control lever 738 and pull the prosthetic valve into the inner sheath 716. After the tether ends have been loaded, the tether control lock 734 may be flipped down to contact a tether control notch 736. The tether control lock 734 maintains the tethers in place.

Figure 17:
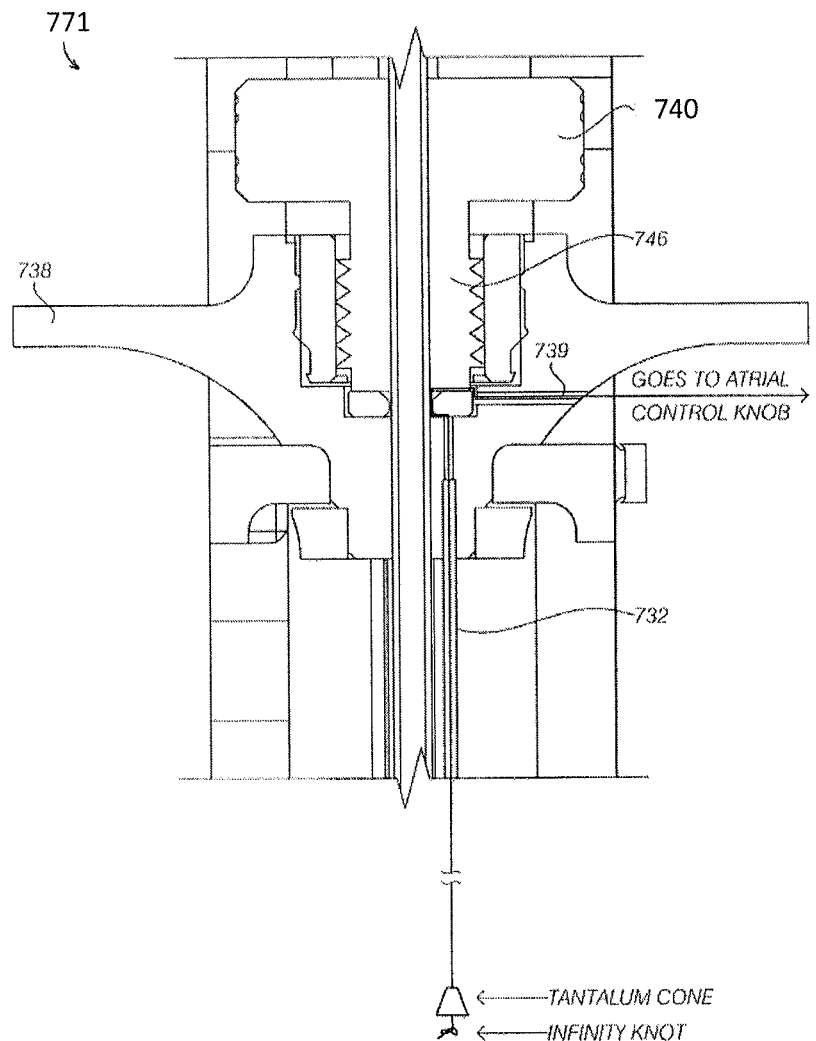
FIG. 17 shows a cross-section of a tether control lever and a secondary release knob.

Once the replacement has been loaded into the delivery device 700, tension can be maintained on the tethers with the tether clamping mechanism 771. In one embodiment, the tether clamping mechanism 771 can include a thumb screw 740 and a tether control lever 738. FIG. 17 is a close-up of a cross section showing the thumb screw 7140 and the tether control lever 738. A few of the hypotubes 732 are visible. The proximal tether ends enter the tether control lever 738 through tether control channels 739, and jog around a washer that is adjacent to thumbscrew 140 before it enters the hypotube 732 jogs. The thumbscrew 740, when it is tightened against the washer adjacent to the tether control lever 738, maintains tension on the proximal tether ends when the tether control lever 738 is pulled proximally.

Figure 12A:
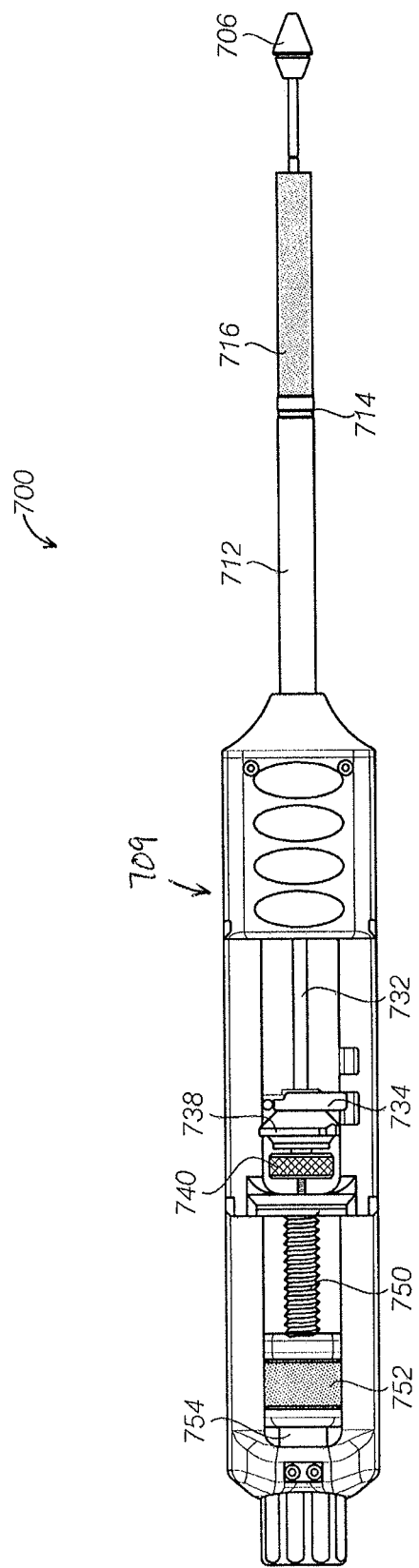
FIG. 12A shows the delivery device of FIG. 11A unsheathed.
Figure 12B:
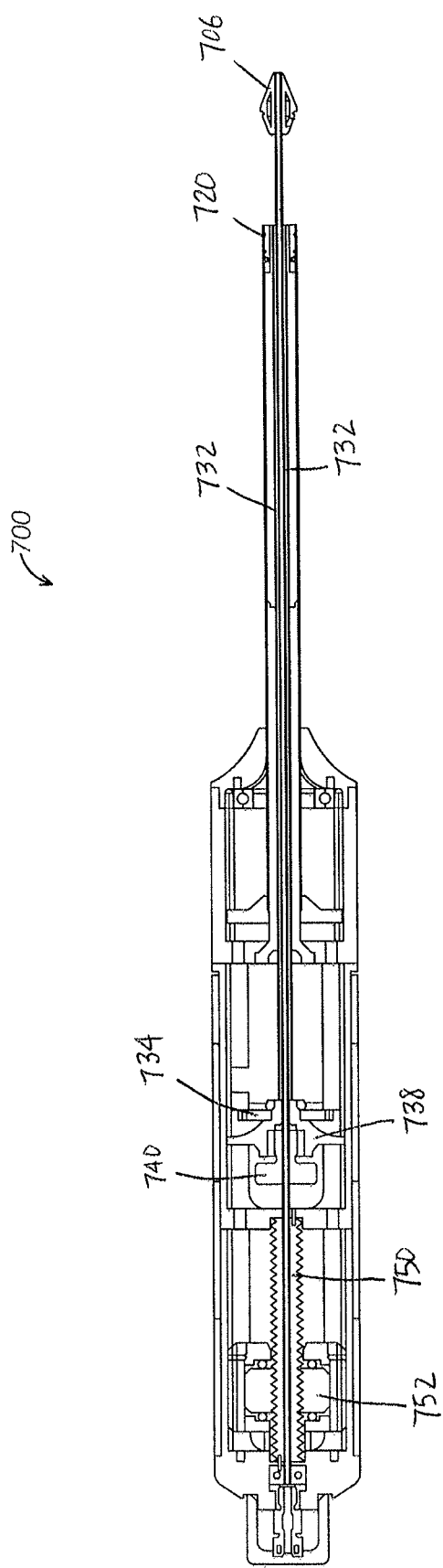
FIG. 12B shows a cross-sectional view of the unsheathed delivery device of FIG. 12A.
Figure 12C:
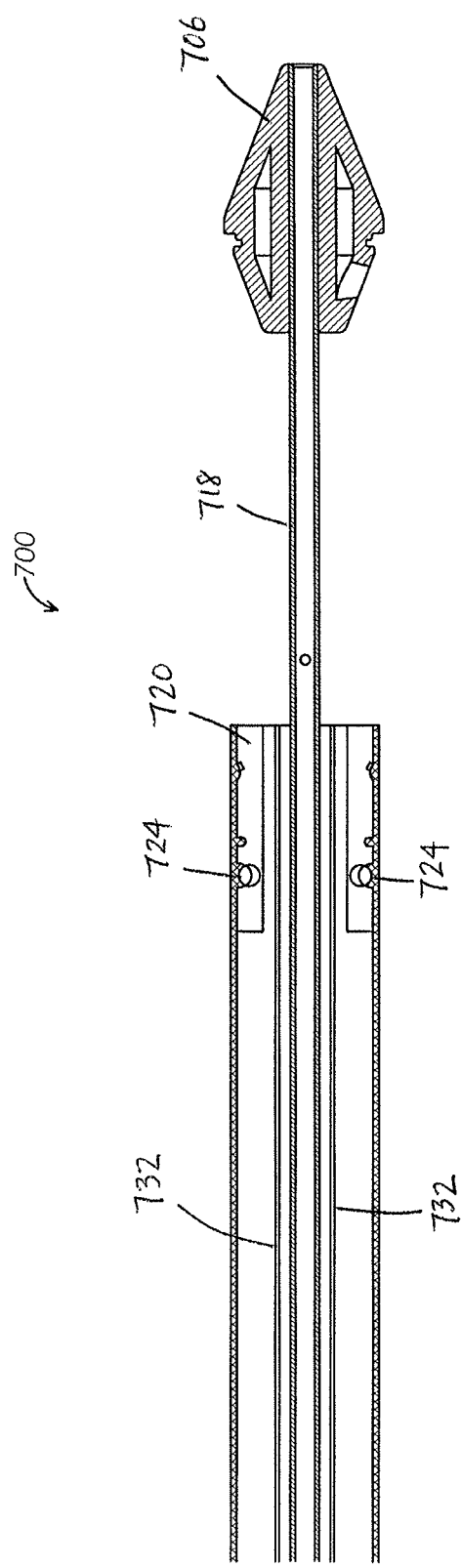
FIG. 12C shows a close up of the cross-section of the distal end of the unsheathed device of FIG. 12A.

Referring to FIGS. 12A-12C, the handle 709 of the delivery device 700 includes the tether control lever 738.

The tether control lever 738 is coupled with a thumbscrew 740. The tether control lever 738 and the thumbscrew 740 work to maintain the proximal ends of the tethers. Also coupled to the tether control lever 738 on its distal side are the series of hypodermic tubes 732 (hypotubes for short) that are disposed around the central stem 718. The series of hypotubes 732 each hold one tether and are able to extend and retract along with the tether control lever 738.

Figure 13A:
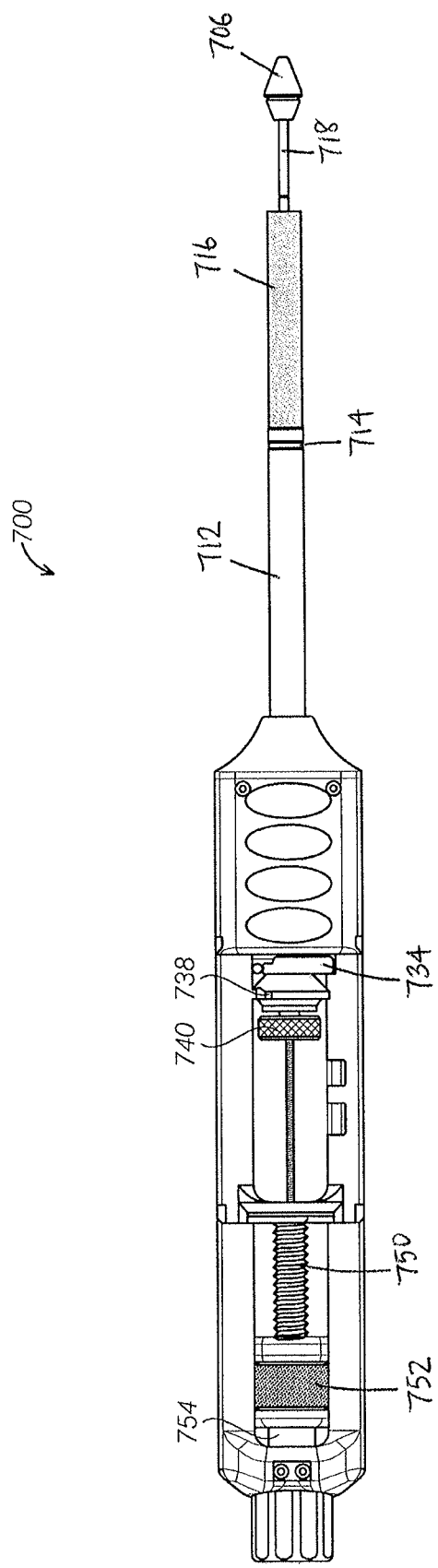
FIG. 13A shows the fully unsheathed delivery device of FIG. 12A where a tether control knob has been pushed distally along with a series of hypotubes for deploying a proximal end of a replacement prosthetic valve.
Figure 13B:
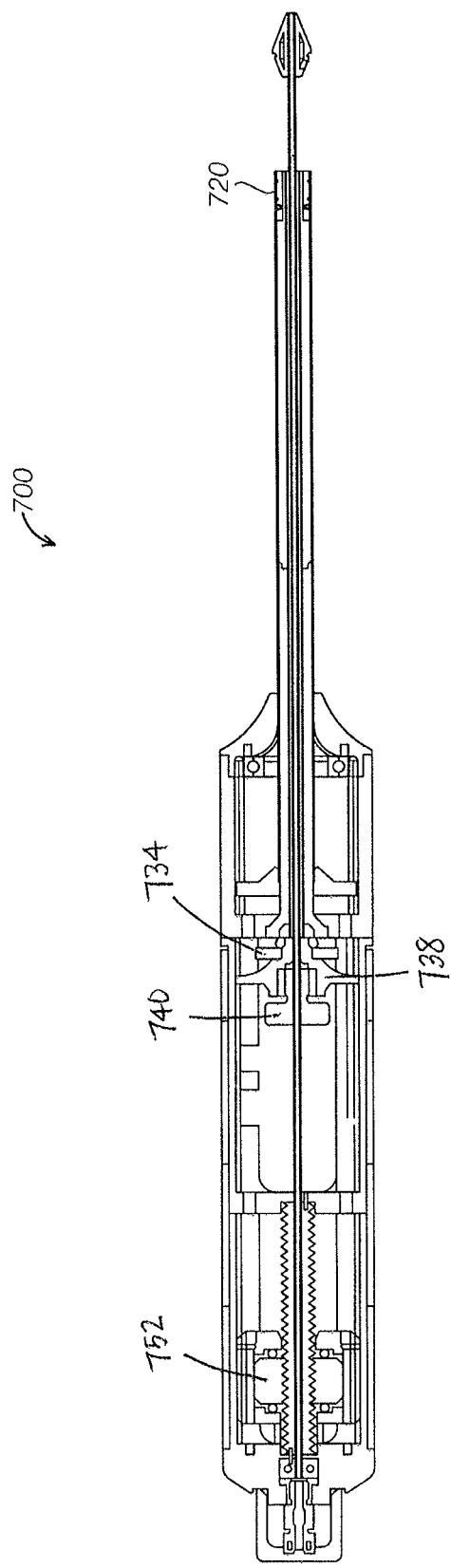
FIG. 13B is a cross-sectional view of the fully unsheathed delivery device of FIG. 13A.
Figure 13C:
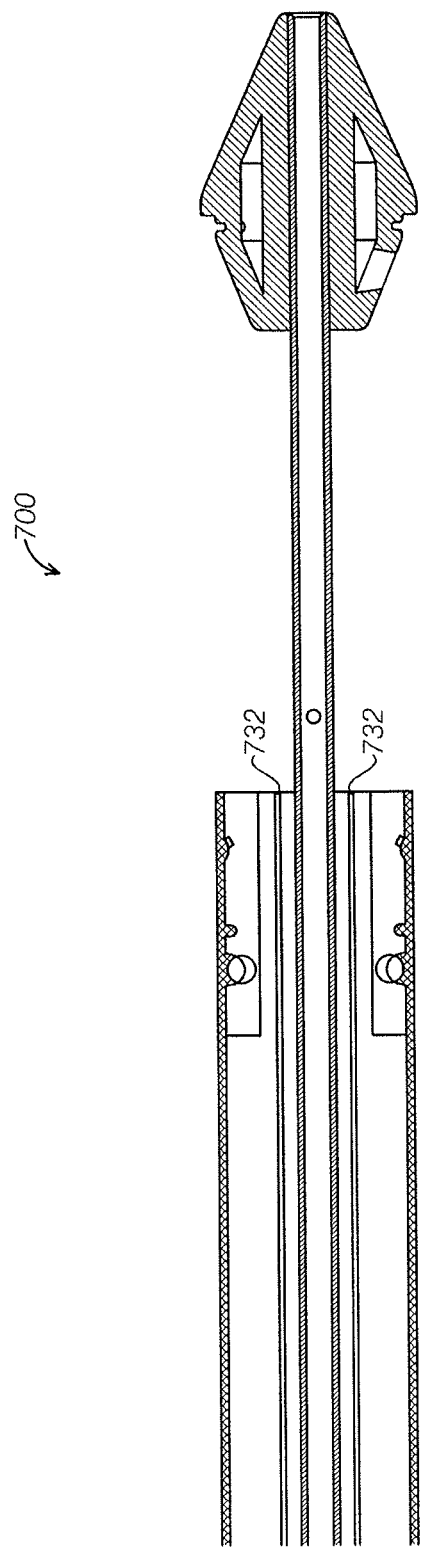
FIG. 13C shows a close up of the cross-section of the distal end of the unsheathed device of FIG. 13A where a series of hypotubes have advanced distally.

FIGS. 13A-13C show the delivery device 700 where the tether control lever 738 and thumbscrew 740 have been pushed distally. This distal movement moves the series of hypotubes 732 as well from a more proximal location to a more distal location along the central stem 718 such that the series of hypotubes 732 meet and abut the tether ends retainer 720. When doing so, the tether ends retainer 720 remains stationary in its position on the central stem 718. The hypotubes 732 aide with keeping the tethers separated when there is slack in the tether lines as they are moved forward during deployment or when the prosthetic valve is being loaded. Notes that the tether ends retainer 720 remains stationary in its position on the central stem 718. This places the prosthetic valve in an optimal location on the delivery device 700 for loading and deployment.

Referring to FIG. 12A, the handle portion 709 also includes an inner sheath control knob 752 which is coupled to a lead screw 750. These two components work to extend or retract the inner sheath 716. Sitting on the proximal side of the sheath control knob 752 is a clip 754 that prevents the inner sheath 716 from retracting too proximally until the prosthetic valve is ready to fully deploy, at which time the clip 754 may be pulled off.

In use, a prosthetic valve is first loaded into the device 700. FIG. 20A shows the loading of an exemplary mitral valve prosthesis 790. The prosthesis valve 790 generally has a cage-like appearance with a center aperture 793. The prosthetic valve 790 includes a proximal end petals 791 and distal end petals 792. In this embodiment, the mitral valve prosthesis includes two anchors having a series of cells with radially extending petals or loops. To load the prosthetic valve into the delivery device 700, the central stem 718 and nosecone 706 are first inserted through the center aperture 793 of the prosthetic valve. Next, individual lengths of tether 76 from a series of tethers originating from the device proximal end 702 and disposed around the central stem 718 portion, loop around each petal portion from the proximal end of the prosthetic valve (the end closer to the proximal end of the delivery device). While not all of the petals from the proximal end of the prosthetic valve need to be coupled to an individual tether, enough petals should be coupled to individual tethers such that when the series of tethers are pulled axially in the proximal direction, all the petals of the proximal end of the prosthetic valve will uncurl equally and evenly, and close in around the central stem 718. Then the free ends of the tether 726 having the truncated cones may be slipped into corresponding pockets 724 of the tether retainer 720.

After tensioning the tethers/sutures and pulling the proximal side petals of the prosthetic valve straight using the tether control lever 738, the inner sheath 716 may be extended distally with the sheath control knob 752 such that it begins to cover the straightened out proximal side petals of the prosthetic valve. Further retracting the tether retainer 720 will cause the tensioning forces to translate to other parts of the prosthetic valve. This additional tension is now able to pull the distal side petals on the prosthetic valve towards the inner sheath 716. Recall that, at this point, the proximal end petals are already maintained within the inner sheath 716, so that further tension on the proximal end of the prosthetic valve will now straighten out the distal petals of the prosthetic valve. Once the distal end petals of the prosthetic valve are completely retained within the inner sheath 716, then the delivery device 700 is fully loaded. The inner sheath 716 may be extended fully distally until it meets with nosecone 706. This can be done by rotating a sheath control knob 752. Rotating the sheath control knob 752 in one direction will extend the inner sheath 716 until it meets up with the nosecone 706, while rotating the sheath control knob 752 in the opposite direction will retract the inner sheath 716 proximally along the elongated portion 701 of the delivery device 700.

An outer or atrial access sheath may be used to assist with delivery of the device 700 transatrially. Thus, the delivery device 700 includes an outer sheath 712, which can be seen in FIGS. 12A-12C. FIG. 12A is a schematic of the delivery device 700. FIG. 12B shows a cross-section of the delivery device 700 along a longitudinal plane and FIG. 12C shows a close-up of the cross-section for the distal end of the delivery device 700. FIG. 12A shows the outer sheath 712 relative to the inner sheath 716. The outer sheath 712 is primarily used during insertion of the delivery device 700 into a patient's body cavity. The outer sheath 712 is slideable along the elongated portion 701 to cover the elongated portion 701 up to the nosecone 706. Once an incision is made, a suture is purse string stitched around the perimeter of the incision. This allows the incision to be made smaller by pulling on the (purse string stitched) suture. As can be seen from FIG. 12A, the outer sheath 712 includes an outer sheath groove 714 disposed around its distal end. The incision may be cinched down around the outer sheath groove 714 such that the incision site is essentially closed off except for the delivery device 700. This is advantageous because it minimizes exposing a patient's internal system to the outside environment thereby reducing risk of harmful agents coming into contact with a patient's internal system. In addition, having the incision site cinched around the delivery device 100 also reduced the amount of blood loss during the procedure.

Because the outer sheath 712 is configured to move axially with respect to the remainder of the delivery device 700, an operator will still be able to maneuver the delivery device 700 within the incision site axially and also to some extent in a circular fashion within the incision site for finding optimal position to deploy the prosthetic valve. Thus the outer sheath 712 remains stationary once the incision site sutures have been tightened around the outer sheath groove 714, and the delivery device 700 is able to deliver the prosthetic valve with use components of the delivery device that are further described below.

Using the sheath 712, the operator may position the device distal end 704 in the proper location within the patient's heart. Once the operator is satisfied with the location of the device distal end 704, the sheath control knob 752 can be rotated to pull the sheath 716 proximally and expose the distal end petals of the prosthetic valve. FIGS. 13A and 13B show the inner sheath 716 retracted, which would expose the distal end of the valve (allowing it to expand) and expose the collapsed proximal end of the valve (held in the collapsed configuration by the tethers).

To expand the proximal end of the valve, the tether control lock 734 is unlocked so that the operator may begin to adjust the tether control lever 738. By pushing the tether control lever 738, tension on the tethers is lessened. The reduced tension on the tethers in combination with the inner sheath 716 being retracted, allow the series of proximal petals on the prosthetic valve to curl back into their natural shape for positioning. Advantageously, at this point, if the operator decides that the proximal anchor and/or the entire valve has not been positioned as desired, the tethers can be tightened again, causing the proximal anchor to collapse. The inner sheath can then be advanced, fully covering the valve and allowing it to be either repositioned or removed entirely.

Figure 14:
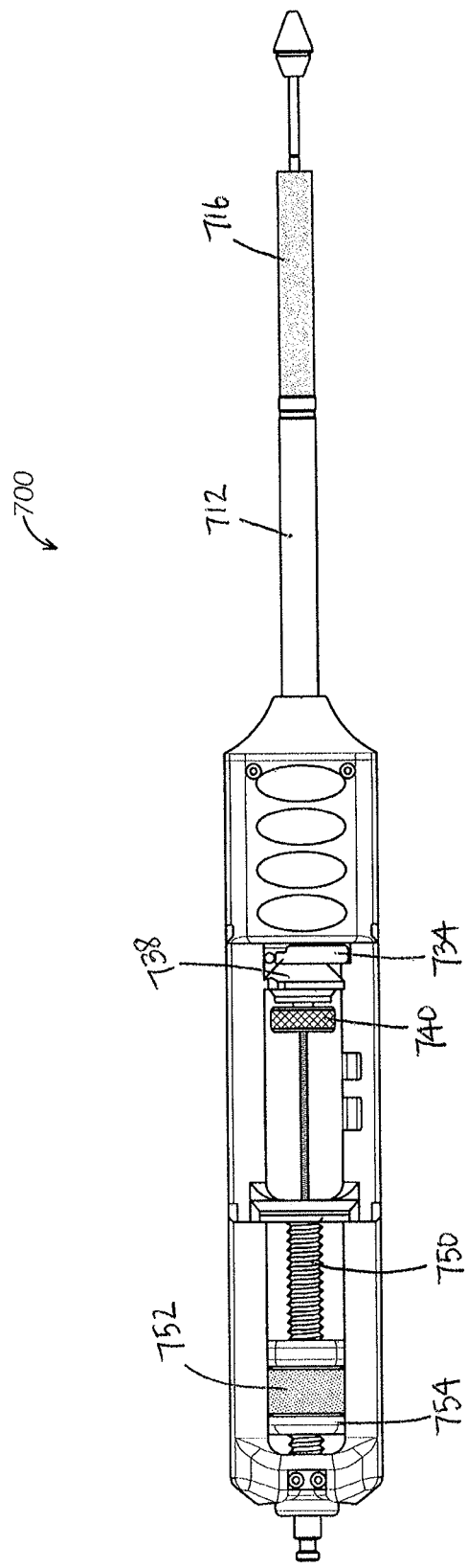
FIG. 14 shows the delivery device of FIG. 11A where a clip maintaining tether tension has been removed.
Figure 15A:
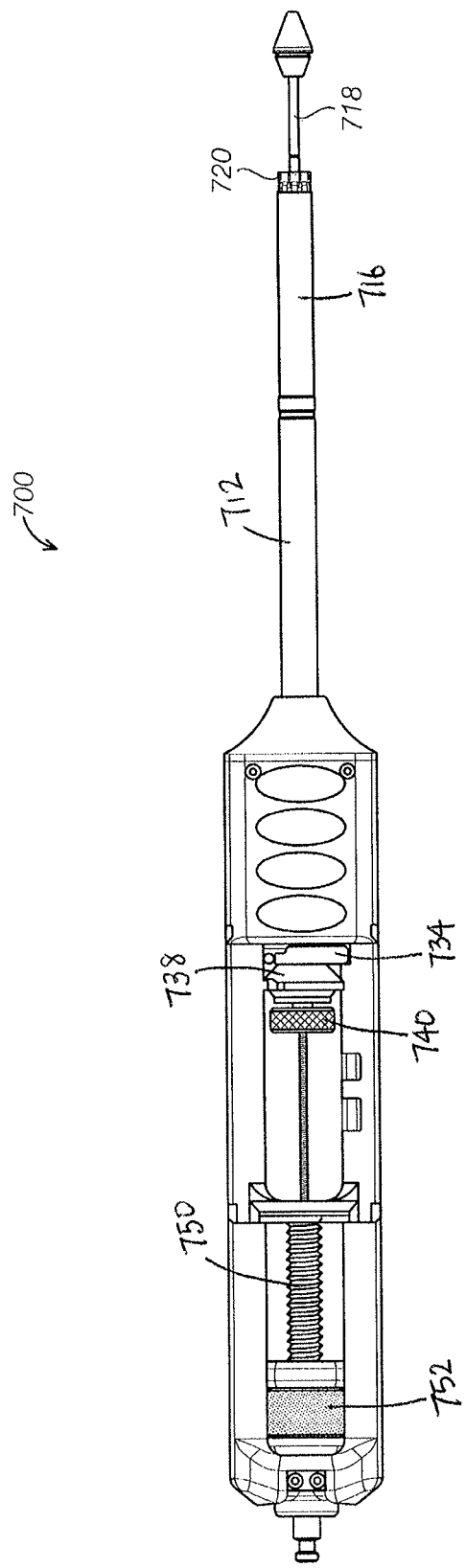
FIG. 15A shows the delivery device of FIG. 11A where a tether ends holder near the distal end is exposed, and tether ends are able to release.
Figure 15B:
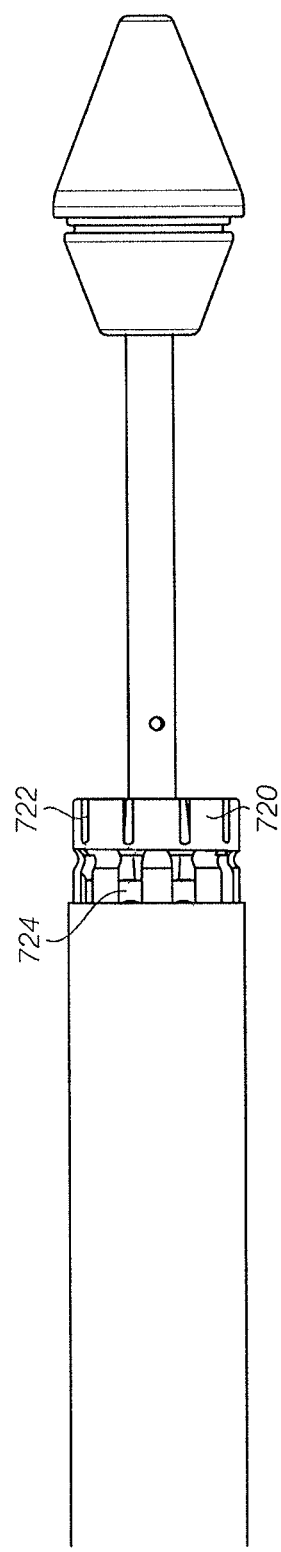
FIG. 15B shows a close-up of the tether ends retainer of FIG. 15A.

Once the positioning of the valve is finalized, the operator can release the valve from the delivery device 700. Referring to FIG. 14, to do so, the clip 754 disposed at the end of a lead screw 750 (shown in FIG. 12A) until now, has function to prevent the inner sheath 716 from retracting too far, may be removed. As shown in FIGS. 15A-15B, this allows the sheath control knob 752 to travel further toward the device proximal end 702 for releasing the tether ends (FIG. 14). Specifically, the clip 754 may be removed to allow the inner sheath 716 to retract to the farthest proximal position possible. Once at the inner sheath 716 is at the farthest proximal position, the tether retaining pockets 724 become exposed, and without the inner sheath 716 to maintain the tether ends within the pockets 724, the proximal tether ends are allowed to pop out of their respective pockets 724 and the proximal side of the prosthetic valve is able to deploy.

Now the entire prosthetic valve has been deployed and the delivery device may be removed. The outer sheath 712 can remain coupled to the incision site thought the outer sheath groove 714 and the purse-string suture. However, once the purse-string sutures are removed, then the entire delivery device may be removed.

In some embodiments, an operator may desire an alternative or additional method for removing the tethers from the proximal anchor (e.g., if the tethers get caught in the anchor and/or don't pop out of the pockets).

Referring to FIGS. 11A and 17, the thumbscrew 740 of clamping mechanism 771 can act as a secondary release mechanism to provide an alternative method of releasing the tethers if the tethers become tangled or fouled up during prosthetic valve loading or deployment. As FIG. 17 shows, the tethers are threaded through the tether control lever 738 past a washer or cushion before travelling distally to where the distal ends will loop around the prosthetic valve. As can be seen in FIG. 17, the thumbscrew 740 is screwed down against the washer or cushion to maintain tension on the proximal end of the tethers. To use the thumbscrew 740, the operator rotates the knob 740 in the direction that reduces the force on the washer/cushion, thereby releasing tension on the tether ends against a washer. Because there is no need to adjust the thumbscrew 740 unless the operator needs to adjust tangled or stuck tethers, the thumbscrew 740 may be color coated a different color (i.e. red) to alert the operator that this knob should not be adjusted unless absolutely necessary to prevent the operator from inadvertently releasing the tether ends prior to fully loading the prosthetic valve or accidentally deploying the prosthetic valve prior to finding an optimal position for the valve.

Figure 18A:
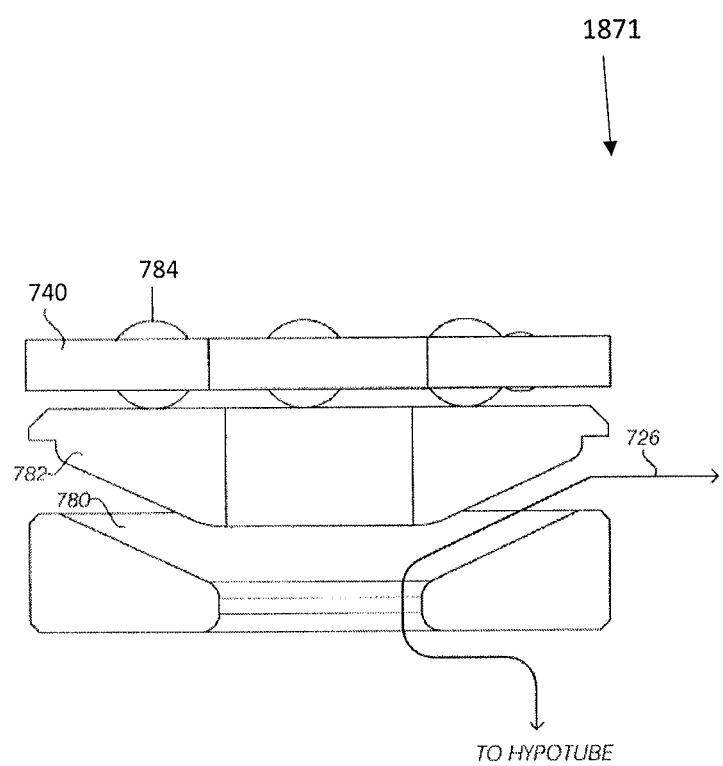
FIG. 18A shows an alternative embodiment of the proximal tether control and retaining feature having a truncated conical washer.
Figure 18B:
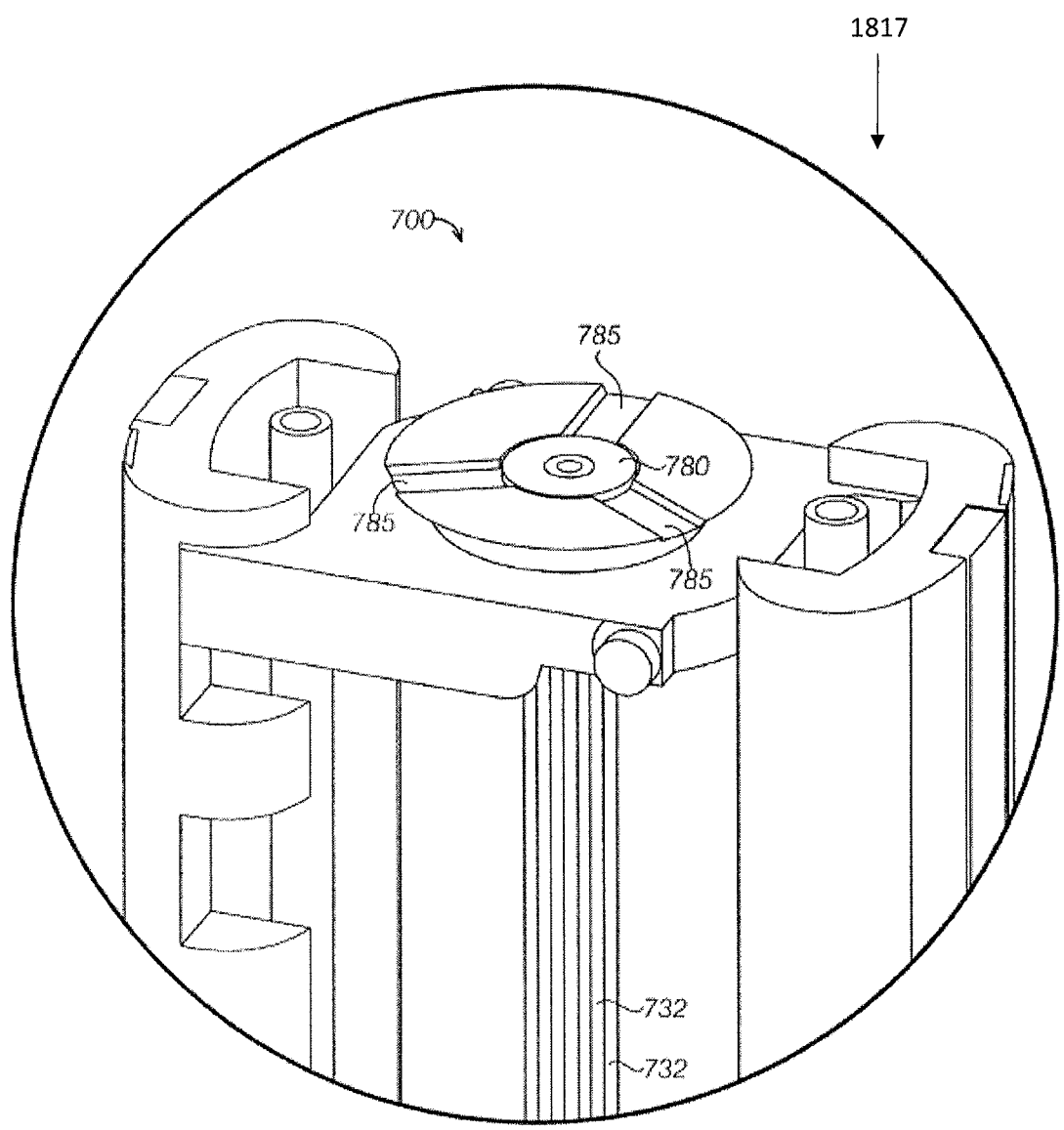
FIG. 18B shows a top portion of the truncated conical washer of FIG. 18A having three channels.

An alternative embodiment of a clamping mechanism 1871 is shown in FIGS. 18A and B. Here, a truncated cone 782 and corresponding funnel-shaped washer 780 apply tension to the proximal tether ends. The path that the tether ends take in this configuration has a much more natural angle compared to the approximately ninety degree angle jog that the proximal tether ends must take in the prior configuration described (FIG. 17). In this example, the tethers or sutures are threaded three each into each of the three channels 785. In this alternative configuration, a thrust bearing 784 is used to prevent rotation of the washer 780 when threading the thumb screw 740. In the absence of this feature, when the thumb screw 740 is rotated with a certain amount of force on the tethers 726 and potentially twist the tethers 726 together which could lead to difficulty adjusting the tension on the tethers.

Figure 40A:
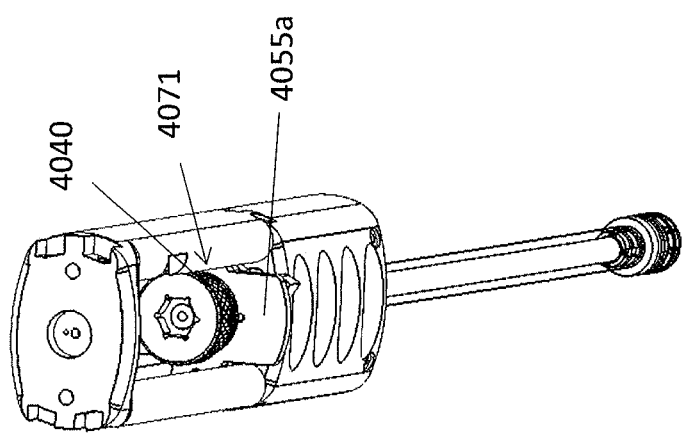

Another alternate tether clamping mechanism 4071 is shown in FIGS. 40A-40B. The secondary release mechanism 4040 can include a thumbscrew 4040 around which the tethers are wound. Two large washers 4055a,b can be positioned so as to pinch the tethers therebetween (and against the thumbscrew 4040). The washers 4055a,b can be slightly enlarged relative to the thumbscrew 4040 (and/or relative to the washers of FIG. 17). The larger washers 4055a,b advantageously provide more surface area with which to clamp the tethers (and therefore more friction), direct visualization during assembly to void overlaps, twists, and/or misrouting, and controller and visually confirmable washer separation to improve tether release in case of bailout. When the thumbscrew 4040 is rotated, the washers 4055a,b can pull apart slightly, thereby releasing the proximal ends of the tethers. Further, when thumbscrew 4040 is rotated, the washers 4055a,b can be lifted apart one by one to ensure separation (the tension in the tethers may otherwise keep the thumbscrews together). Stepped features in the thumbscrew shaft can further interact with the geometry of the large washers 4055a,b to ensure this separation.

In some embodiments, rather than including a clamping mechanism as part of the handle, a mini clamp mechanism can be used at the distal end of the delivery device. That is, referring to FIGS. 43A-43C, a delivery device 4300 can include a mini clamp mechanism 4343 at the distal end of the delivery system 4300 (e.g., just proximal to the tether retainer 4320). The mini clamp mechanism 4343 includes a set of washers 4345 around which the proximal ends of the tethers are wound and clamped between. The washers 4345 can be sandwiched between a screw and nut. Further, the nut can be connected to the tube 4356, which rotates and slides axially relative to the washers 4345. As the tube 4356 rotates, it unscrew the nut to pull the washers 4345 apart. An outer tube 4346 is rotationally fixed via flanges in the handle.

A thumbscrew 4340 at the proximal end of the handle 4309 can be rotated to rotate the tube 4346 and nut 4449, which can loosen the washers 4355, thereby releasing the tethers (i.e., for use as a primary or secondary release mechanism). In some embodiments, the distal features on the tethers can be configured to remain within the tether retainer when the tethers are released.

Figure 44A:
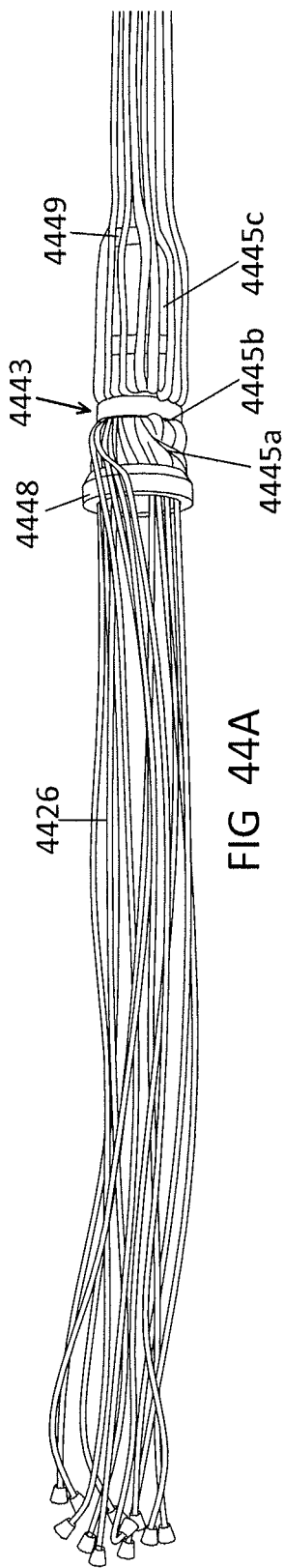
FIGS. 44A-44C show tethers looped around washers of a mini clamp mechanism.
Figure 44B:
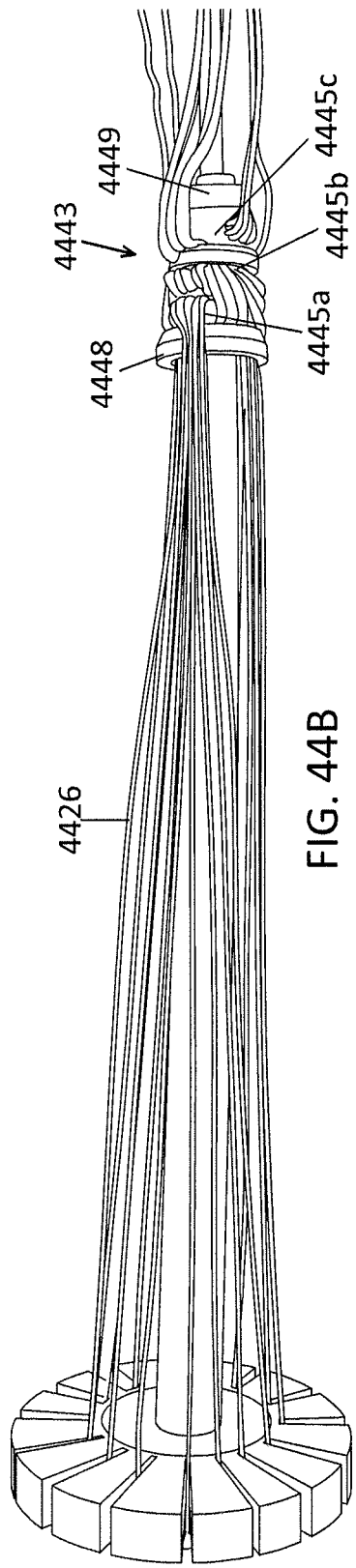
Figure 44C:
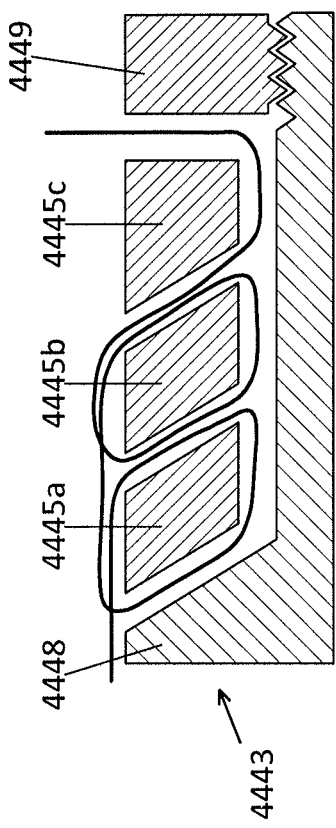

As shown in FIGS. 44A-44C, the proximal ends of the tethers 4426 of a mini clamp mechanism 4443 can be looped around the washers 4445a-c (e.g., such that a tether 4426 completely circles around each of the washers 4445a-f in the axial directions). Further, the washers 4445a-f can be conical, which can advantageously increase the friction force in holding the tethers 4426 therebetween. Some or all of the washers 4445a-f can include one or more alignment features 4448 within which the tethers 4426 can sit to protect the tethers 4426 from damage during clamping. As described with respect to mini camp mechanism 4443, the washers 4445 of mini clamp mechanism 4443 can be sandwiched between a screw 4448 and nut 4449. When the screw 4448 and nut 4449 are rotated relative to one another (e.g., due to activation of a thumbscrew on the handle), the nut 4449 and screw 4448 can move apart from one another, loosening the washers 4445 and allowing the tethers 4426 to be removed.

Figure 45A:
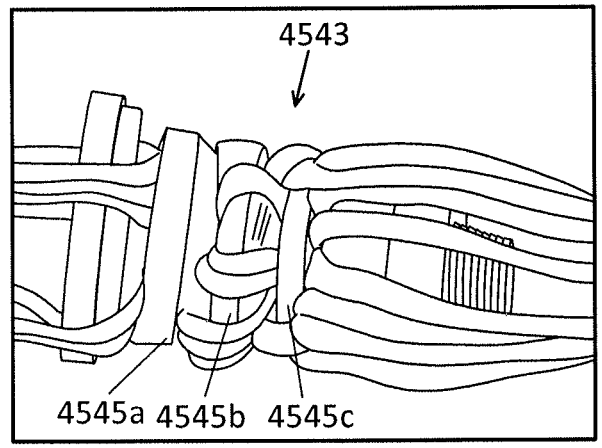
FIGS. 45A-45B show tethers woven around washers of a mini clamp mechanism.
Figure 45B:
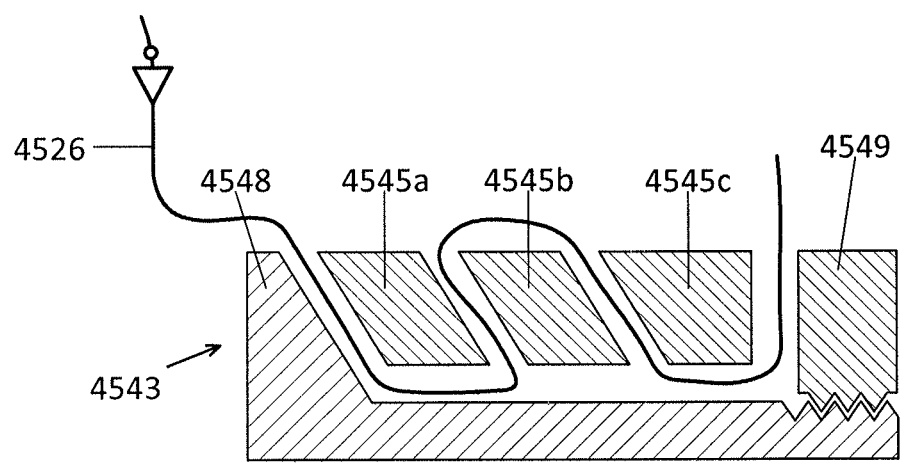

As shown in FIGS. 45A-45B, proximal ends of the tethers 4526 of the mini clamp mechanism 4543 can be woven around the washers 4545a-c rather than looped.

In some embodiments, the mini clamp mechanisms described with respect to FIGS. 43A-45B can be positioned just proximal of the tip of the elongate body with just enough space to move through actuation without interfering with other components.

Advantageously, the mini clamp mechanisms described with respect to FIGS. 43A-45B allow the tethers to be shorter, as they only need extend from the distal mini clamp mechanism, through the valve, and into the tether retainer (as opposed to extending all the way from the handle). As a result, there is less tether to pull out when released (e.g., through a secondary release mechanism). Further, the mini clamp mechanisms can be separately manufactured and then inserted into the rest of the delivery device, easing manufacturing. Additionally, having shorter tethers the extend only at the distal end of the device allows a plug or sealing mechanism to be put near the distal end of the device (just proximal of the tethers), thereby helping to prevent leakage of fluid into the device. Further, having shorter tethers minimizes the impact of tether material stretch, which may otherwise compromise precise prosthesis placement. In some embodiments, the tethers can be between 2-4 inches in length, such as 2.5-3.5 inches in length, such as approximately 3.3 inches in length.

Alternative designs for reducing the tether length are described with respect to FIGS. 48 and 36-38.

Figure 48A:
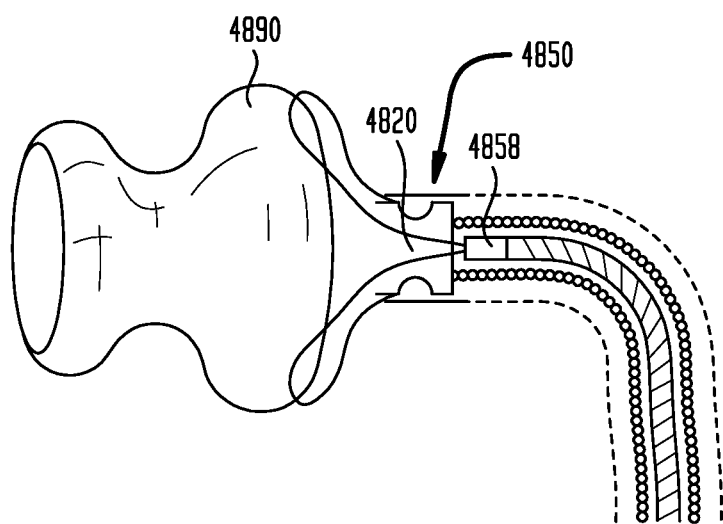
FIGS. 48A-48D show a delivery device including a crimping mechanism.
Figure 48B:
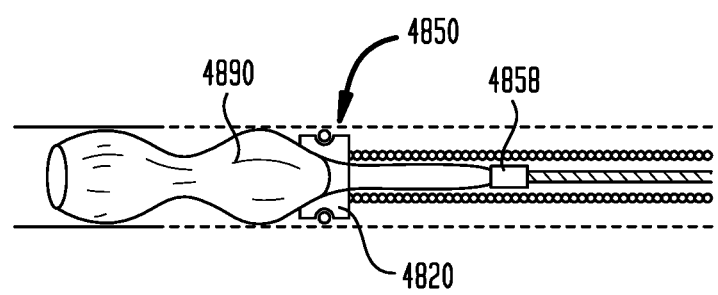
Figure 48C:
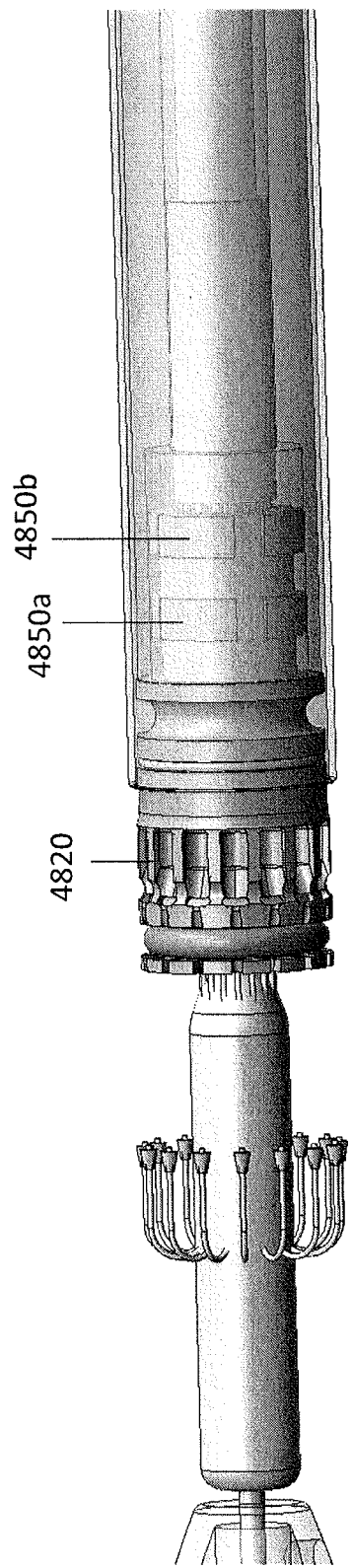
Figure 48D:
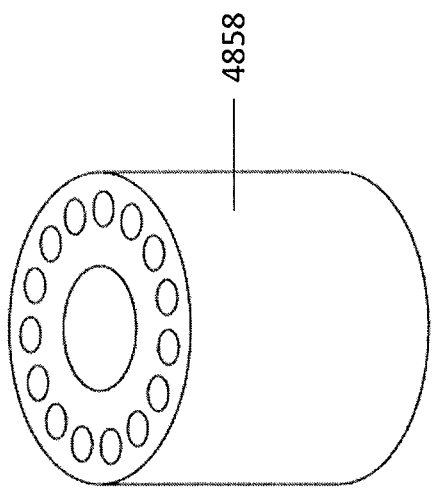
Figure 49A:
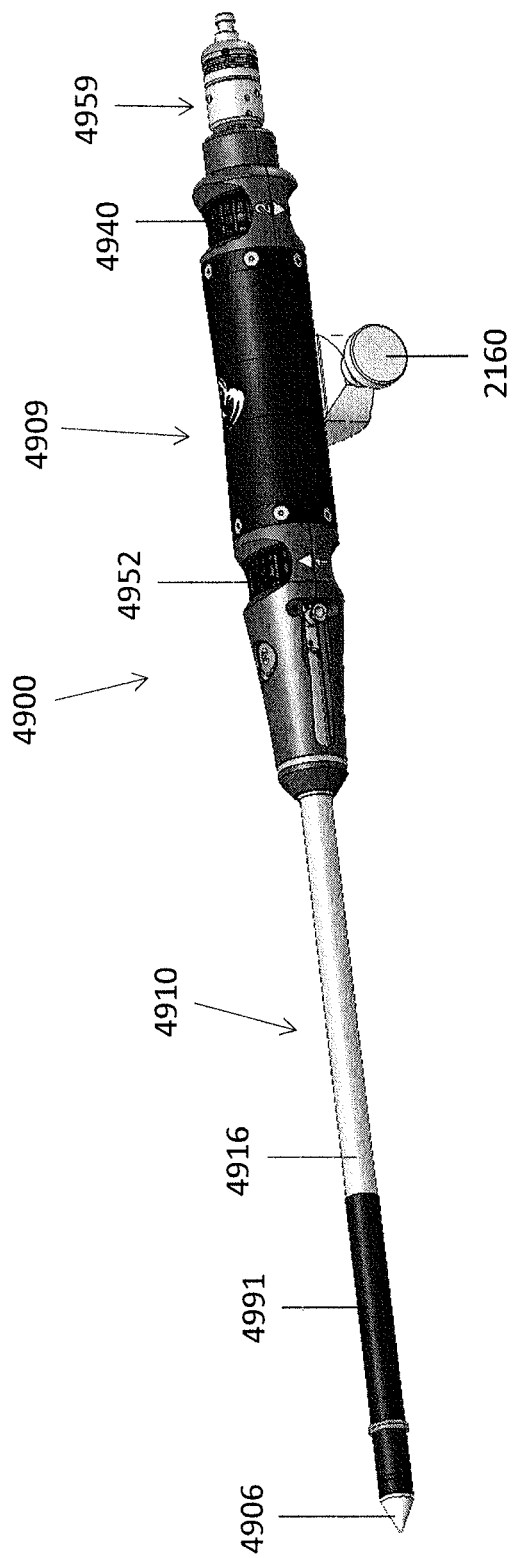
FIGS. 49A-49D show another exemplary delivery device including a crimping mechanism.
Figure 49B:
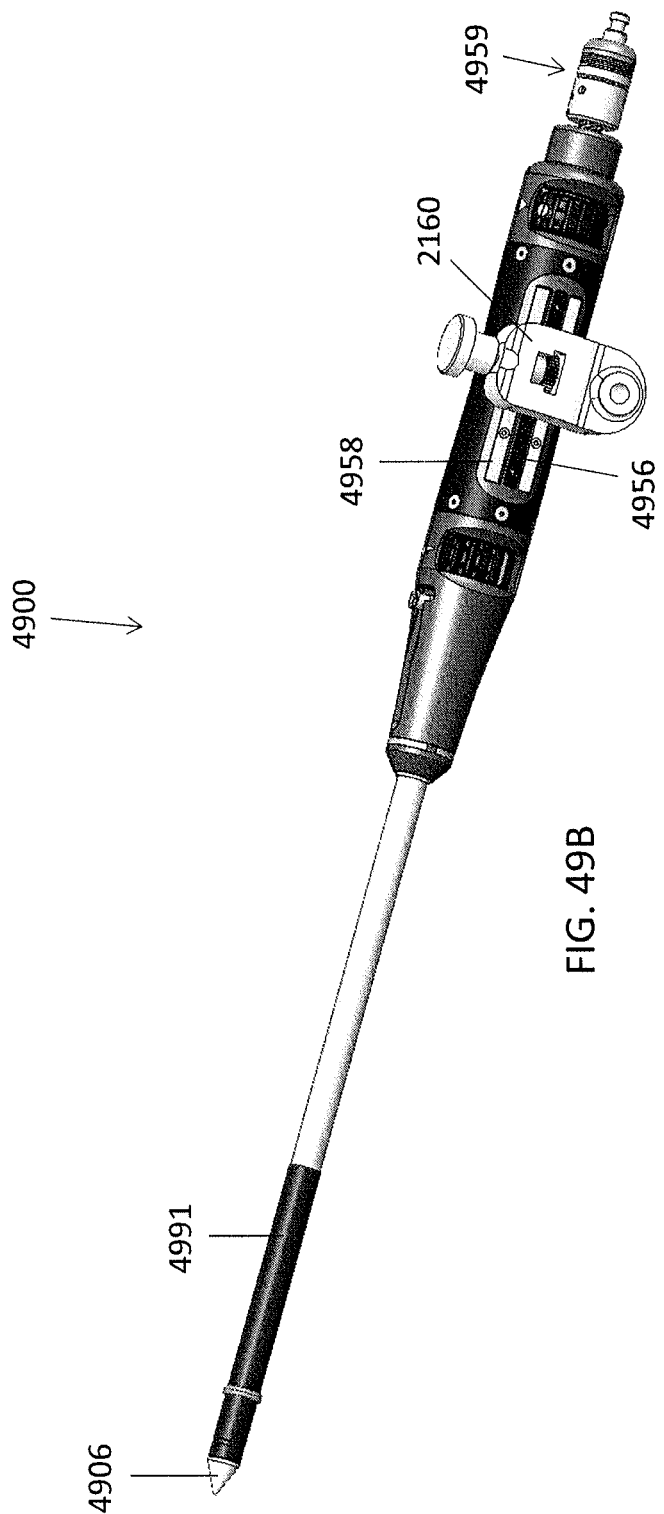
Figure 49C:
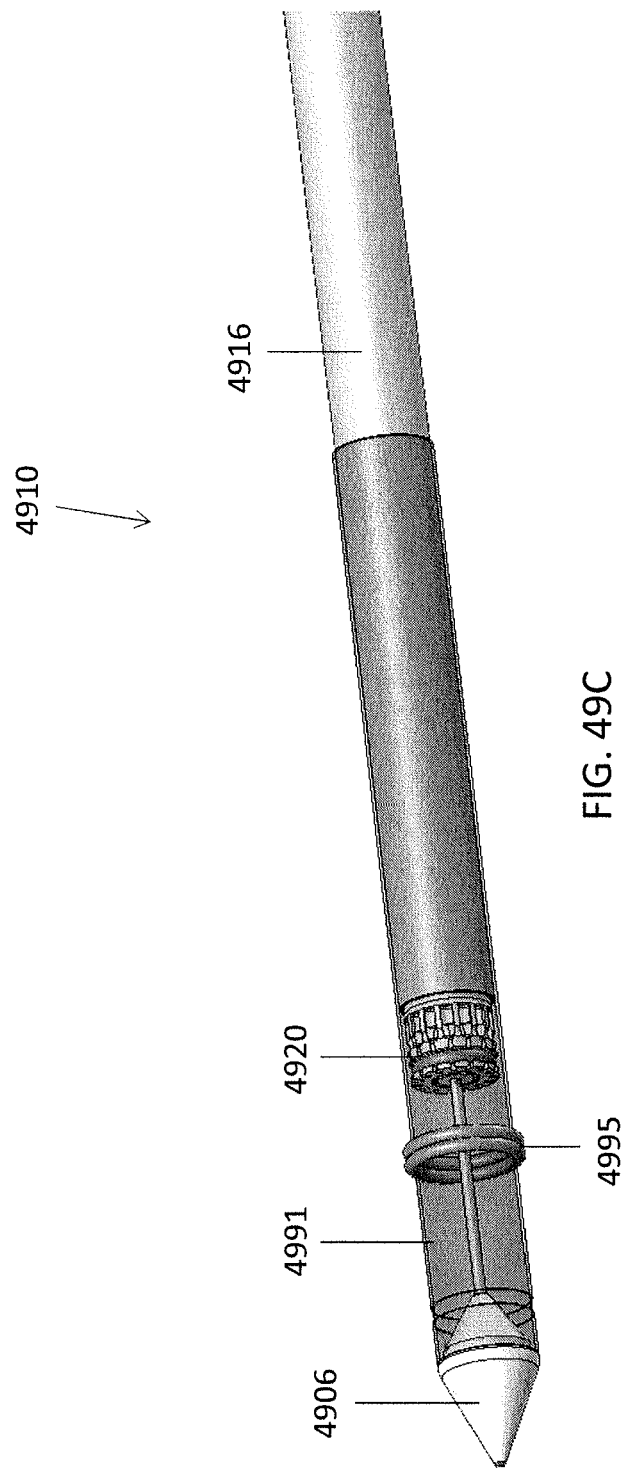
Figure 49D:
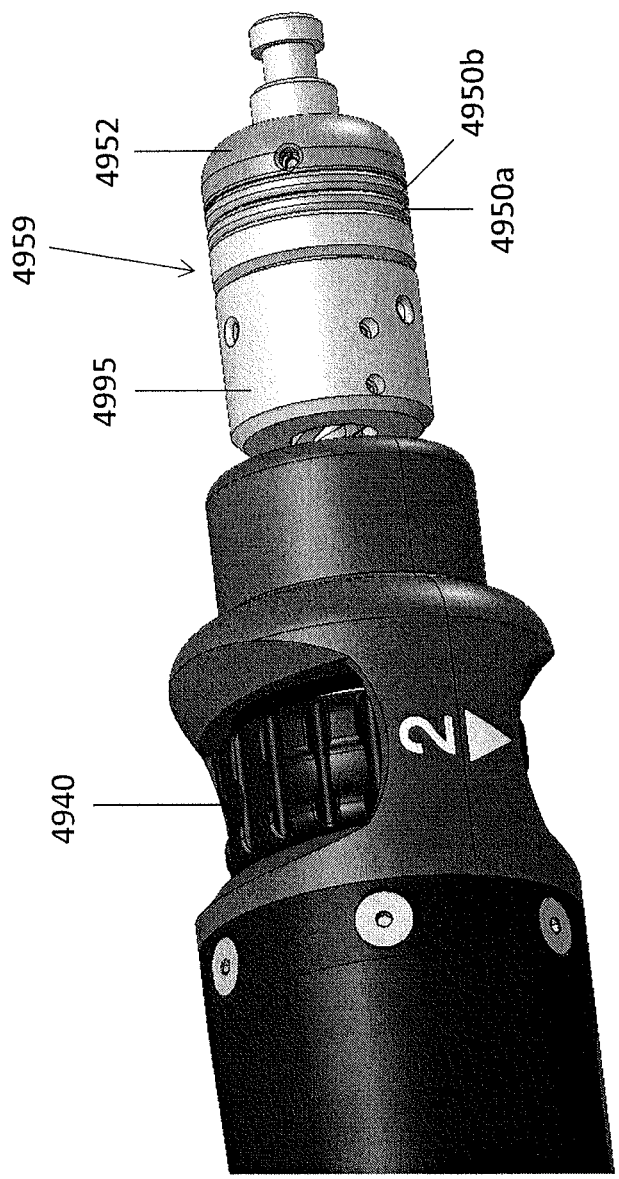

In one embodiment, a crimping mechanism can be used in place of a mini clamp mechanism. Referring to FIGS. 48A-48D, one or more crimps 4858 can be used to hold the proximal ends of the tethers. The crimps 4858 can be positioned at the distal end of the delivery device (i.e., in the distal assembly 4850) just proximal of the tether retainer 4820. In some embodiments, the crimps 4858 can have holes therein to house each tether such that only one crimp fitting is required (as shown in FIG. 48D). In other embodiments, each individual tether can be crimped. In use, the crimps 4858, when constrained in a housing (as shown in FIG. 46N) can be actuated a rigid actuation tube and/or cable, which can be translated by rotating with the knob shown in 46P and 46Q. Using crimps advantageously allows for the use of shorter tethers, improved length control between the proximal and distal features of the tether, decreased assembly time, and higher retention force than for clamping mechanisms.

In some embodiments, when crimps are used, cutting of the tethers can be used as a secondary release mechanism. Such cutting is described in PCT Application No. PCT/US17/37850, filed Jun. 16, 2017, the entirety of which is incorporated by reference herein.

In another embodiment, as shown in FIG. 36, the tethers 3626 can be attached at their proximal end to a movable mandrel 3623 that can extend, for example, substantially all the way to the distal end of the shaft. In such an embodiment, the distal tether retainer 3620 can be moved further proximally (away from the distal end) relative to other embodiments. In use, the mandrel 3623 can then be used to pull proximally on the tethers (e.g., for removal).

In another embodiment, as shown in FIGS. 37A-B, the tethers 3726 can have a bead 3780a,b on both the proximal end and the distal end thereof. The distal end 3780a can be configured to sit within a tether retainer 3720 (as described elsewhere herein), while the proximal end 3780a can likewise be configured to sit within a second tether retainer 3733 that is positioned mid-way along the shaft.

Figure 38A:
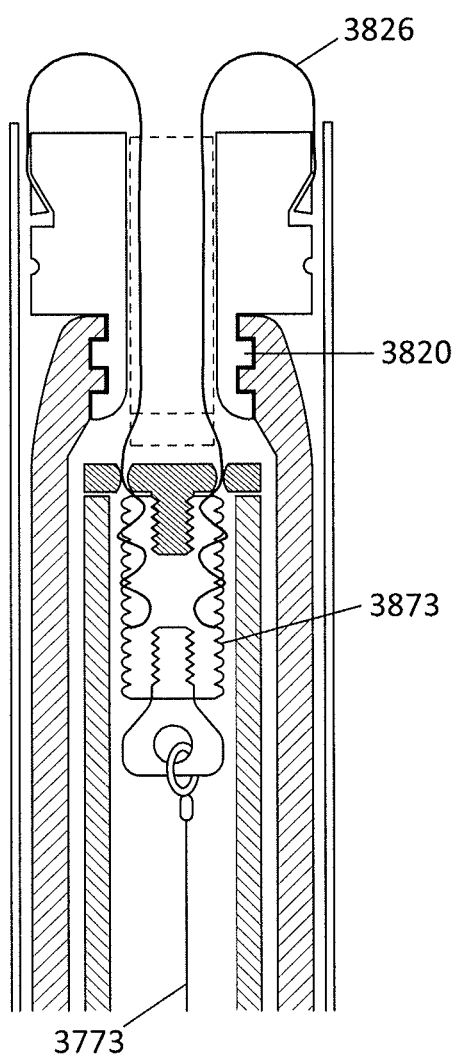
FIGS. 38A-38B show an exemplary delivery device in which the proximal ends of the tethers are held between coils of a spring.
Figure 38B:
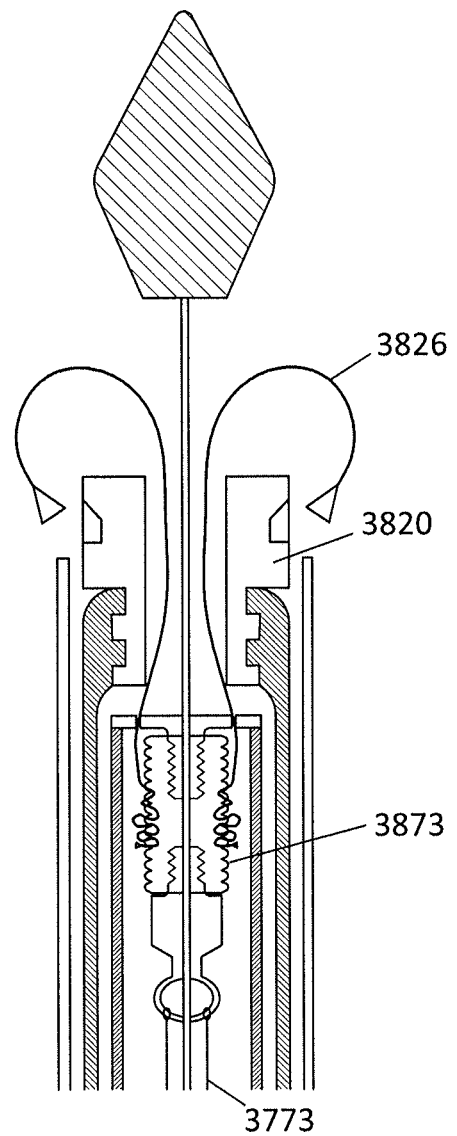

In another embodiment, as shown in FIGS. 38A-38B, in some embodiments, the proximal ends of the tethers 3826 can be held between the coils of a tightly coiled spring 3837 positioned along the mid-shaft. An inner shaft or cable 3873 can be pulled proximally to lengthen the coils of the spring 3837 and thereby release the proximal ends of the tethers 3826.

Figure 19:
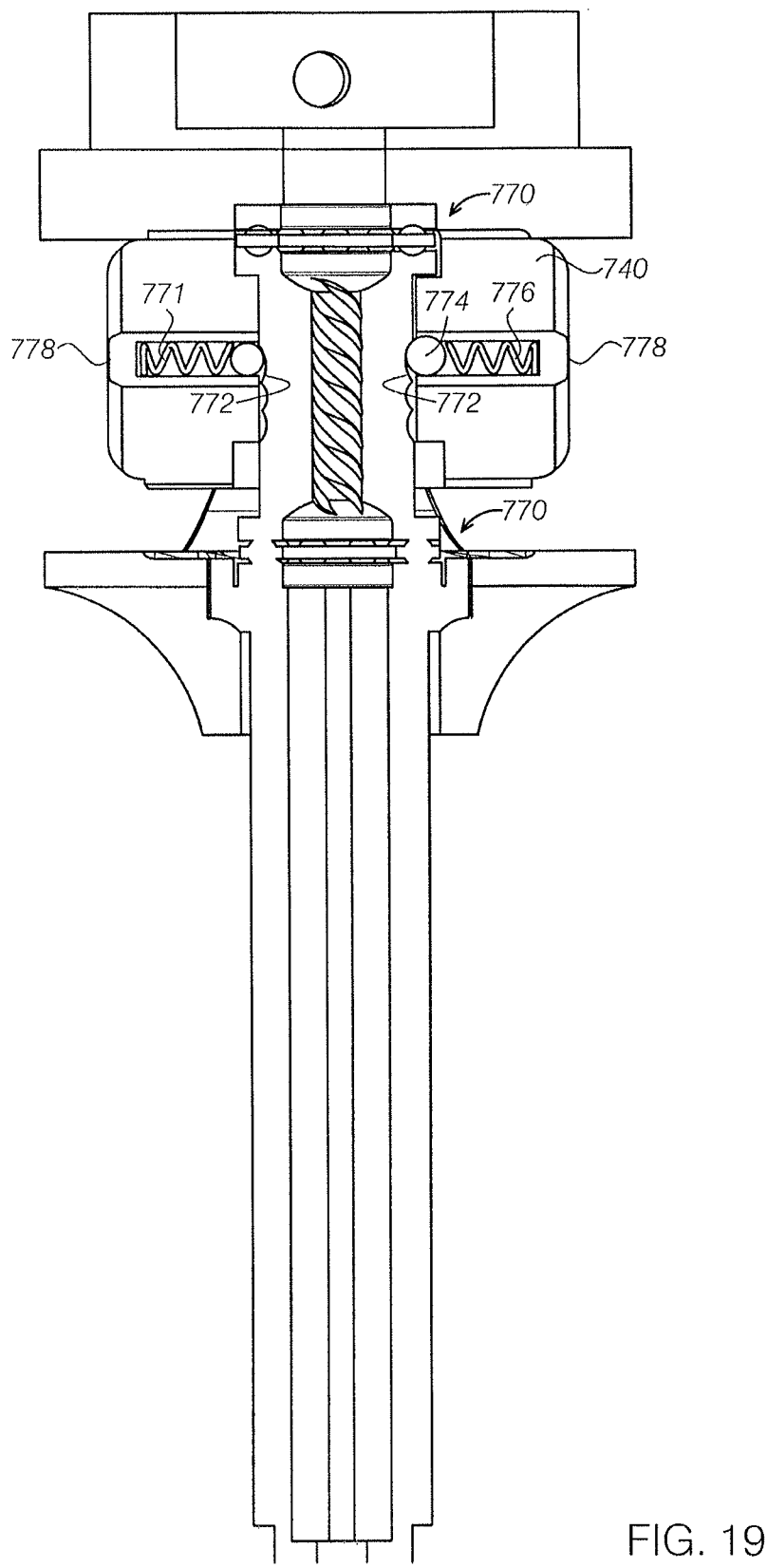
FIG. 19 shows a ratcheting system for maintaining the position of a tether control lever and a secondary release knob.

In some embodiments, the delivery devices described herein can a ratcheting mechanism for preventing back-driving (e.g. slippage) of the thumbscrew. A schematic of the ratcheting mechanism is shown in FIG. 19. FIG. 19 is a cross-section of the thumbscrew 740 (of device 700). The thumbscrew 740 includes a central stem 745 and a center screw 746. The central stem 745 includes internal features for accommodating the natural outer profile of the turns of the center screw 746. The center screw 746 includes a series of ratcheting teeth 770 at its proximal and distal end within the central stem 745. Disposed on two sides of the central stem 745 are a series of three indentations 772 on each of the sides. The thumbscrew 740 includes two channels 771 situated on opposite sides of each other (180 degrees apart). Within each channel 771 closest to the central stem 745 are identical ball bearings 774. Adjacent to each of the ball bearings 774 are two identical springs 776 and adjacent to the springs on their opposite side are two ratchet actuators 778. The ratcheting mechanism has three possible positions based on which well of the series of indentations 772 the ball bearing 774 is seated. When the ball bearing 774 is in the most proximal well, this places the ratchet mechanism in a position that prevents back-driving of the thumbscrew 740 and the tether control lever 738. When the ball bearing 774 is in the most distal well, this places the ratchet mechanism in a position that previews forward driving of the thumbscrew 740 and the tether control lever 738. Finally, when the ball bearing 774 is in the center position within the series of indentations 772, the thumbscrew 740 and the tether control lever 738 are free to move either distally or proximally along the axis of the center screw 746. In some examples, the operator will pull the actuators 778 to release tension against the ball bearing 774 and adjust the tether control knob 738 to move the ball bearing 776 between the three possible positions. In other examples, the ratchet actuator 778 has two positions. In a first position, the ratchet actuators 778 maintains a force against each ball bearing 774 through the springs 776 to keep ball bearing 776 within the desired indentation 772. In a second position, the operator is able to release the force the ratchet actuator 778 exerts upon the ball bearing 774 and by adjusting the thumbscrew 740, is able to transfer the ball bearing 774 into a different well within the series of indentations 25a772.

Figure 46A:
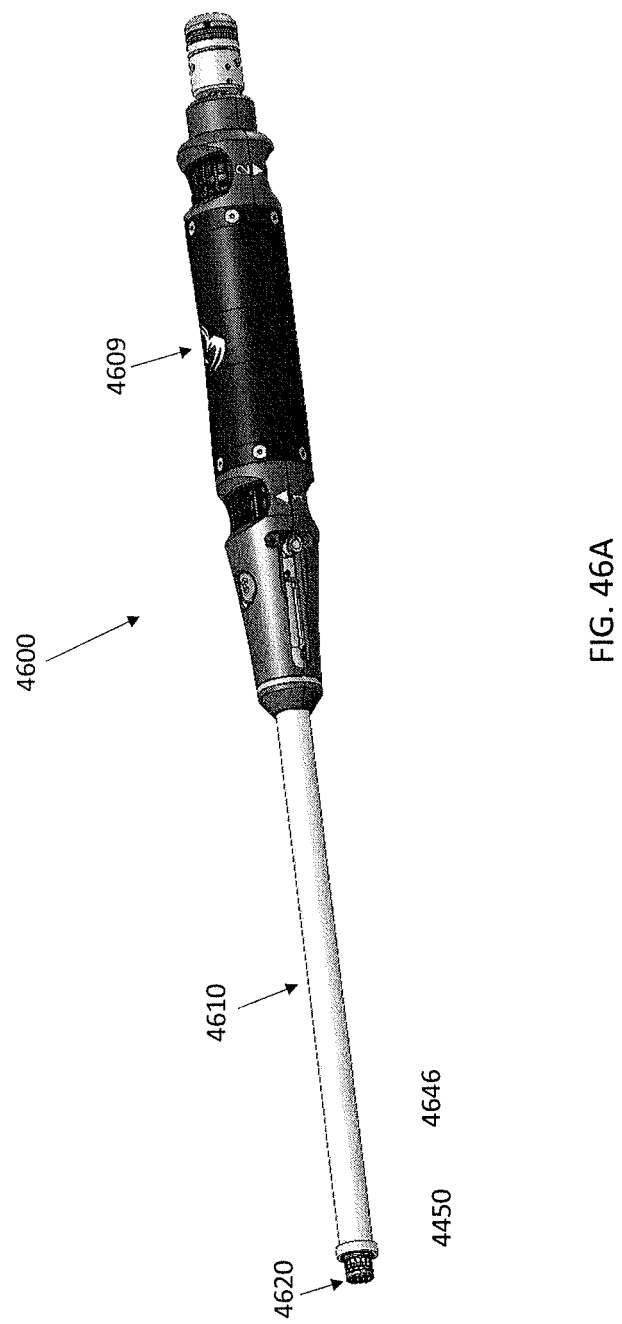
FIGS. 46A-46V show an exemplary delivery device configured to be used during a surgical method of delivery a valve.
Figure 46C:
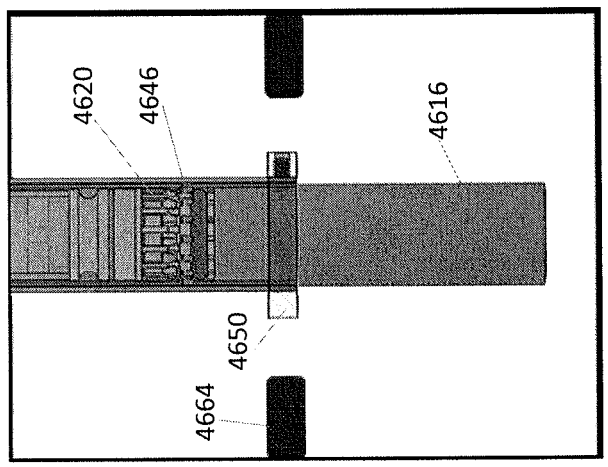
Figure 46B:
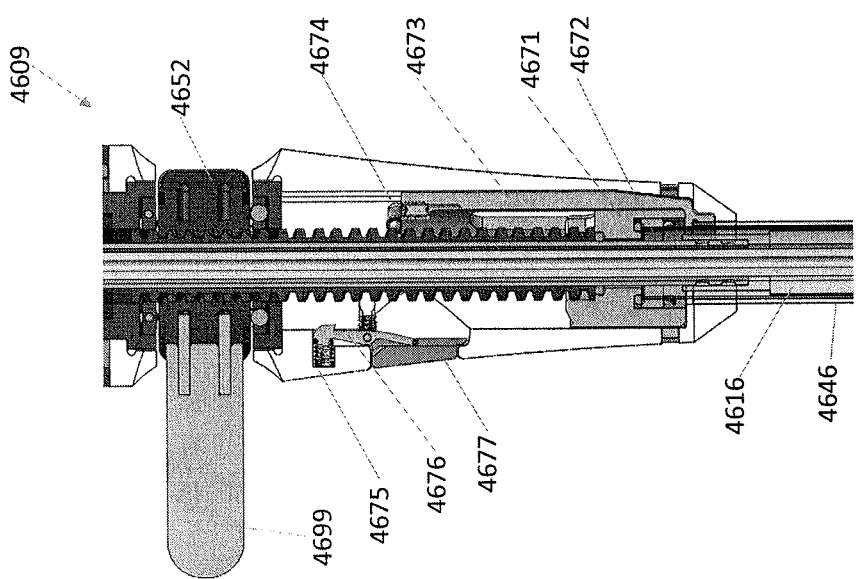
Figure 46F:
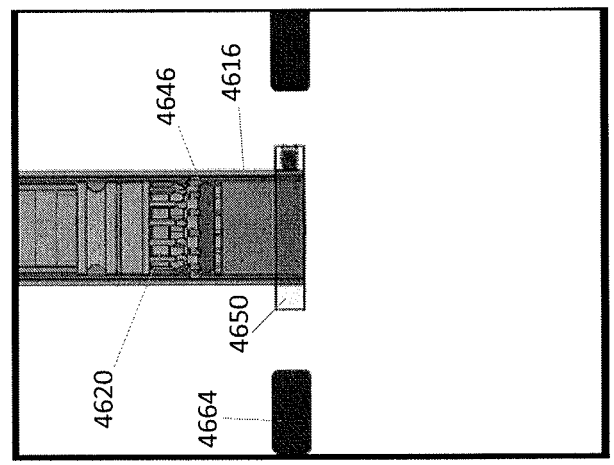
Figure 46E:
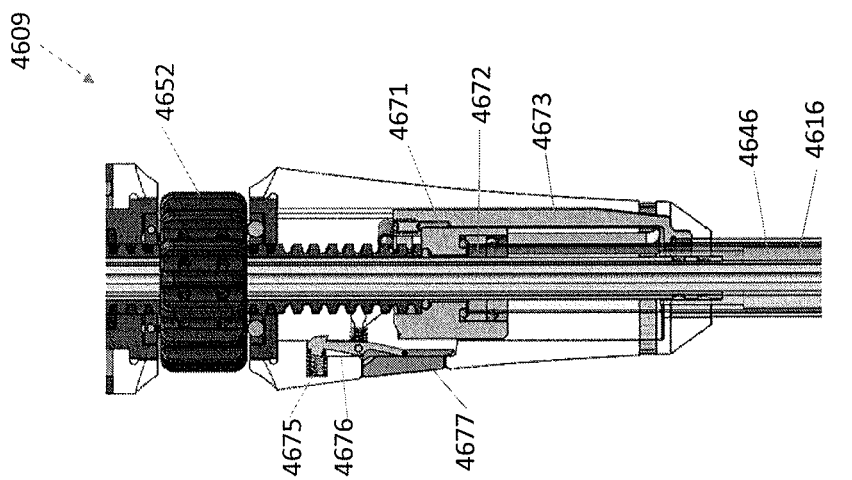
Figure 46D:
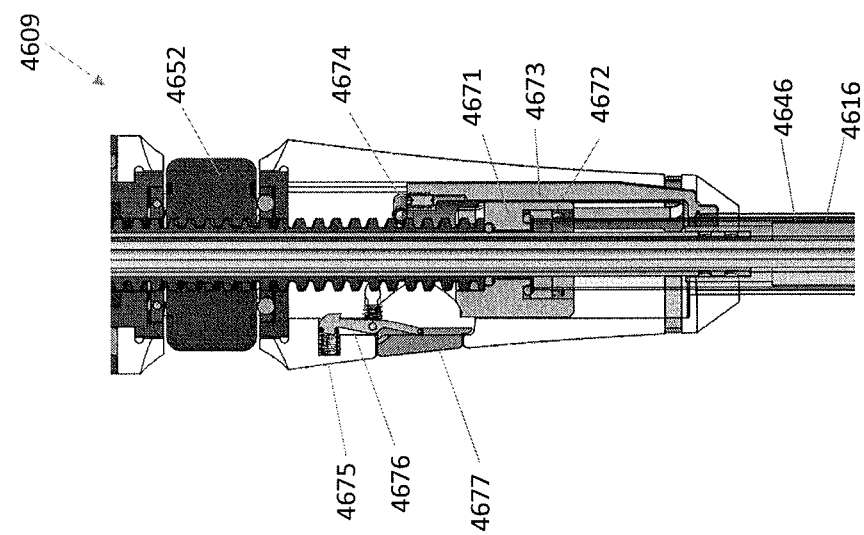
Figure 46I:
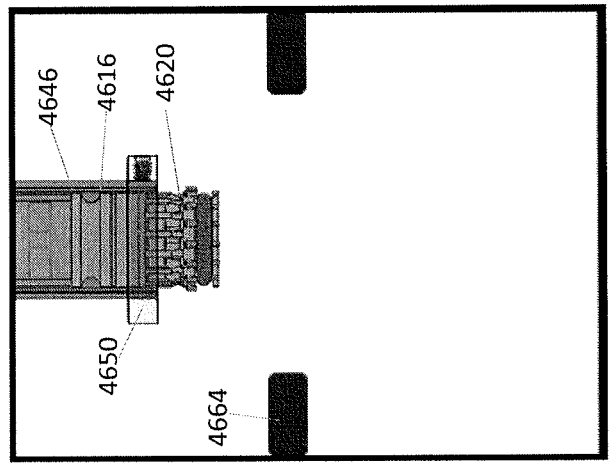
Figure 46H:
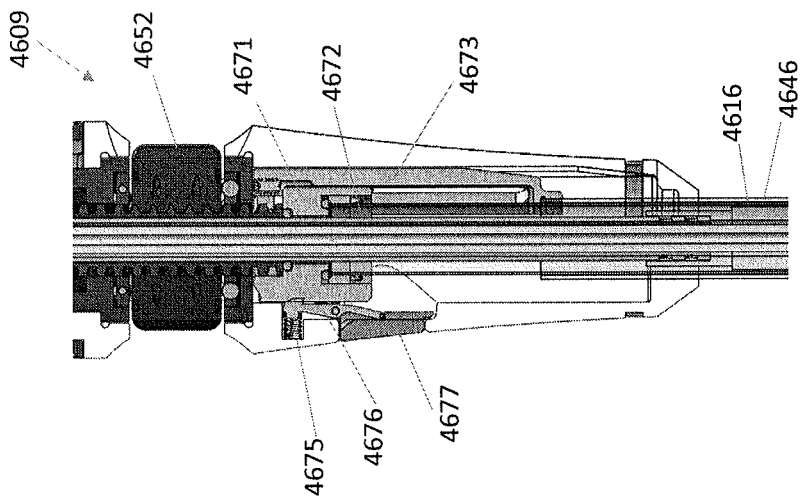
Figure 46G:
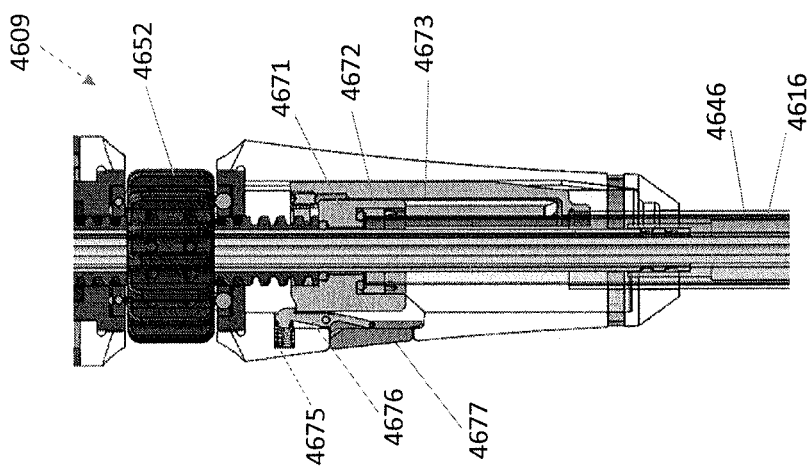
Figure 46O:
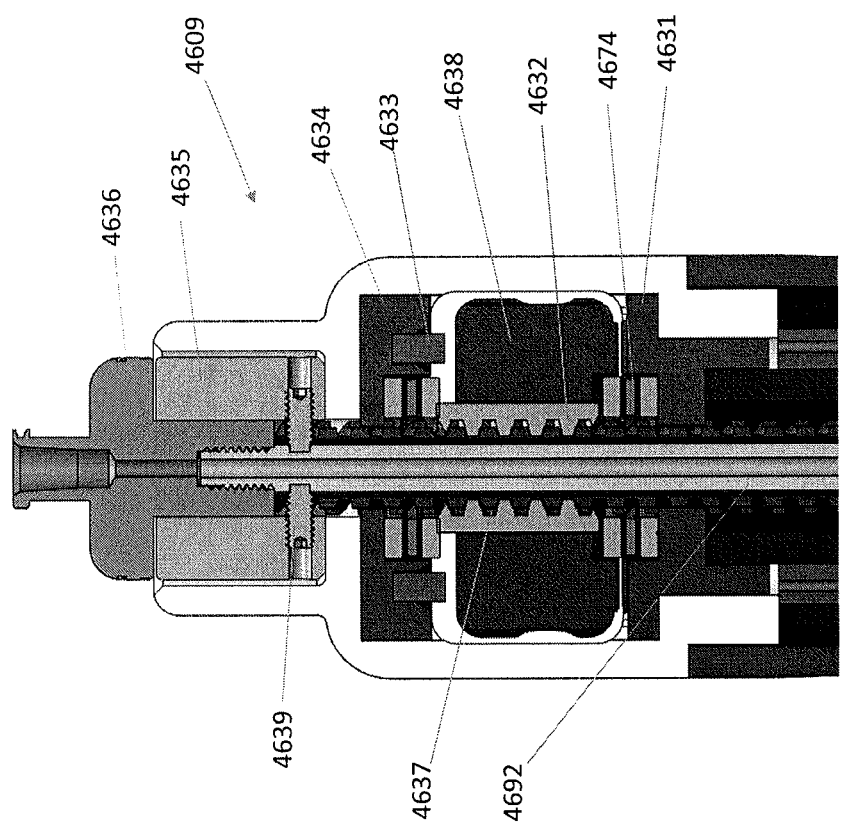
Figure 46Q:
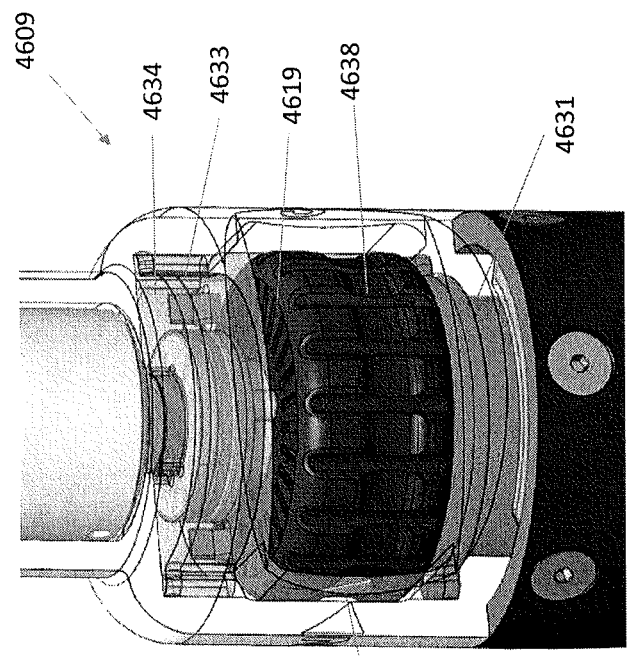
Figure 46P:
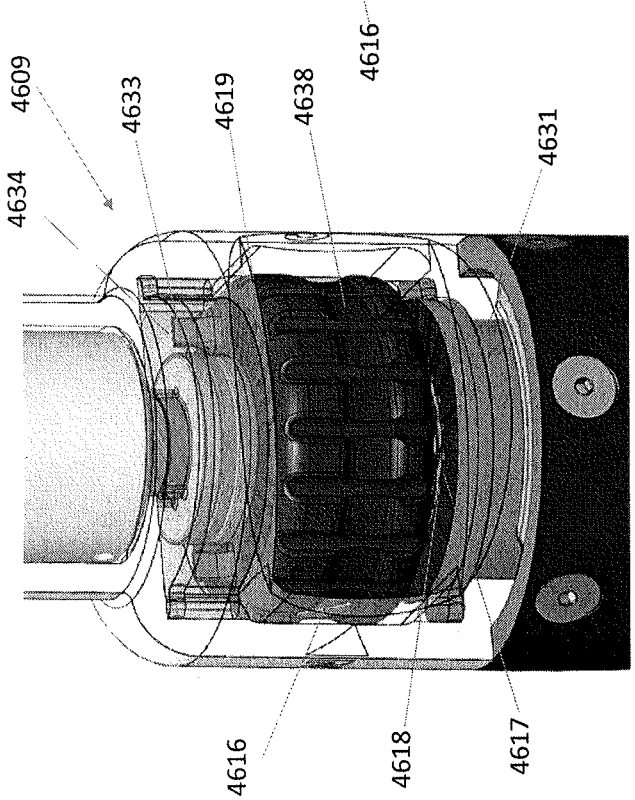
Figure 46T:
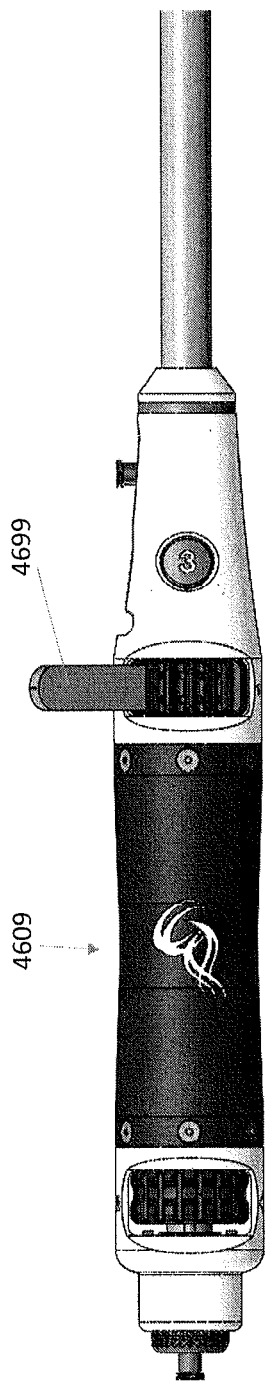
Figure 46V:
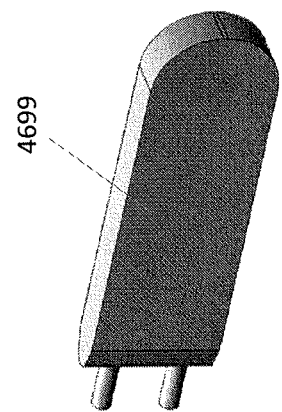
Figure 46U:
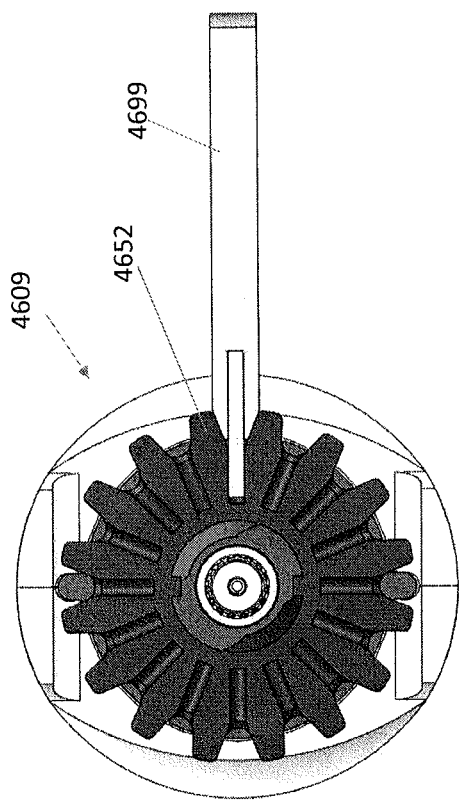
Figure 47A:
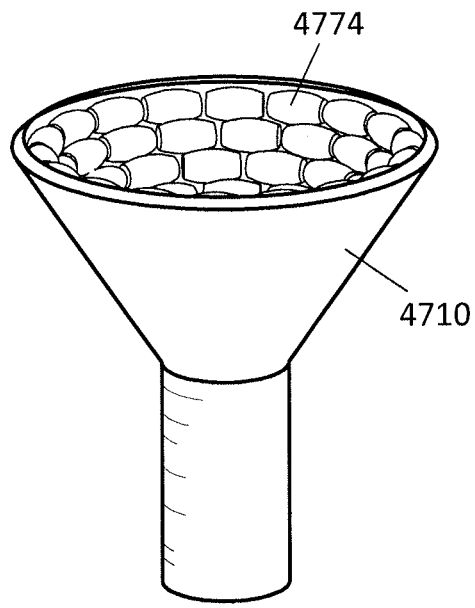
FIGS. 47A-47D show an exemplary loading cone for loading a prosthetic valve into a delivery device.
Figure 47B:
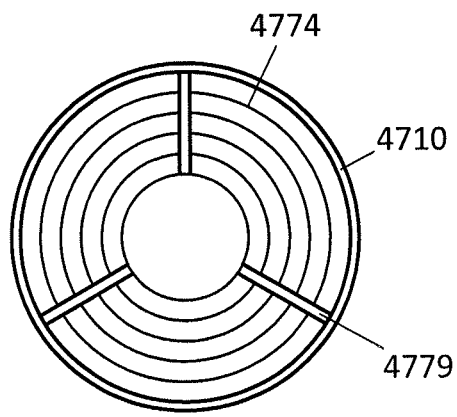
Figure 47C:
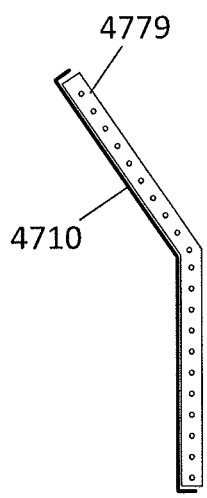
Figure 47D:
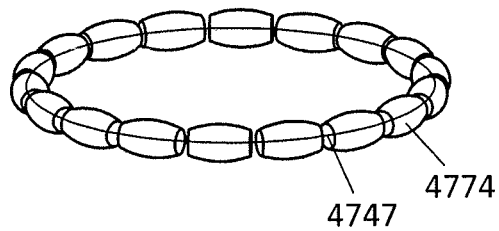

Another exemplary delivery device 4600 is shown in FIGS. 46A-46V. The delivery device 4600 is configured to be used during a surgical delivery method (e.g., during cardiopulmonary bypass) and includes a handle 4609 and elongated portion 4610. The elongated portion 4610 ends in a blunt tip, which includes the tether retainer 4620. Further, a waist ID tube 4646 can extend over the elongated portion 4610. The distal end of the waist ID tube 4646 can include a marker 4650 (e.g., an annular ring protruding from the waist ID tube) configured to align with the center of the mitral valve. The waist ID tube can slide relative to the rest of the elongated portion 4610, as described further below.

As is shown best in FIG. 46B, the handle 4609 can include a sheath control knob 4652 can be configured to control movement of the sheath 4616. The handle 4609 further includes a sheath adaptor 4671 and a sheath sleeve 4672 that is welded to the outer diameter of the sheath 4616 and is configured to interact with the sheath adaptor 4671 set screw to constrain the sheath 3616. The handle 4609 also includes a waist ID tube slide 4673 welded to the waist ID tube 4646.

A ball plunger 4674 holds down the waist ID tube slide 4673 until the sheath adaptor 4671 interacts with the proximal shoulder in the slide 4673. Additionally, the handle 4609 includes a final release button 4677, a final release button latch 4676, and a final release button latch spring 4675.

Retraction of the sheath 4616 and the waist ID tube 4646 during use is shown in FIGS. 46B-46H. That is, in FIGS. 46B and 46C, the sheath 4616 and waist ID tube 4646 are both fully advanced distally with the marker 4650 aligned with the annulus 4664. In FIG. 46D, the sheath 4616 is partially retracted (by rotation of the sheath control knob 4652). The waist ID tube 4646, however, is still fully advanced (held in place by the ball plunger 4674). In FIGS. 46E and 46F, the sheath 4616 is retracted such that the tip of the sheath 4616 is flush with the tip of the waist ID tube 4646. In this configuration, the waist ID tube 4646 is fully advanced (with the marker 4650 aligned with the annulus 4664), but the sheath adaptor 4671 has engaged with the waist ID tube slide 4673. At FIG. 46G, because the sheath adaptor 4671 has engaged with the waist ID slide 4673, the sheath adaptor 4671 can move backwards with the sheath 4616, pulling the slide 4673 through and past the ball plunger 4674, thereby allowing the waist ID tube 4646 to move simultaneously with the sheath 4616. Accordingly, at FIG. 46G, the sheath 4616 and waist ID tube 4646 can be retracted until they are flush with the distal end of tether retainer 4620. In this position, the sheath adaptor 4671 engages with the final release button latch 4676. At FIGS. 46H and I, the final release button 4677 is pushed while the sheath control knob is 4652 is rotated. The waist ID tube 4646 and sheath 4616 are then fully retracted until they are proximal of the tether retainer 4620.

A close-up of the final release button 4677 is shown in FIGS. 46J-L. The release button 4677 is configured to restrict travel of the sheath 4616, preventing inadvertent release. Thus, the latch 4676 catches on the sheath adaptor 4671 when the valve is unsheathed, but the pockets of the tether retainer 4620 are covered such that the tethers cannot be released. The operator can then push and hold the button 4677 (shown in FIG. 46K) while turning the control knob 4652 to complete the final release. As shown in FIGS. 46J-L, the final release button 4677 is configured to rotate around a pin 4681, which is held onto the handle 4609 by two set screws 4682a,b. The spring 4675 pushes against the proximal face of the latch 4676, thereby preventing movement when the button 4677 is a resting position (as shown in FIG. 46J). When the button 4677 is pushed, the latch 4676 is released to thereby release the waist ID tube 4646 and sheath 4616.

Referring to FIGS. 46M-46N, one or more crimps 4648 can be used to hold the proximal ends of the tethers 4626. The crimps 4648 can be positioned inside of the elongated portion 4610 (e.g., just proximal of the tether retainer, such as approximately 1-3", e.g., approximately 2" away from the tether retainer). The crimp housing 4691 can have a groove configured to hold individual cylindrical crimps 4648 (e.g., one for each tether 4626). The crimp sheath 4692 can be configured to constrain the crimps 4648 within the groove of the housing 4691. The crimp sheath 4692 can but up against a shoulder on the crimp actuation tube 4692, which can be attached to the crimps 4648 at the distal end and to the tether terminator 4635 in the handle 4609. Further, the crimp sheath 4693 can be axially constrained against the shoulder of the actuation tube 4692 by the crimp housing 4691, which can screw onto the actuation tube 4693 until it sandwiches the crimp sheath 4692.

The tether control features at the distal end of the handle 4609 are shown in FIGS. 46O-S. The crimp actuation tube 4692 (coupled with the crimps 4648 and tethers 4626 at the distal end of the device) extends into the handle 4609 and terminates in a luer cap 4635, which screws onto the actuation tube 4692. The luer cap 4635 can be configured to fit standard luer ports (e.g., for passage of a guidewire, flush access, etc.). A tether terminator 4635 is attached to the actuation tube 4692 with two point set screws 4639 to provide rotational resistance to prevent the tethers from twisting in the distal part of the device. The screws 4639 further couple the actuation tube 4692 to a threaded rod 4637. Rotating the tether control knob 4638 can move the actuation tube 4692, which can activate/move the crimps 4648 and tethers proximally and distally. Additionally, the tether control features include a proximal race plate 4634 with one or more pawls 4633 attached thereto, a distal race plate 4631 with grooves 4617, and a ball bearing 4674 therein, one or more pawl 4633, and a suture control knob sleeve 4632.

As shown in FIGS. 46F-46Q, the tether control knob 4638 can be configured to move from a proximal position (FIG. 46P) to a distal position (FIG. 46Q). In the proximal position, the knob 4638 can be configured to freely spin in both directions (to tighten or loosen the tethers) while in the distal position, the knob 4638 can be configured to ratchet in only a single direction (e.g., the direction that provides for tightening of the tethers).

In the proximal (free-spinning) position, grooves 4619 on the proximal face of the control knob 4638 can be configured to engage pawls 4633, which can be made of a flexible plastic. When turning the knob 4638, the movement of these pawls 4638 between the grooves 4619 can provide auditory feedback (e.g., clicking) to indicate that the knob 4633 is moving in the proximal free-spinning configuration. The pawls 4633 can also provide resistance to turning, thereby helping to resist back-driving. The free-spinning mode can advantageously provide rapid motion, such as for laying down the atrial anchor quickly to achieve full blood flow.

In the distal (ratcheting) position, angled ratchet features 4618 on the control knob 4638 interface with corresponding ratchet features 4617 on the distal race plate 46341. Interaction of these angled ratchet features 4618, 4617 prevents the threaded rod 4637 from back driving and therefore prevents rotation in the direction that would loosen the tethers. This can be useful, for example, when collapsing the proximal anchor of the valve or when advancing the sheath 4616 over the distal anchor. Further, rotating through the ratchets 4617, 4618 provides auditory feedback on whether the tethers are moving backwards.

Referring to FIGS. 46R-46S, two spring and ball plungers 4616 can be screwed into the control knob 4638 to engage with features 4615 (e.g., indents) on the knob sleeve 4632. The interaction between the spring and ball plungers 2616 and the features 4615 can control whether the knob 4638 is in the proximal position or the distal position. During use, the knob 4638 can be held and pushed/pulled along the axis of the device. The force caused by doing so pushes the ball plungers 2616 inwards to allow the axial motion. The distal feature 4615 can have a larger indent the proximal feature 4615, thereby ensuring that the knob 4638 can bounce through the ratchet features in the distal position without slipping into the free-spinning proximal position.

Referring to FIGS. 46B and 46T-V, in some embodiments, a torque bar 4699 can be used to provide additional leverage and control when turning the sheath control knob 4652. The torque bar 4699 can include one or more posts 4698 configured to mate with corresponding features in the knob 4652 (e.g., between radial notches in the knob 4652). When mated, the bar 4699 can extend radially outwards relative to the knob 4652 and can provide additional leverage by increasing the radius at which the input force is applied (i.e., provides for pushing on the bar 4699 versus the outer diameter of the knob 4652). This can advantageously make it easier for the user to sheath or unsheath, particularly when packing forces for the valve are high. Further, inserting the bar 4699 into the knob 4652 can also prevent rotation (by abutting the handle body), holding the knob in place against accidental rotation or back driving.

Another exemplary delivery device 4900 is shown in FIGS. 49A-49D and includes crimps rather than an external clamping mechanism. Device 4900 is similar to device 4600 except that it is designed to be delivered transatrially (rather than surgically) and thus includes a tapered nosecone 4906. The device 4900 further does not include a waist identification tube and marker because x-ray and echo are generally used during transatrial delivery rather than direct visualization. Instead, radiopaque markers, such as tantalum rings, on the nosecone and/or catheter tip can provide depth and perpendicularity guidance under x-ray and/or echo.

In this embodiment, the atrial access sheath 4991 includes grooved ring 4995 thereon. The grooved ring 4995 can be configured to hold cinched atrial tissue thereto during use. The atrial access sheath 4991 can then remain in position as the rest of the delivery device 4900 moves axially in and out without losing hemostasis. Additionally, the device 4900 can include various seals therethrough to create flush paths and maintain hemostasis (similar to other devices described herein).

As with other delivery devices described above, the delivery device 4900 includes a handle 4909 connected to an elongated portion 4910. A central stem 4918 terminates in a tapered nosecone 4906, and an inner sheath 4916 extends around the central stem 4918. A tether retainer 4920 is positioned just proximal to the nosecone 4902 for holding the distal ends of the tethers, as described above. A sheath control knob 4952 is used to control movement of the sheath 4916 (i.e., to control the covering and uncovering of the tether retainer 4920). Further, a release knob 4950 is positioned at the proximal end of the handle 4909. Rotation of the release knob 4950 loosens the tethers, e.g., to allow the anchors of the device 4900 to expand. The release knob 4950 is further connected to an external secondary release mechanism 4959 that is positioned at the distal end of the handle 4909. The external secondary release mechanism 4959 includes a tether terminator 4995, two flat washers 4955a,b, and a thumbscrew 4952. The thumbscrew 4952 can, for example, have external steps within which the washers fit. The proximal ends of the tethers can loop around the washers 4955a,b and then be clamped down with the terminator 4995. If the thumbscrew 4952 is loosened, then the washers 4955a,b can separate, loosening and freeing the tethers at the proximal end (e.g., as a bail out in emergencies).

In some embodiments, the proximal portion of the prosthesis may be expanded before the distal portion (i.e., for the surgical or transatrial approach, the atrial anchor can be expanded before the ventricular anchor). For example, if it is difficult to advance the delivery device far enough into a left ventricle to deploy the distal portion first, or if it is undesirable to deploy the distal portion first against mitral valve anatomical structures (e.g., the chords), the proximal portion can be deployed first. The delivery devices herein can be modified with an outer component that can be axially moved to allow the proximal portion to expand while still radially constraining the distal portion for subsequent expansion.

Turning to FIGS. 23A-G, another embodiment of the mitral valve replacement delivery device 800, is shown. The delivery device 800 shares many of the same features as the delivery devices already described, and thus, features that function the same will not be redundantly described, unless required for clarity. The major difference between the delivery devices already described and the delivery device 800 is that the previously described delivery devices, the distal end petals of the prosthetic valve are deployed first followed by the proximal end petals, while for the delivery device 800, the proximal end petals are deployed first (e.g., the proximal anchor is first deployed in the atrium and then the distal anchor is deployed in the ventricle).

Figure 23A:
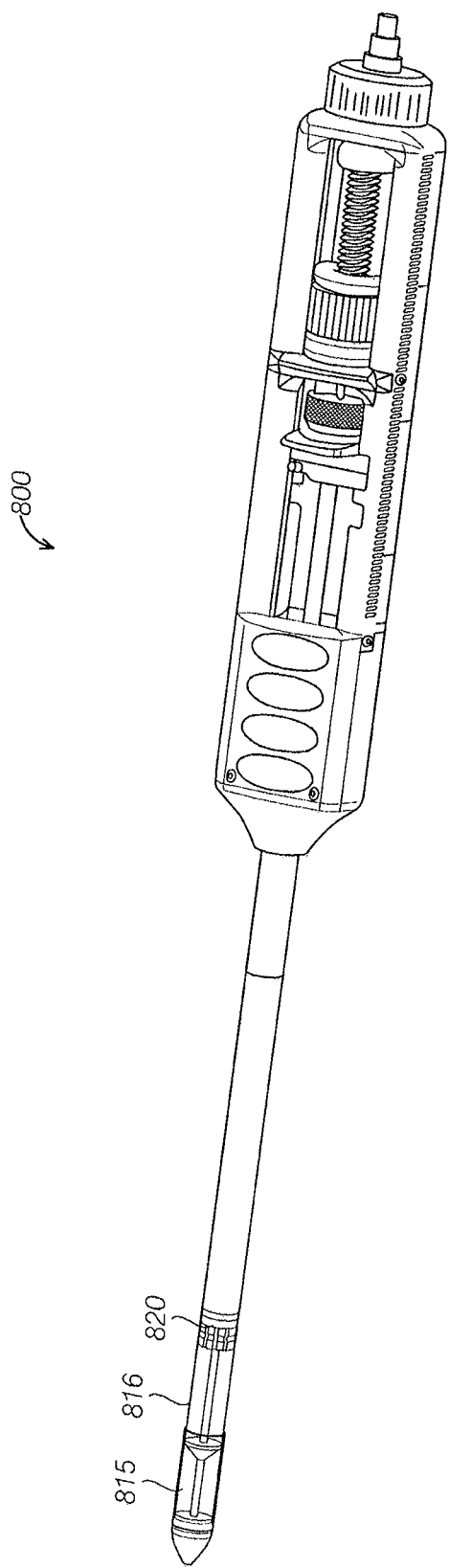
FIG. 23A shows another embodiment of a delivery device.
Figure 23B:
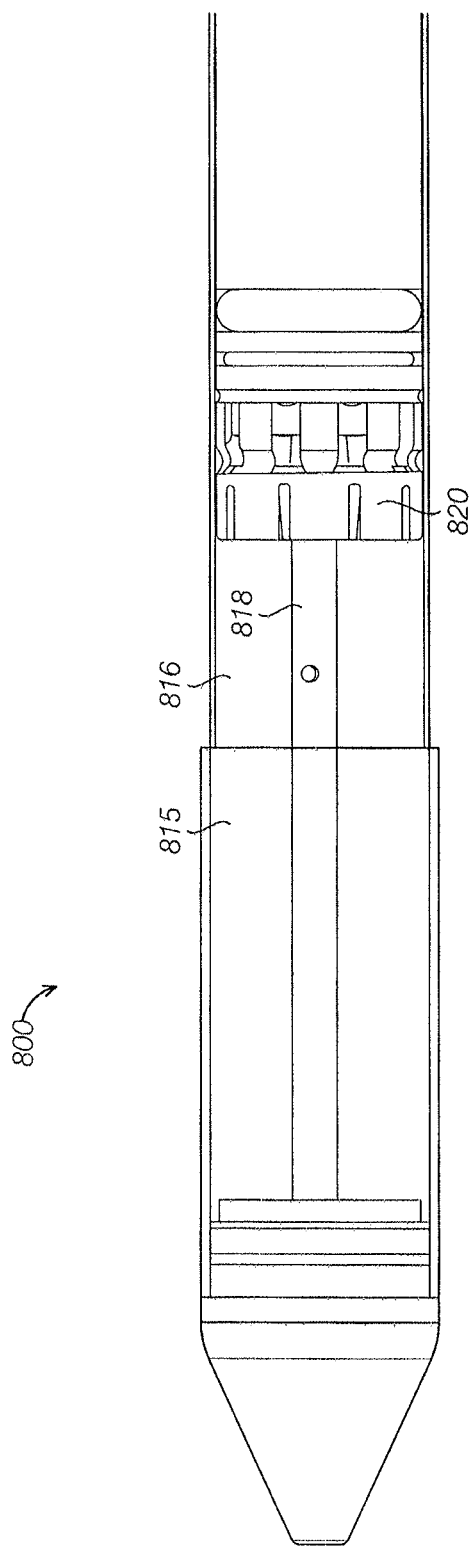
FIG. 23B shows a close up of the distal end of the delivery device of FIG. 23A.
Figure 23C:
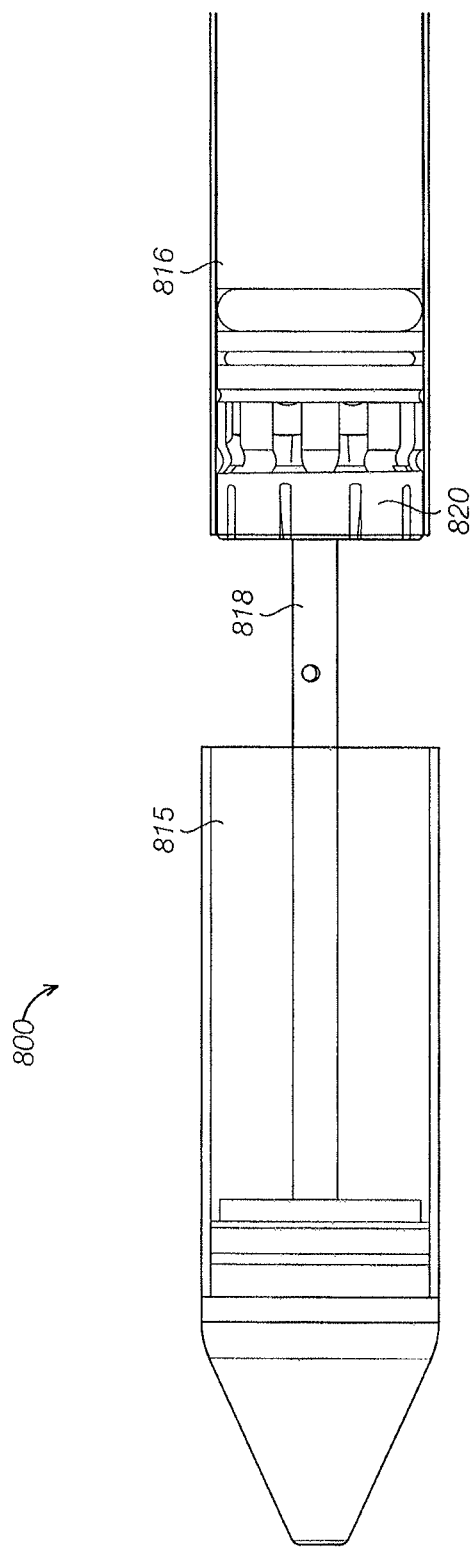
FIG. 23C shows the delivery device of FIG. 23A with a distal inner sheath and a proximal inner sheath moving away from one another.
Figure 23D:
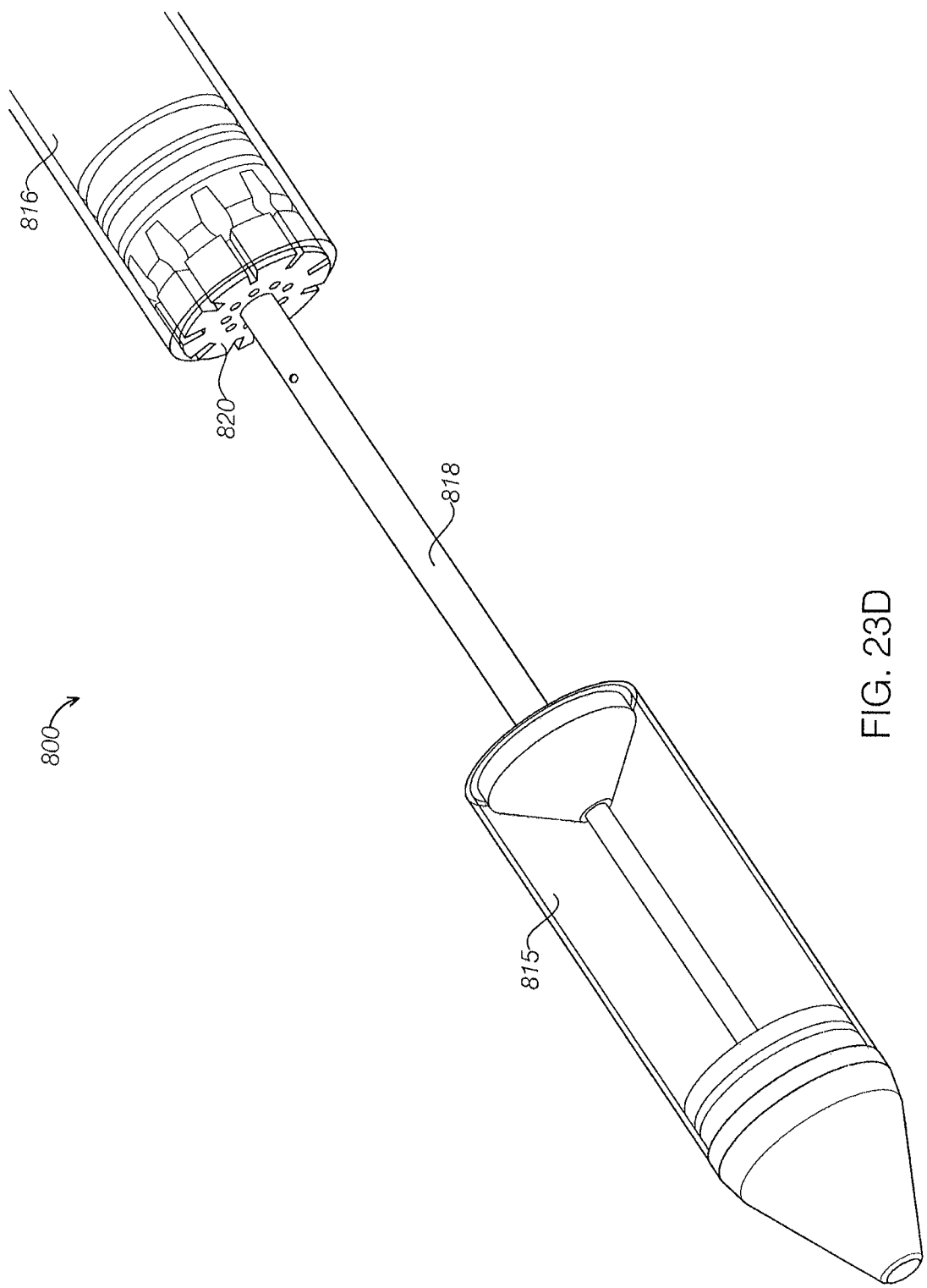
FIG. 23D shows the distal inner sheath and the proximal inner sheath of FIG. 23C moving farther from one another.
Figure 23E:
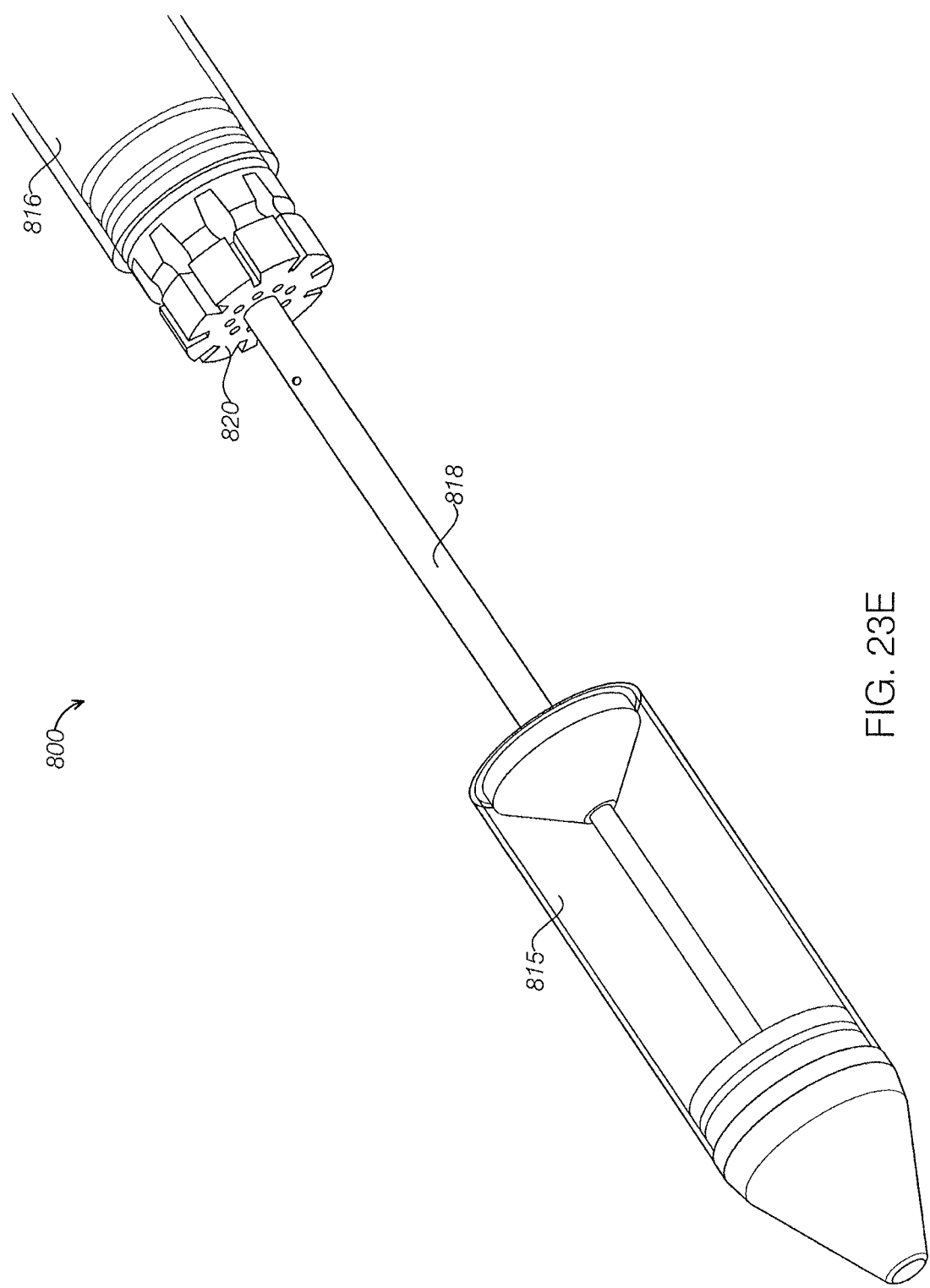
FIG. 23E shows a tether retainer becoming exposed after the proximal inner sheath has been fully further in the proximal direction relative to FIG. 23D.
Figure 23F:
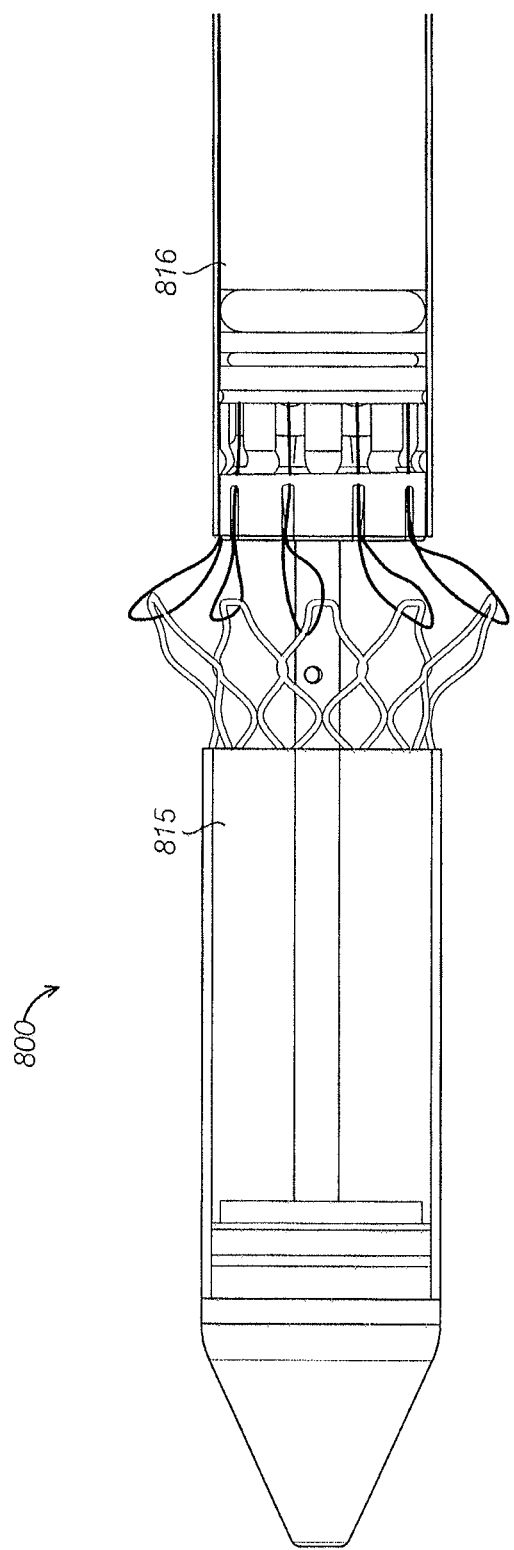
FIG. 23F shows proximal ends of a prosthetic valve deployed but still coupled to a series of tethers of the delivery device of FIG. 23A.
Figure 23G:
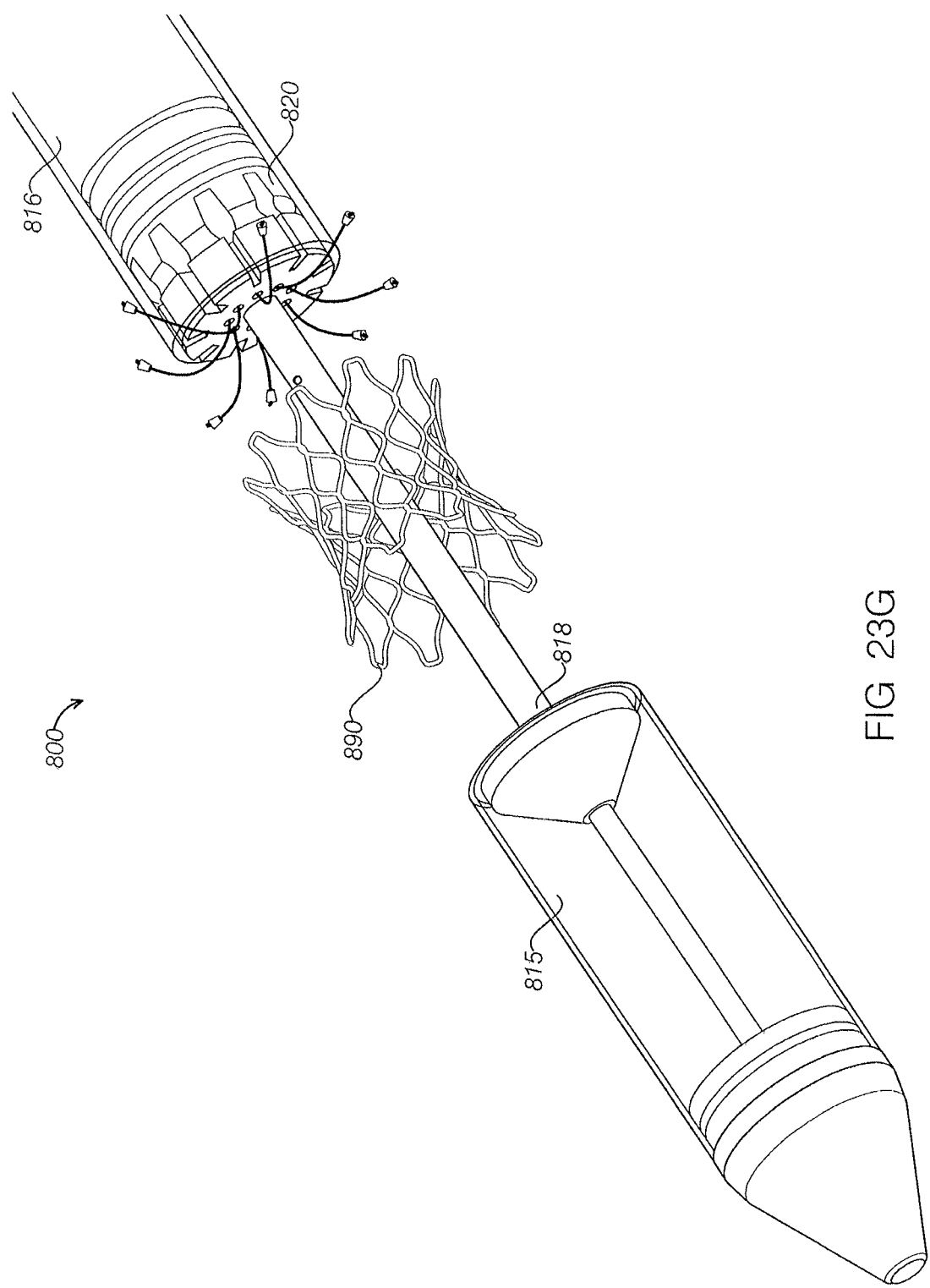
FIG. 23G shows the prosthetic valve fully deployed and uncouple to the tether ends of the delivery device of FIG. 23A.

The delivery device 800 has a device proximal end 802 and a device distal end 804. The delivery device 800 includes two inner sheaths, a distal inner sheath 815 and a proximal inner sheath 816. The distal inner sheath 815 is able to telescope over the distal end of the proximal inner sheath 816 (FIGS. 23A and B). FIGS. 23 C and D show how the proximal inner sheath 816 may be extended and retracted in conjunction with the distal inner sheath 815. Similar to the previous delivery devices, the delivery device 800 includes a tether retainer 820, where the tether retainer 820 is stationary along the centrals stem 818. The prosthetic valve is held in the same manner and orientation as in the previous delivery devices.

Once the prosthetic valve has been coupled to the tethers and the tether ends maintained with the tether retainer 820, the tether control lever 838 may be pulled proximally to tension the proximal petals of the prosthetic valve to close the petals about a central stem 818. The distal end petals of the prosthetic valve may then be forced into a closed position by further pushing the proximal distal sheath 816 distally so that it eventually covers the entire prosthetic valve. Once the entire prosthetic valve has been collapsed, the distal inner sheath 815 may cover a portion of the proximal inner sheath 816. The distal inner sheath 815 is controlled by a distal inner sheath controller 819, which is able to retract and extend the distal inner sheath 815. At its most distal position, the distal inner sheath 815 abuts the nosecone 806. Once the collapsed prosthetic valve is within the distal inner sheath, the proximal inner sheath 816 may be retracted proximally.

To release the prosthetic valve, tension on the tethers may be relaxed. As FIGS. 23E and F show, the distal and proximal inner sheaths 815 and 816 may be positioned to expose the proximal end petals of the prosthetic valve first. This is done by pulling the proximal inner sheath 816 slightly in the proximal direction while also extending the distal inner sheath 815 in the distal direction to first expose the proximal petals. Once the proximal end petals of the prosthetic valve are fully open and positioned, the operator may move the distal inner sheath 815 distally to expose the distal end petals of the prosthetic valve, where the distal petals will naturally curl/flair out to their natural state once the constriction by the distal inner sheath 815 has been removed. The proximal inner sheath 816 may be further retracted to expose the tether retainer 820 so that the tether pockets containing the tether ends are exposed and the tether distal ends may pop from each respective pocket. The delivery device 800 may also include an outer sheath for initially positioning the device within the patient's heart.

Figure 25A:
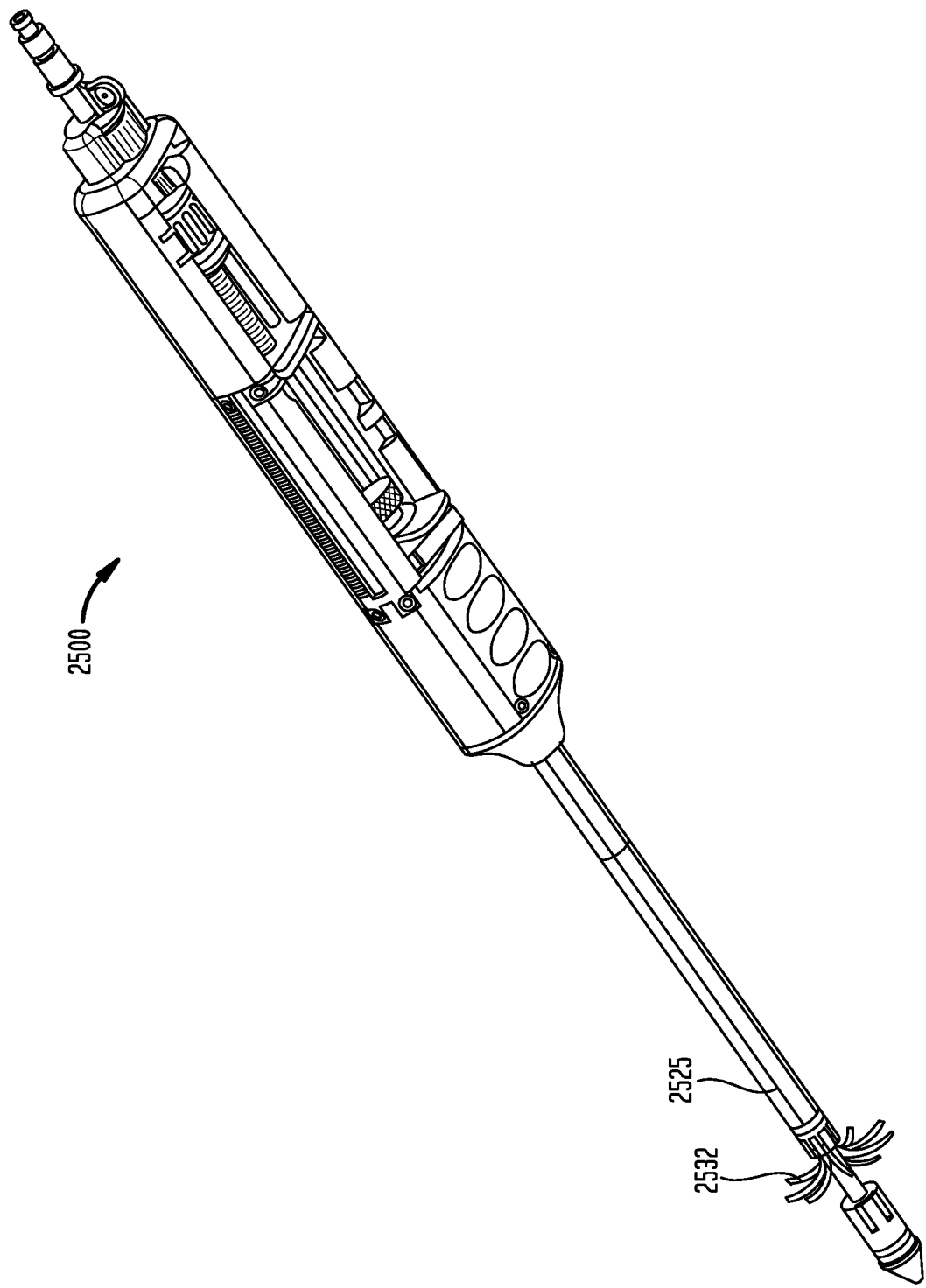
FIG. 25A shows a delivery device configured to deliver the proximal end of a prosthetic valve before the distal end.
Figure 25B:
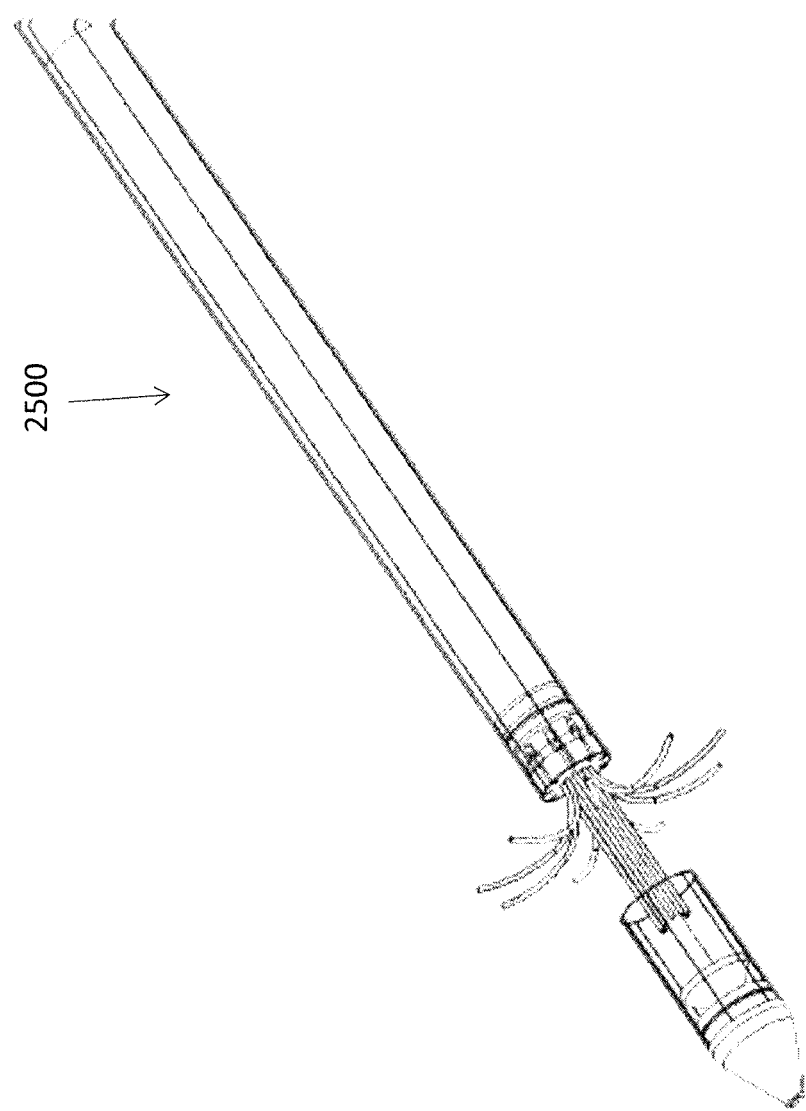
FIG. 25B shows curved hypotubes extending from the delivery device of FIG. 25A.

Another delivery device 2500 configured to deliver the proximal end of the valve before the distal end is shown in FIGS. 25A and 25B. Device 2500 is similar to device 800 except that the hypotubes 2532 through which the tethers extend can be made of a shape memory alloy, such as Nitinol and can be 1.5-2 inches longer than the length of the shaft 2525. Further, the hypotubes 2532 can be shape set to curve at the distal ends thereof. That is, the hypotubes 2532 can be configured to maintain a substantially straight configuration when positioned within the shaft 2525. However, as the slider is advanced to advance the tethers (and allow the proximal anchor to expand), the hypotubes 2525 can likewise extend the shaft 2525 and curve back proximally (while holding the tethers therein).

Figure 26:
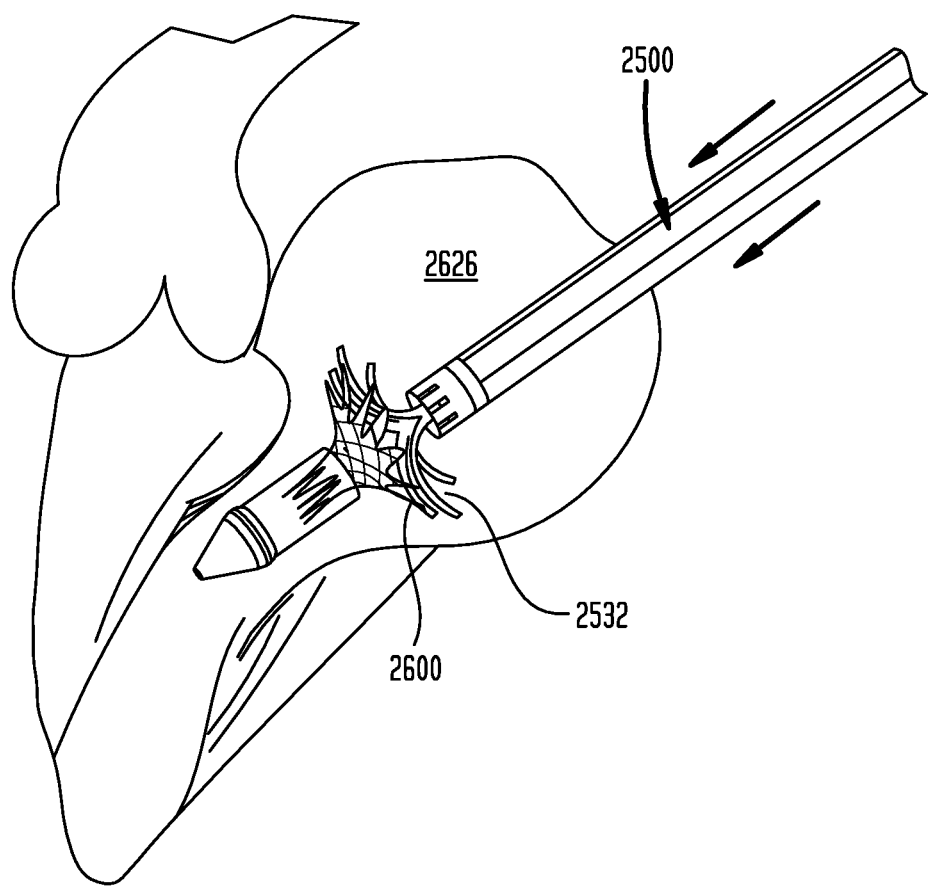
FIG. 26 shows use of the device of FIGS. 25A-25B to place a prosthetic valve in the heart.

As shown in FIG. 26, the end of each hypotube 2532 can be configured so as to sit against a portion of the proximal anchor of the valve 2600 (e.g., against a flattened or mating feature on the valve) during placement of the valve in the heart 2626. As such, in use, when the entire delivery device 2500 is pushed distally (i.e., to seat the proximal anchor against the tissue), the hypotubes 2525 can provide support to the proximal portions of the anchor 2600 (e.g., to ensure that the proximal anchor does not collapse back down).

Figure 39A:
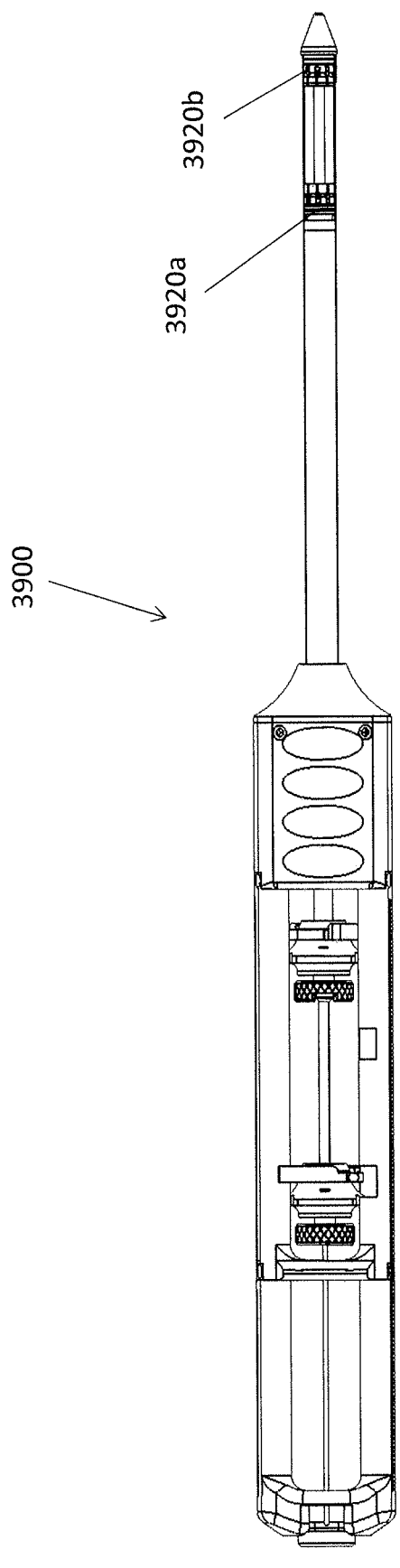
FIG. 39A shows a delivery device configured to deliver the proximal end of a prosthetic valve before the distal end.
Figure 39B:
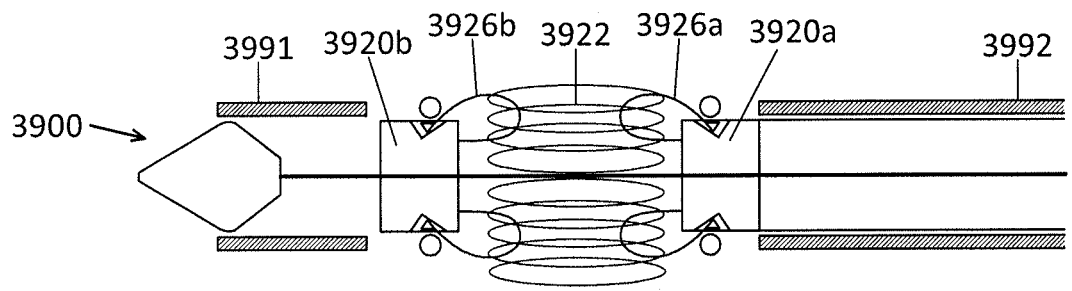
FIGS. 39B-E show a method of loading the device of FIG. 39A with the prosthetic valve.
Figure 39C:
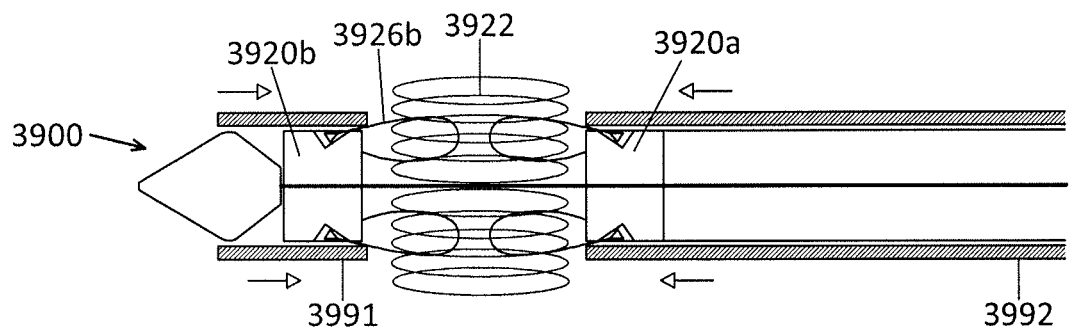
Figure 39D:
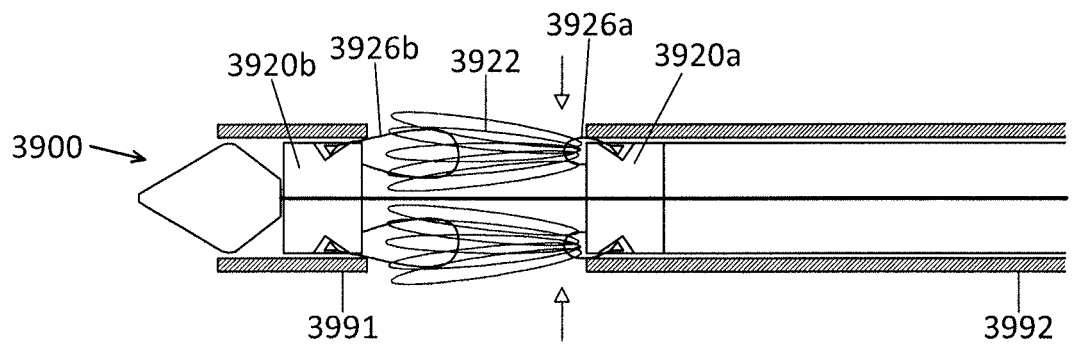
Figure 39E:
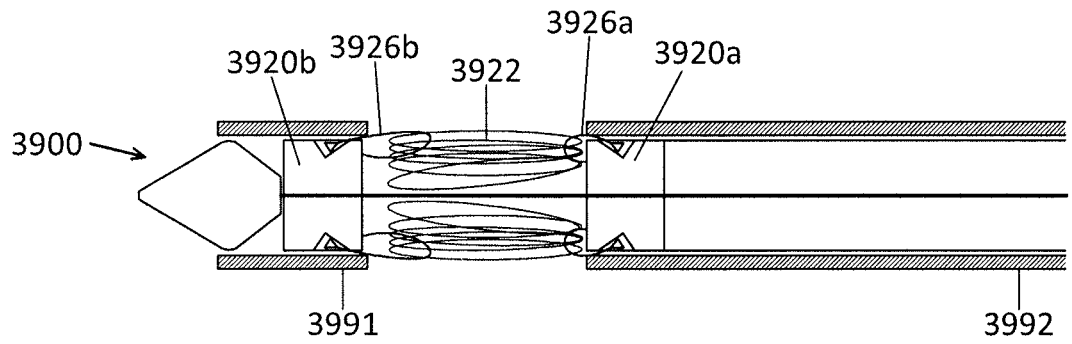
Figure 39F:
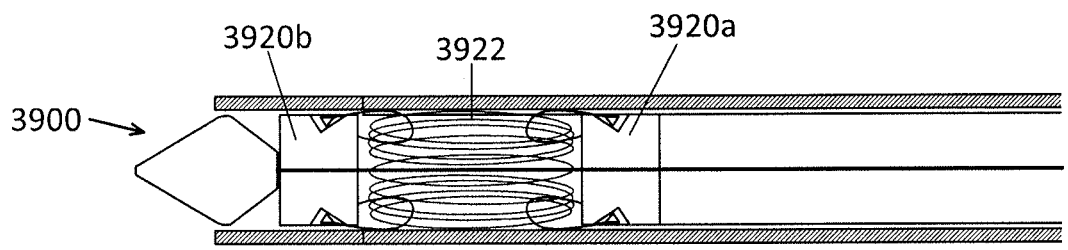
FIGS. 39F-39I show a method of deploying the valve using the delivery device of FIG. 39A.
Figure 39G:
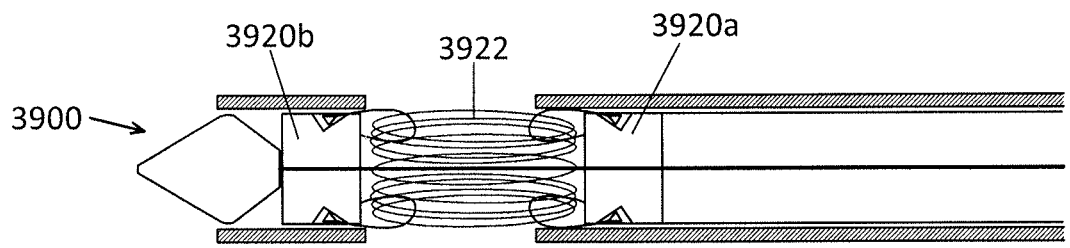
Figure 39H:
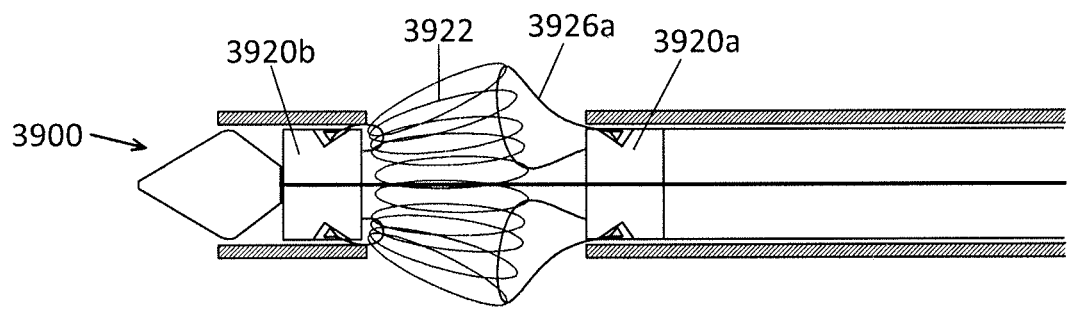
Figure 39I:
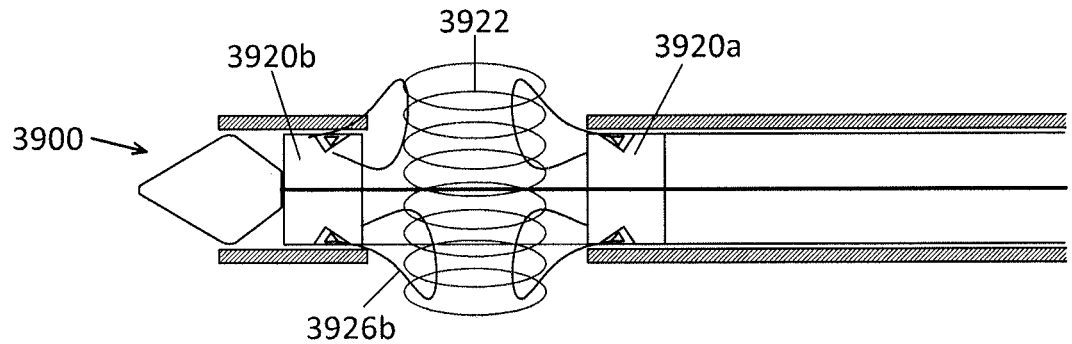

Another exemplary delivery device 3900 configured to deliver the proximal end of a prosthetic valve before the distal end is shown in FIG. 39A. The device 3900 includes two tether retainers 3920a,b. Tether retainer 3920a is configured to hold tethers that extend through the proximal end of the valve while tether retainer 3920b is configured to hold tethers that extend through the distal end of the valve.

A method of loading the device 3900 with a valve 3922 is shown in FIGS. 39B-39E. To begin, at FIG. 39B, both sides of the valve are threaded with tethers 3926a,b, and the tether beads are placed in the tether retainers 3920a,b. At FIG. 39C, a distal sheath is pulled proximally over the retainer 3920b and a proximal sheath is pulled distally over the tether retainer 3920a. At FIG. 39D, the tethers 3926a are pulled proximally to collapse the proximal end of the valve. At FIG. 39E, the tethers 3926b are pulled distally to collapse the distal end of the valve. A sheath can then be pulled fully over the collapsed valve.

A method of deploying the valve 3900 is shown in FIGS. 39F-39I. At 39F, the valve is fully sheathed. At 39G, the sheath(s) are removed from the valve. At 39H, the proximal valve is released by loosening tethers 3926a. At 39I, the distal valve is released by loosening tethers 3926b.

Figure 24A:
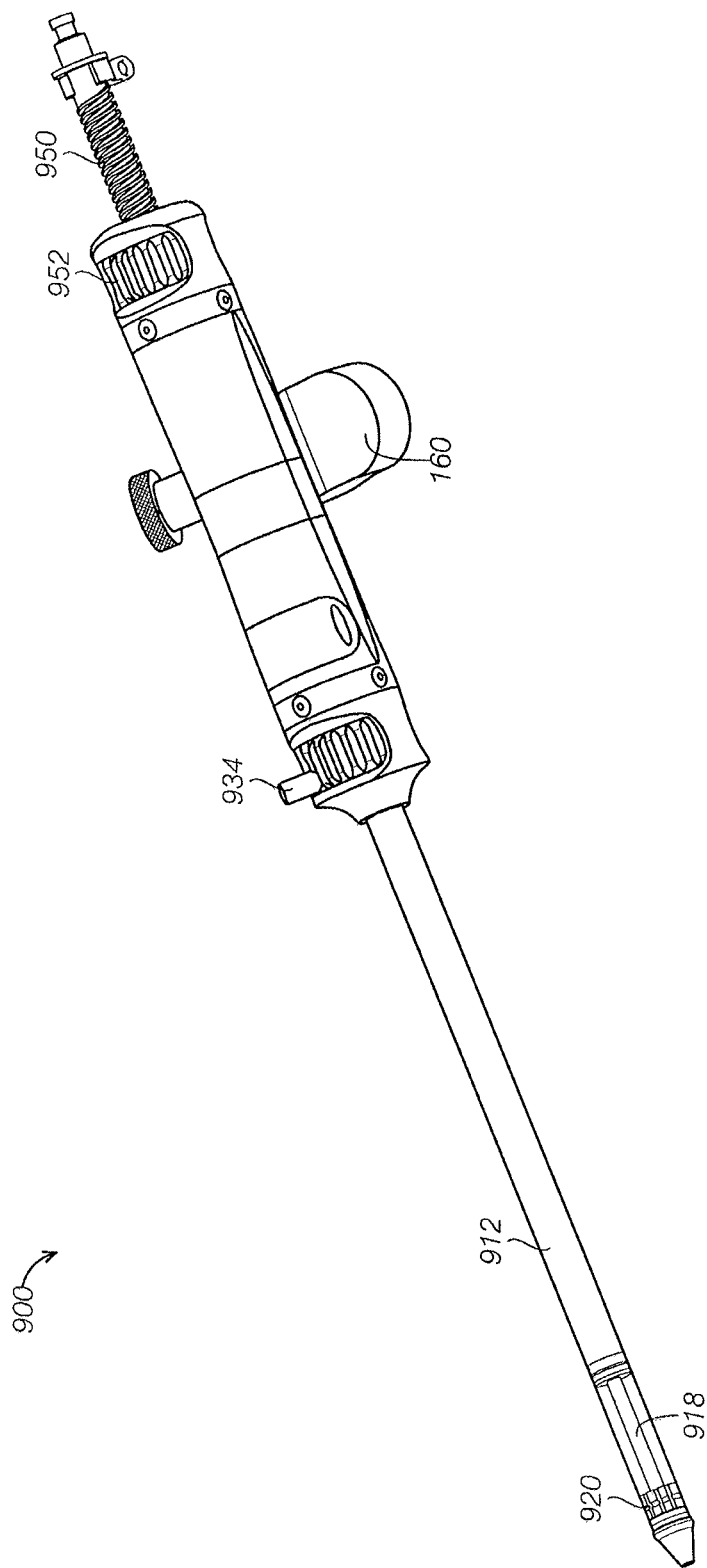
FIG. 24A shows another embodiment of a delivery device.
Figure 24B:
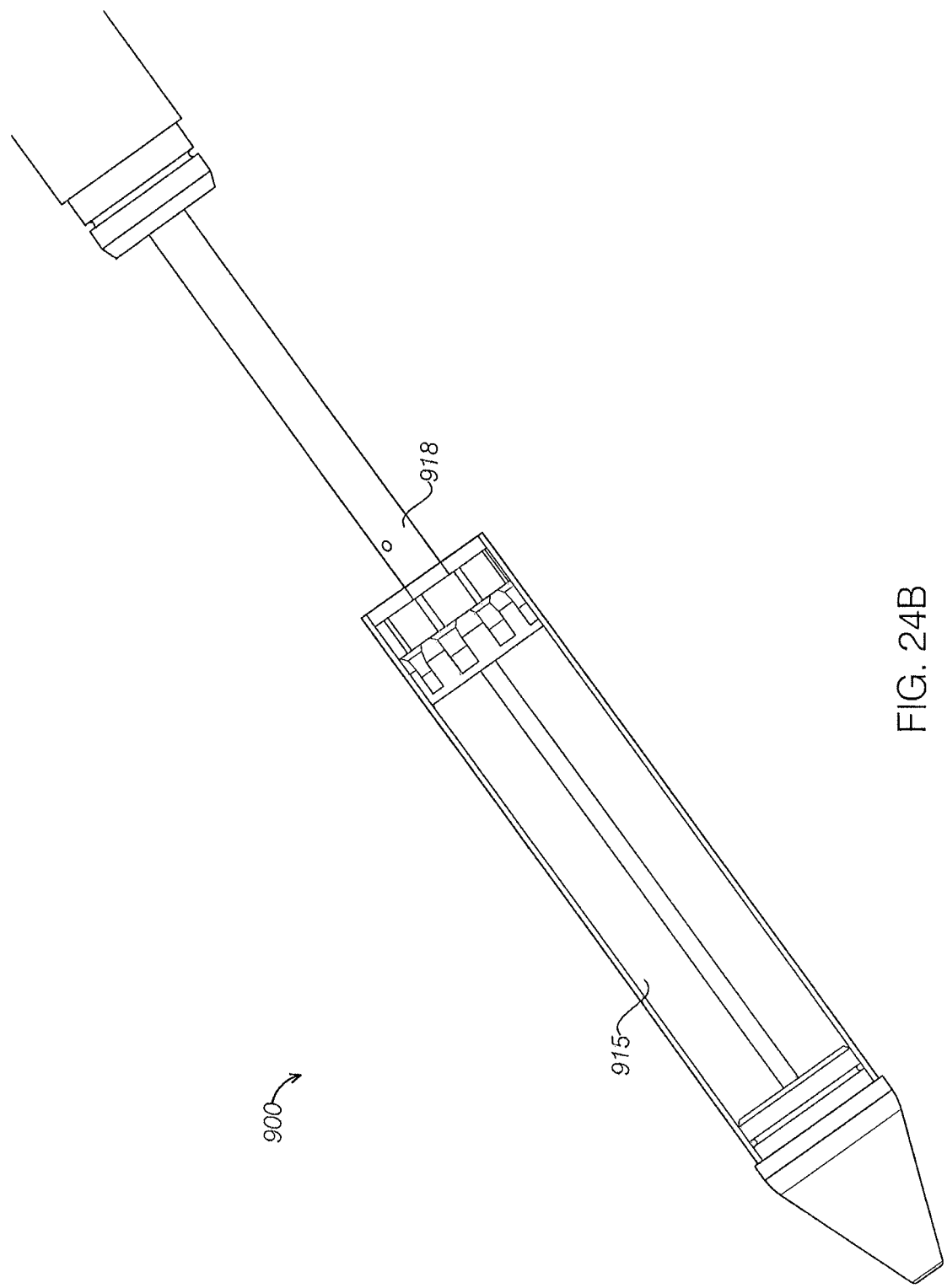
FIG. 24B shows a distal end inner sheath of the delivery device of FIG. 24A partially extended in the distal direction.

Yet another embodiment for prosthetic valve delivery, a delivery device 900, can be seen in FIG. 24A-24F. The delivery device 900 also release the proximal end petals of the prosthetic valve first. The delivery device 900 as shown in FIG. 24A uses a slightly different mode of maintaining the tether for the prosthetic valve compared to delivery device 800. Similar to delivery device 800, the delivery device 900 includes a shorter distal sheath 915 that abuts a nosecone 906 at a device distal end 904. The delivery device 900 includes a distal sheath 915 that may extend and retract with the use of a sheath controller 952 (FIG. 24B). The delivery device 900 further includes a central stem 918. Unlike in previous configurations, the central stem 918 here further includes a series of nesting tubes. In this particular configuration, nine nesting tubes 933 are arranged around a center core that runs to the nosecone 906. The center core houses a guidewire known in the catheter arts. Instead of a tether control lever, the delivery device 900 includes a tether control knob 938, where the tether control knob 938 functions to increase, decrease, or maintain tension on the tether ends. Similar to the other delivery devices, the proximal ends of the tethers are maintained at the tether control knob 938. In one example, each tether runs from the tether control knob 938 to a nesting tube 933 until it reaches the tether retainer 920. Each tether exits its respective nesting tube at a distal location and threads into a corresponding tether retaining aperture 923, where each tether travels the length of the tether retainer 920 and exits the tether retaining apertures 923 at its proximal end. From there, each tether distal end may be introduced into corresponding tether pockets 924 and tether slots 922.

To load a prosthetic valve, the free tether ends near the distal end of the delivery device 900 are looped around the distal end petals of the prosthetic valve. Once the tethers have been coupled to the prosthetic valve, the tether control knob 938 may place tension on the distal end petals through adjusting the tether control knob 934 and pull them close toward the central stem 918. In delivery device 900, the distal sheath 915 may be pulled back proximally along a central stem 918. When the distal end petals have been so tensioned as to pull them straight, the distal end sheath 915 may be extended proximally to cover the distal end petals. Further retracting the distal end sheath 915 will begin to cover the proximal end petals of the prosthetic device. The collapsed prosthetic valve and the tether retainer 920 are eventually completely maintained within distal inner sheath 915. The sheath control knob 952 adjusts the position of the distal inner sheath 915 through lead screw 950. The distal sheath 915 abut the nosecone 906.

For deploying the prosthetic valve, the distal inner sheath 915 may be extended distally relative to the tether retainer 920 by adjusting the sheath control knob 952. When this occurs, the proximal end petals are exposed. Because the distal inner sheath 915 was the only thing keeping the proximal petals in a straightened configuration, once this confinement is removed, the proximal end petals will relax and curl to their natural shape (FIG. 24C). Once the proximal end petals have been place in an optimal location within the patient's heart, the distal inner sheath 915 may be further extended distally in conjunction with relaxing tension on the tether ends through adjusting the tether control knob 938 which allow the distal end petals to relax and expand (FIG. 24D). The distal inner sheath 915 may be further advanced distally such that the pockets of the tether retainer 920 are exposed and the tether ends are allowed to become uncoupled to the tether retainer 920 (FIG. 24E). Finally the tether ends may be tensioned so that they are pulled free from the prosthetic device completely (FIG. 24F), where now the delivery device may be removed.

Figure 10:
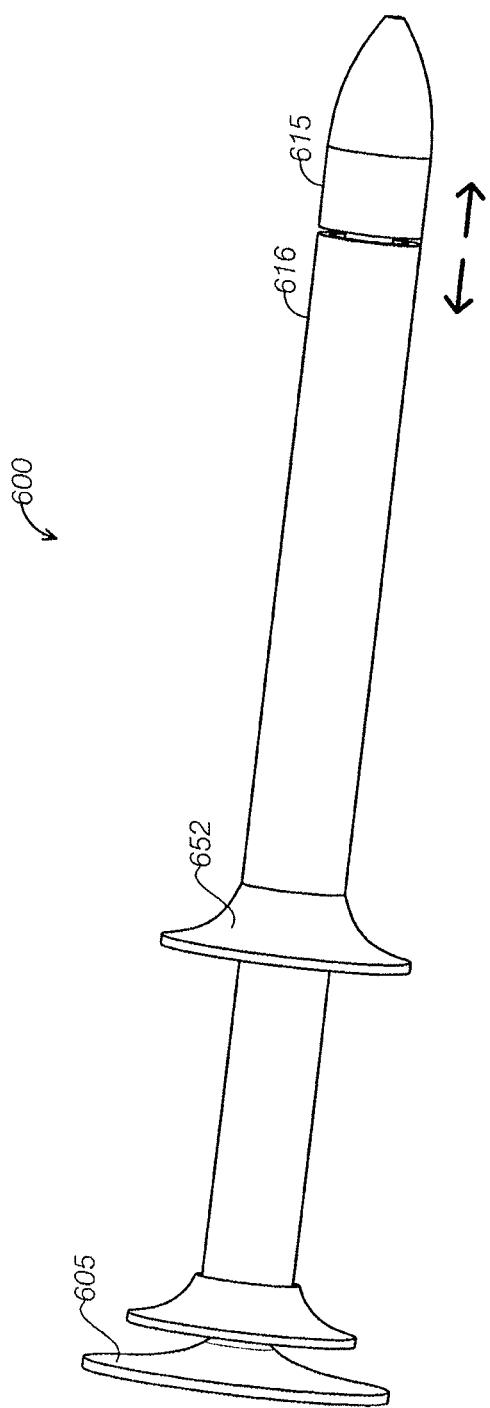
FIG. 10 shows another embodiment of a prosthetic valve delivery device.

FIG. 10 shows another exemplary delivery device 600 that is configured to expand the proximal portion before the distal portion. The central assembly of delivery device includes an expansion control member, and in other embodiments herein. However, in this example, the expansion control member is positioned and configured to maintain the distal portion in a collapsed configuration. The proximal portion is allowed to freely expand upon retraction of the outer sheath. In use, the sheath control handle 652 is retracted in the proximal direction (as shown by the arrow), causing proximal sheath 616 to be withdrawn proximally. This causes the proximal portion of the expandable anchor to self-expand. The distal portion of the expandable anchor is still maintained in a collapsed delivery configuration radially within the distal sheath 615. To expand the distal portion of the anchor, sheath control handle 652 is advanced distally, causing distal sheath 615 to be distally advanced (as shown by the arrow) past the distal portion of the expandable anchor. This causes the distal anchor portion to self-expand. Thus, device 600 is configured such that a proximal portion of the expandable anchor is expanded before the distal portion. The device in FIG. 10 can similarly include any of the additional restraining elements (e.g., tethers) described herein to further control the expansion of either the proximal or distal anchor portions.

In some embodiments, wherein tethers are either released or cut through a secondary release mechanism, a tether retrieval mechanism can be used (i.e., to ensure that the tethers are not left in the patient's body). For example, FIGS. 28A-28H show a delivery system 2800 including a tether retrieval mechanism including a plurality of lassos 2838a, b,c configured to be placed around one or more tethers 2826 at the distal end of the delivery device (e.g., at the retainer 2820). The proximal end of the lassos 2838a-c can be attached to a ring 2830 (see FIG. 28C). The ring can 2830 can be positioned at the proximal end of the shaft of the delivery device (e.g., as part of the handle). In use, when the tethers are cut or released, the ring 2830 can be pulled proximally to pull the lassos 2838, thereby pulling the tethers 2826 out of the body. Advantageously, pulling the ends of the tethers out can provide confirmation of full detachment of the tethers from the valve.

Figures 29A, 29B:
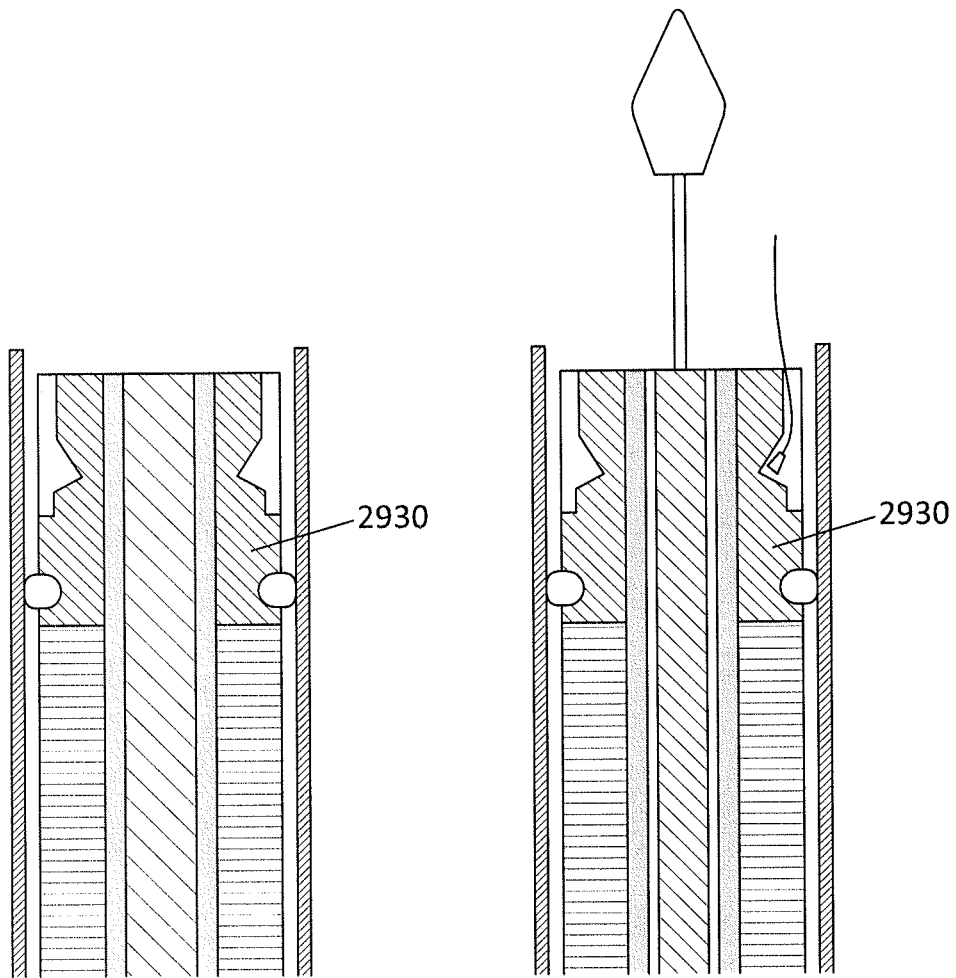
FIGS. 29A-29C show another exemplary tether retrieval system.
Figure 29C:
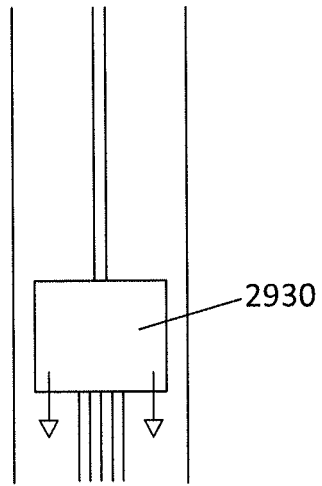

A delivery system including another exemplary tether retrieval mechanism is shown in FIGS. 29A-C. The catheter includes an axial movable tether retainer 2920. In use, as the tether retainer 2920 is pulled axially, the lengths of tether can likewise be pulled therewith (as shown in FIG. 29C). Advantageously, the lengths of tether can be pulled back while the sheath and nosecone remain stationary.

Figure 20C:
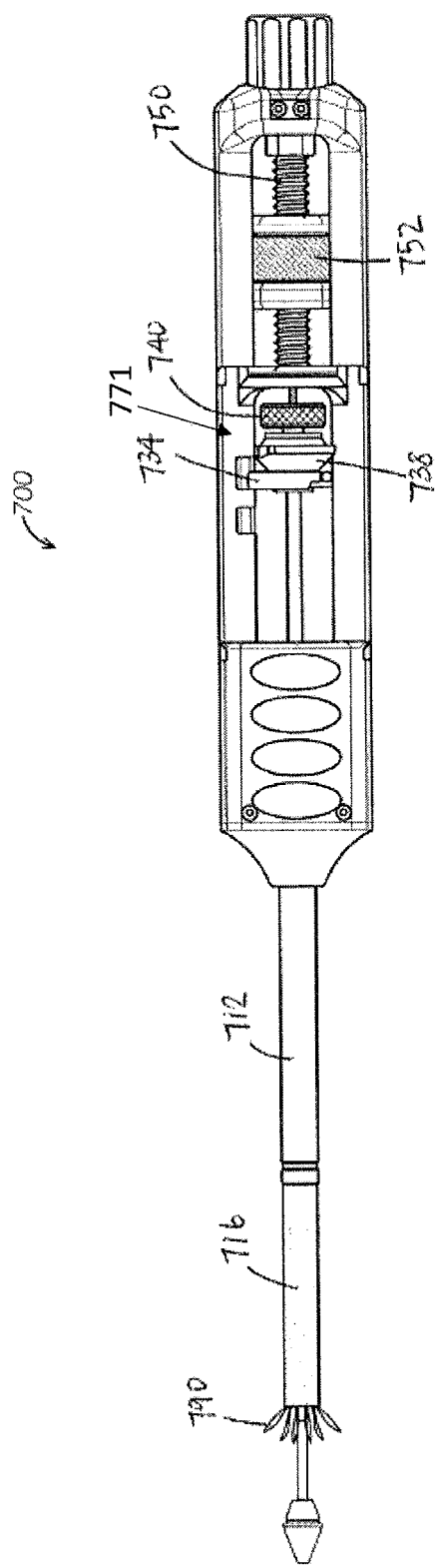
FIG. 20C shows the delivery device of FIG. 11A having the prosthetic valve partially drawn into the delivery device.

In some embodiments, a tether loading cone 710 (see FIG. 11A) may be used to aid with loading a prosthetic valve into the delivery device 700. The operator can apply tension to the series of tethers using the tether control lever 738 such that the prosthetic valve proximal petals are straightened enough to fit into the inner sheath 716. The tether loading cone 710 aids with directing the individual petals into inner sheath 716. As the operator continues to pull the series of tethers proximally, the proximal end petals will be completely housed within the inner sheath 716 followed by the central portion of the prosthetic valve (FIG. 20C). Once the prosthetic valve central portion has been pulled into the inner sheath 716, the tension being exerted on the prosthetic valve will continue to pull the prosthetic valve axially in the proximal direction such that the distal end petals now begin to uncurl and straighten out while being pulled into the inner sheath 716. The prosthetic valve is now completely loaded when the entire valve is maintained within the inner sheath 716 even though tension is still being maintained on the proximal end of the prosthetic valve through the tether control lever 738. Once the prosthetic valve has been loaded, the tether loading cone 710 may be removed and the valve placement procedure may proceed.

Another exemplary loading cone 4710 is shown in FIGS. 47A-47D. The loading cone 4710 includes a plurality of looped wires 4747 extending circumferentially along the inner surface thereof. The wires 4747 can have cylindrical beads 4774 strung thereon. A plurality of the looped wires 4747 and beads 4774 are positioned at intervals along the inner surface of the conde 4710. In one embodiment, the looped wires 4747 can be passed through supports 4779 that are positioned at various circumferential locations along the inner surface of the cone 4710. In use, as the valve is pulled into the delivery device, the beads 4774 can rotate or roll to help move the valve into the device.

In some embodiments, the delivery devices described herein also include a grasper to allow the operator both to adjust the depth with which the device distal end penetrates the patient's heart chamber and to aid in maintaining the delivery device in position during use.

Figure 21A:
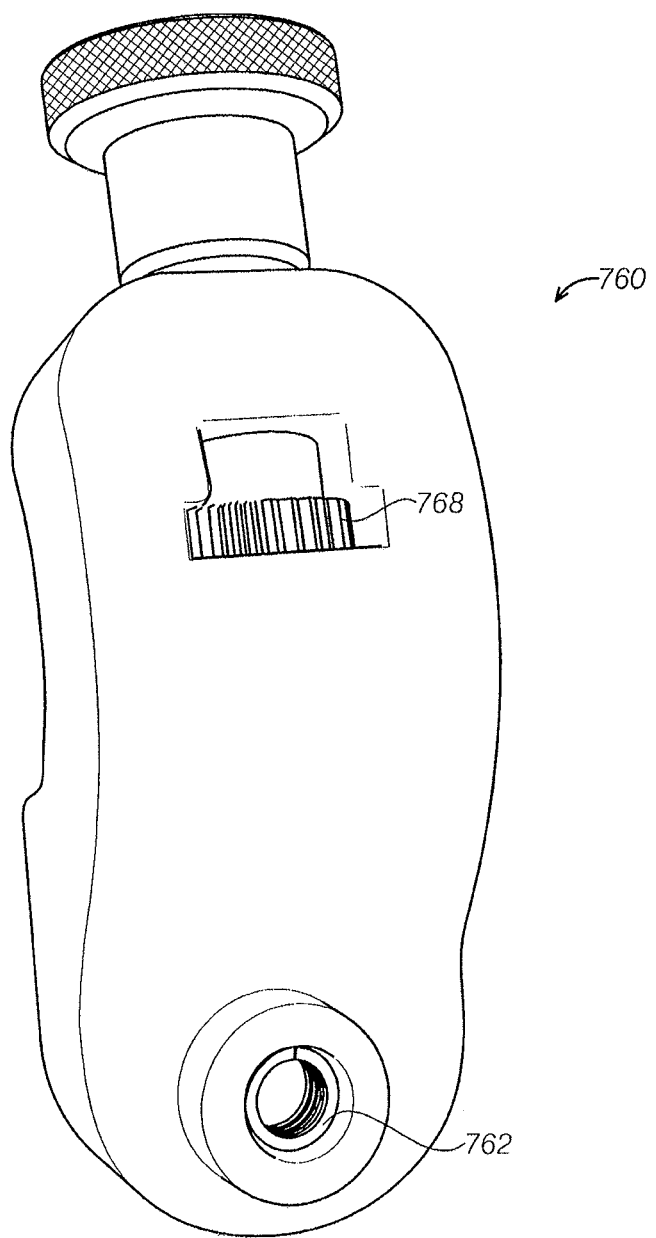
FIG. 21A shows a top view of a grasper.
Figure 21B:
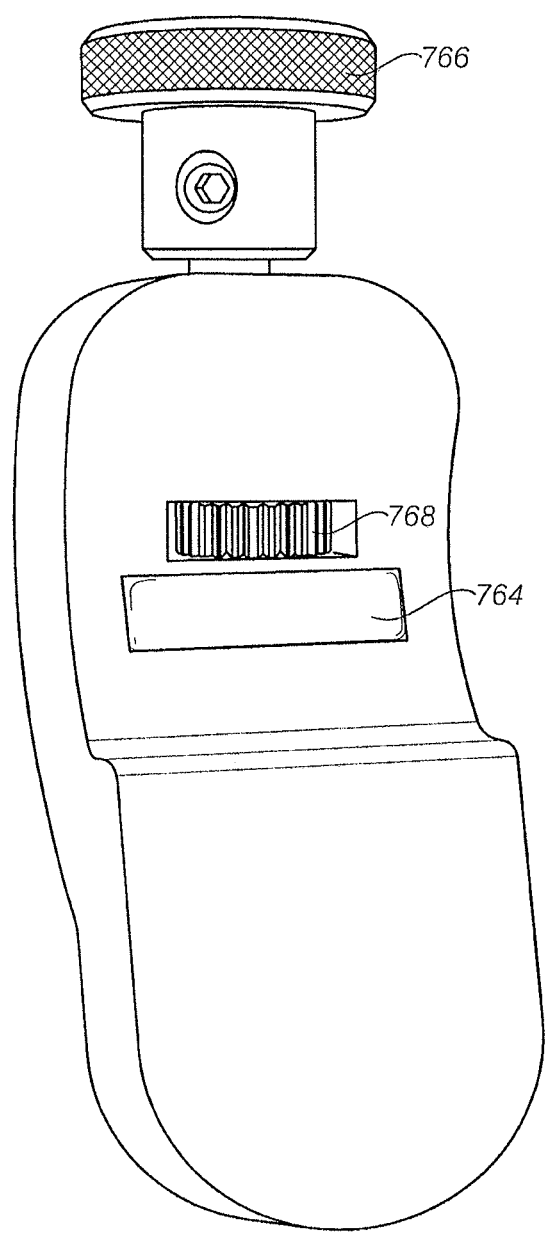
FIG. 21B shows a bottom view of the grasper of FIG. 21A.
Figure 22:
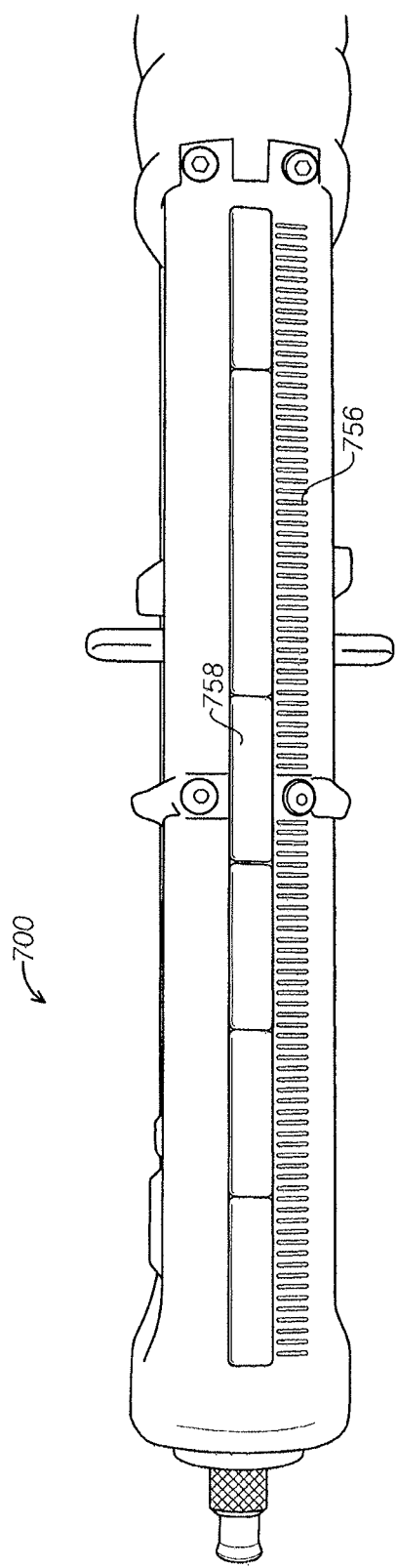
FIG. 22 shows a side view of a handle of a delivery device for mating attachment to a grasper.

For example, a grasper 760 is shown in FIGS. 11A, 21A, and 21B. The grasper 760 includes a grasper coupling aperture 762, a grasper magnet 764, and a grasper adjustment knob 766 mechanically coupled to a grasper coupling wheel 768. The grasper 760 generally has an oblong shape. On one end, the grasper 760 includes the grasper coupling aperture 762 and on the opposing end is the grasper adjustment knob 766 coupled to the grasper coupling wheel 768. The grasper magnet 764 is on the bottom surface adjacent to the grasper coupling wheel 768. The grasper coupling wheel 768 is situated in an opening where it is raised above the surface of the grasper. As can be seen from FIG. 22, the delivery device 700 can include a device magnetic strip 758 disposed on one side of the device. The device magnetic strip 758 may be a single rectangular magnet or a series of individual magnets. In use, the grasper magnets 764 are able to couple to the device magnet strip 758. The device 700 further includes a rail 756 including a series of tracks adjacent to the device magnet strip 758 is. The rail 756 is configured to couple to the grasper coupling wheel 768 such that when the operator rotates the grasper adjustment knob 766, the teeth of the grasper coupling wheel 768 travel proximally and distally along the device tracks 756, thereby allowing controlled relative movement between the grasper and the device. The grasper coupling aperture 762 in this current example is a threaded connection that couples the grasper 760 to a standard VBM arm for supporting and adjusting the delivery device 700. When the grasper 760 is coupled to both the delivery device 700 and a support arm (such as a VBM arm), the operator may adjust the depth of the delivery device distal end 104 within the patient's heart cavity by simply adjusting the grasper adjust knob 766.

Figure 42A:
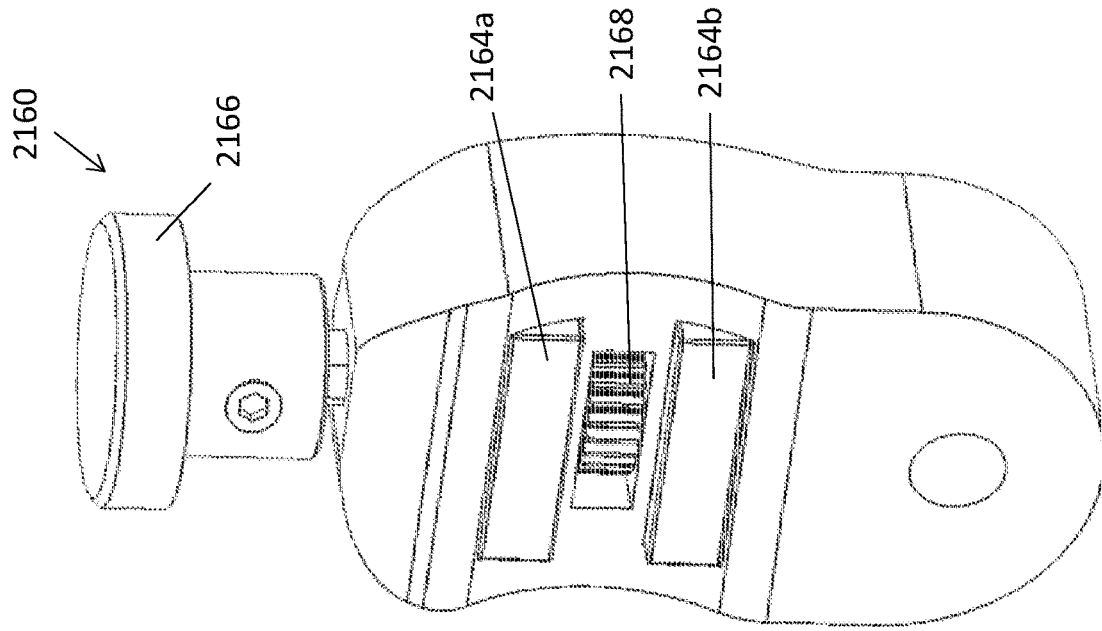
FIGS. 42A-42B show an exemplary grasper for a delivery device.
Figure 42B:
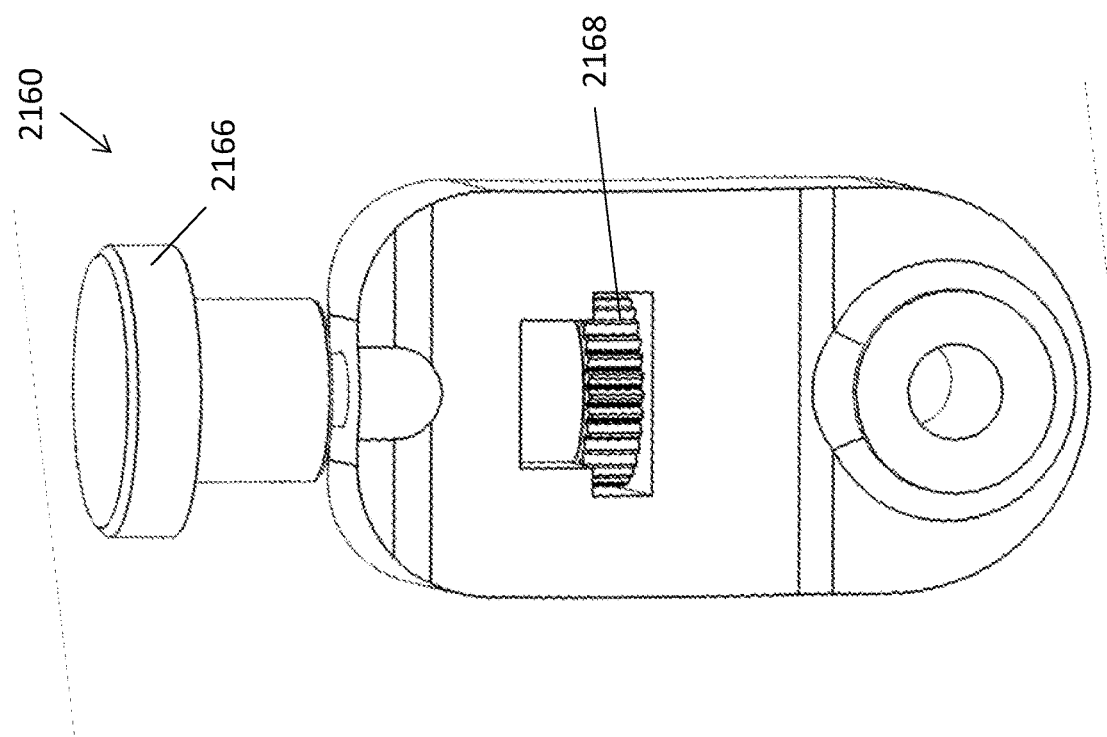

Another exemplary grasper 2160 is shown in FIGS. 42A-42B. The grasper 2160 is similar to grasper 760, but includes two grasper magnets 2164a,b that are configure to sandwich around a rail on the delivery device, such as the rail 5956 shown in FIG. 59B, which sits proud from the magnetic strip 5958. The grasper 2160 further includes a grasper coupling wheel 2168 including teeth that are configured to engage with the teeth of the rail 5956. As such, when the grasper adjustment knob 2166 is rotated by the user, the wheel 2168 will also rotate, causing the rail 5956, and thus the delivery device 5900, to move incrementally.

Any of the embodiments configured to deliver the proximal end first can include any of the features described above with respect to embodiments designed to deliver the distal end first and vice versa.

For any of the delivery devices described herein, certain portions of the delivery device may be composed of transparent or see-through material. This may aid the operator with visualizing what is occurring to the tether lengths and/or prosthetic valve while held within the inner and/or outer sheath.

Figure 27A:
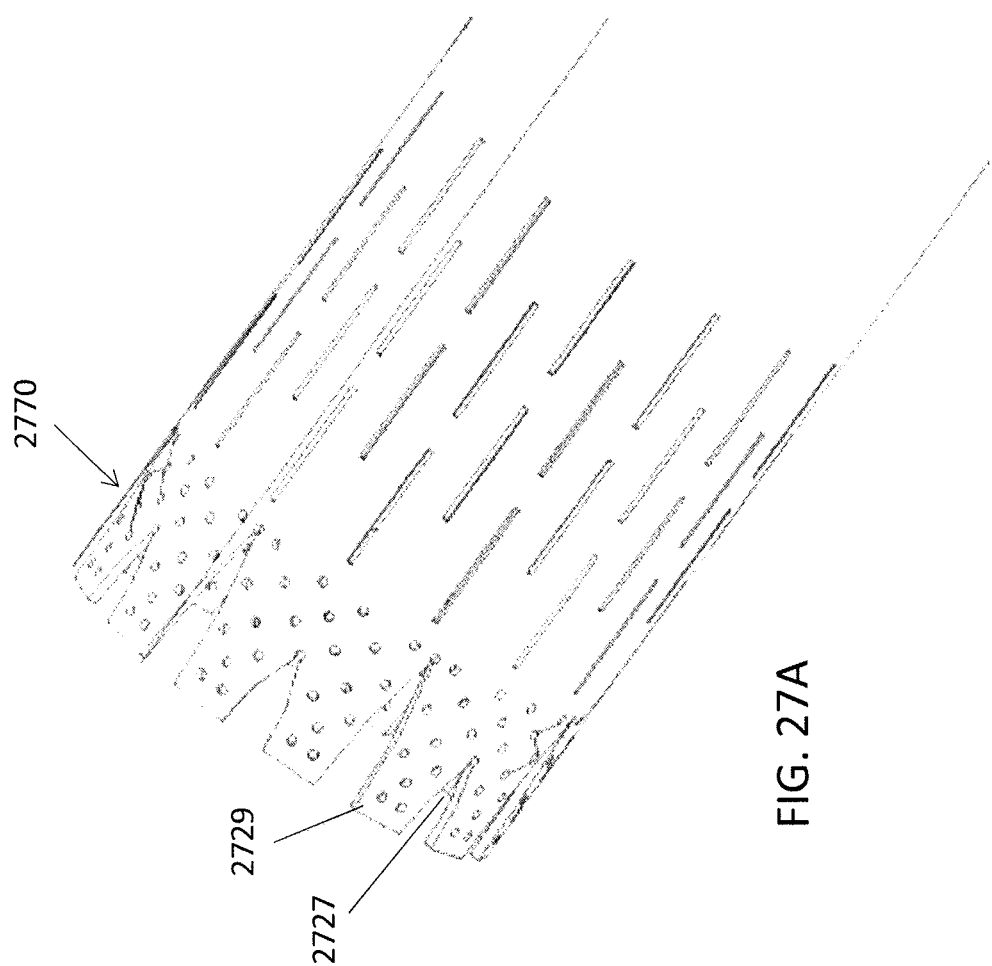
FIG. 27A shows the distal section of a shaft of a delivery device including a plurality of notches.
Figure 27B:
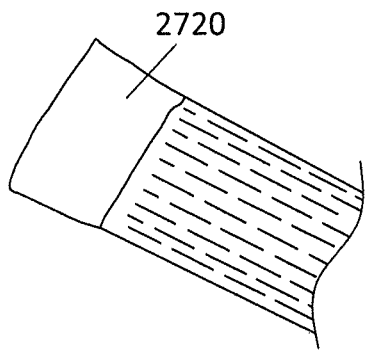
FIGS. 27B-27G show exemplary loading of a valve into the distal section of the shaft shown in FIG. 27A.
Figure 27C:
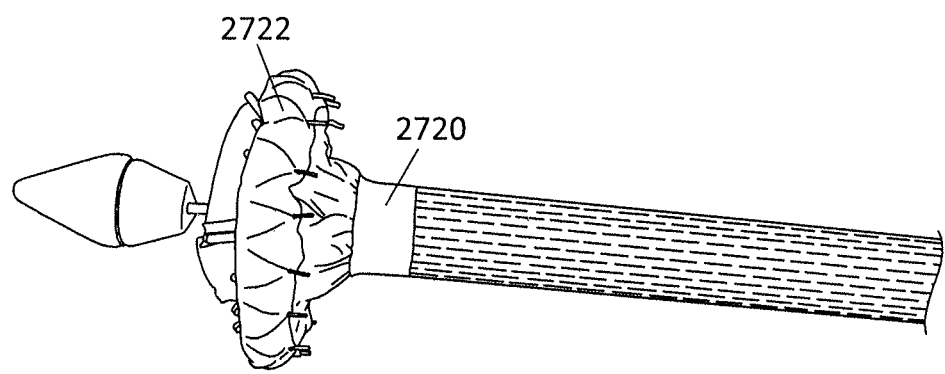
Figure 27D:
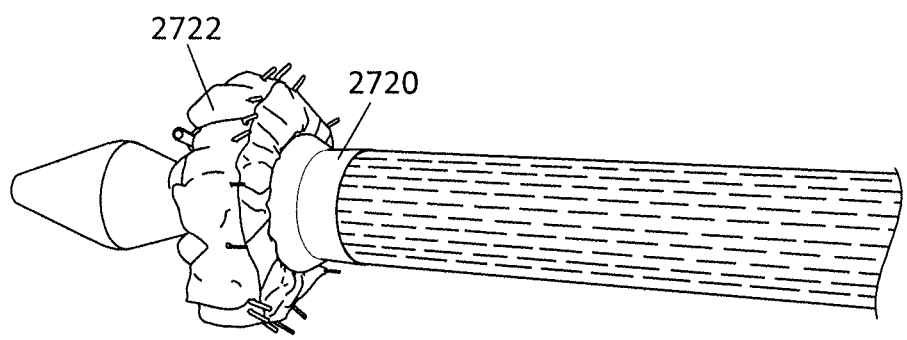
Figure 27E:
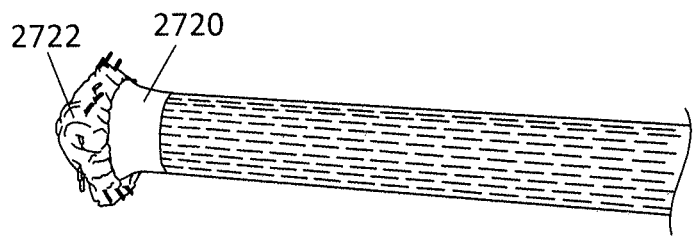
Figure 27F:
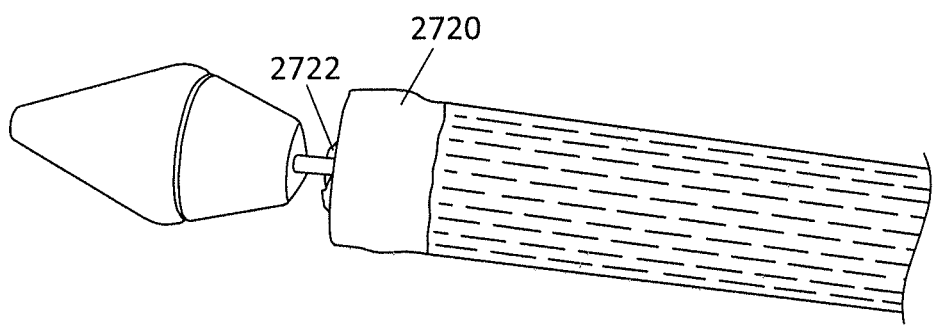
Figure 27G:
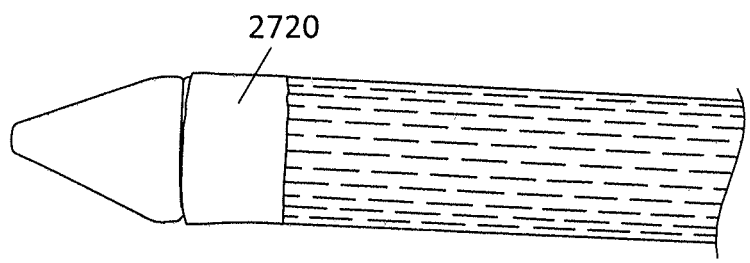
Figure 28B:
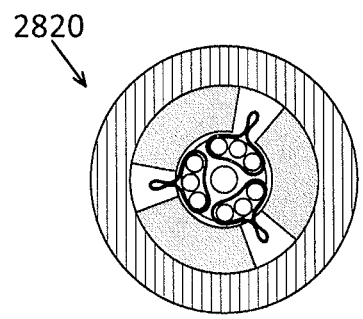
FIG. 28B is a cross-section through the tether retainer of FIG. 28A.
Figure 28A:
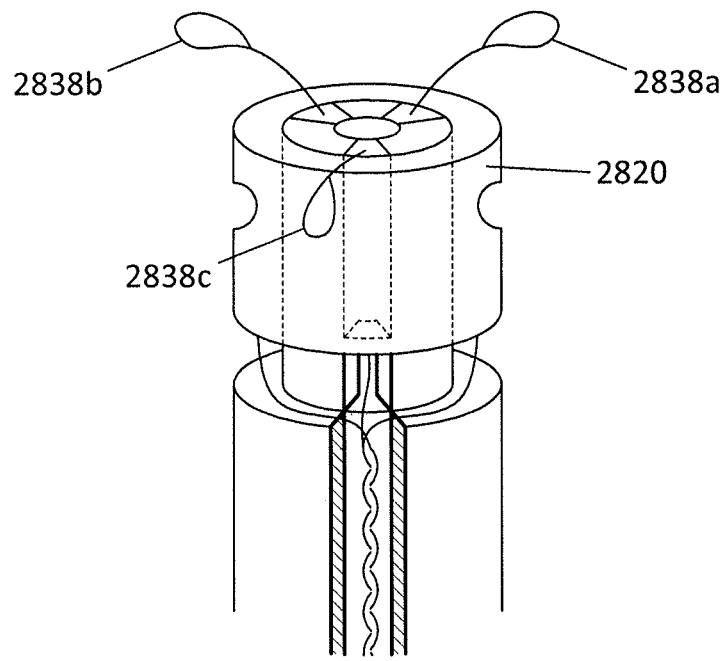
FIG. 28A shows an exemplary delivery system including a tether retrieval mechanism.
Figure 28C:
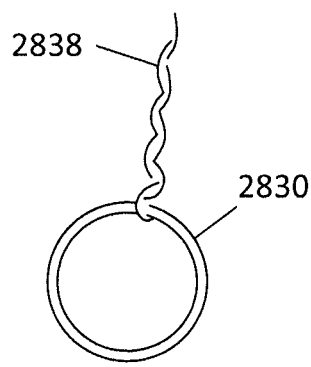
FIG. 28C shows a close-up of the proximal end of a lasso of the delivery device of FIG. 28A.
Figure 28I:
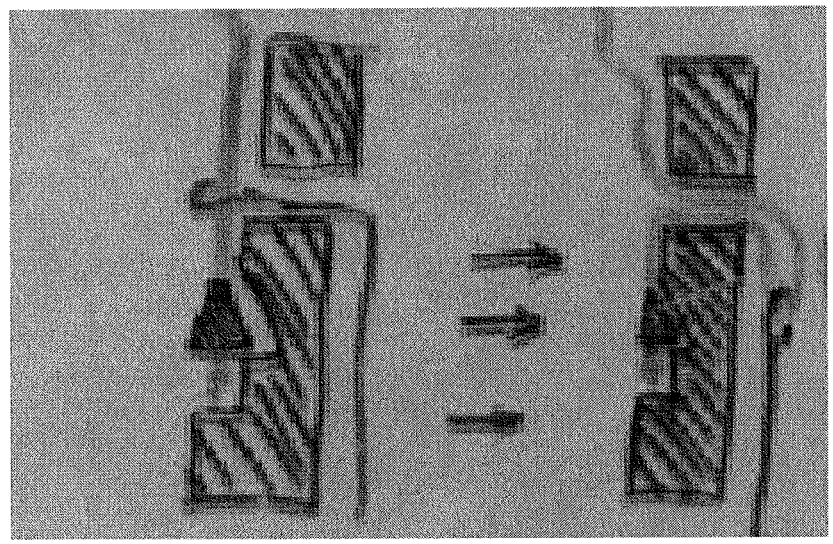
FIG. 28I shows use of a lasso of the delivery device of FIG. 28A to capture/remove a tether.

Any of the delivery devices described herein can include a feature configured to help with retrieving the valve. For example, referring to FIG. 27A, the distal section 2770 of the shaft of the delivery device can include a plurality of notches 2727 and tabs 2729 around the circumference thereof. The tabs 2729 can become narrower and more flexible as they extend towards the distal end. As a result, the notches 2727 and tabs 2929 can enable the distal section 2770 to expand outward like a funnel when an outward radial force is applied thereon, thereby allowing a valve to pull back into the device. In some embodiments, the tabs or notches can be covered with a jacket or thin layer of material to make entry of the valve into the distal section 2770 smooth. An exemplary method of loading a valve into the distal section 2770 (causing flaring of the distal section 2770) is shown in FIGS. 27B-G.

In some embodiments, the delivery devices described herein can include strong cables or wires to hold the valve in a collapsed position rather than using suture-type tethers.

Figure 30A:
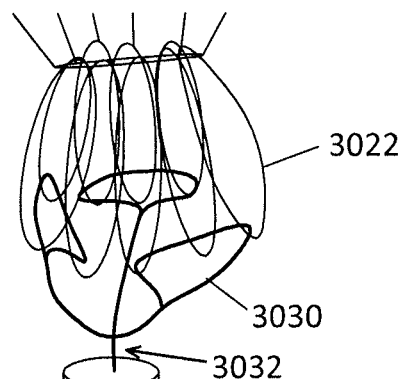
FIGS. 30A-30D show various cables or wire mechanisms that can be part of a delivery device and looped through a valve to hold the valve in the retracted position.
Figure 30B:
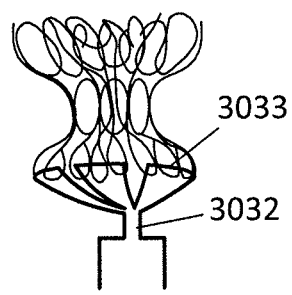
Figure 30C:
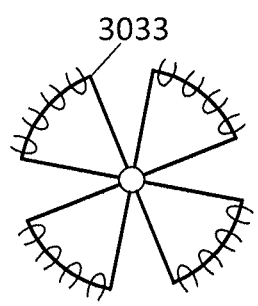
Figure 30D:
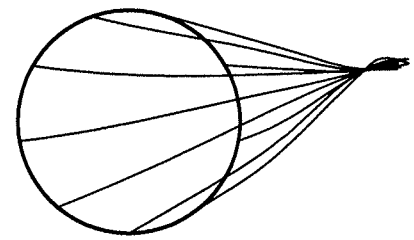

In one example, referring to FIG. 30A, one or more coils 3030 (e.g., of cable, wire, or strong suture) can be looped through a valve 3000 to hold the valve in the retracted position. The coil 3030 can be attached to the rest of the delivery device at a releasable connection point 3032. FIGS. 30B-D show a similar mechanism that includes pie-shaped features 3033 (e.g., of cable or wire) looped through the valve and connected to the delivery device at a releasable connection point 3032.

Figure 31A:
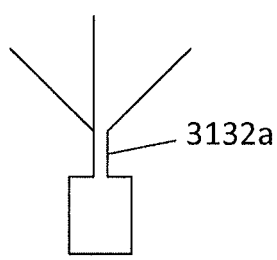
FIGS. 31A-31E show exemplary release mechanisms for cable or wire configurations such as those shown in FIGS. 30A-30D.
Figure 31B:
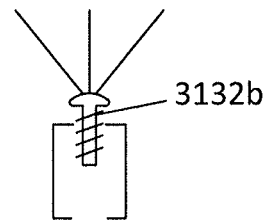
Figure 31C:
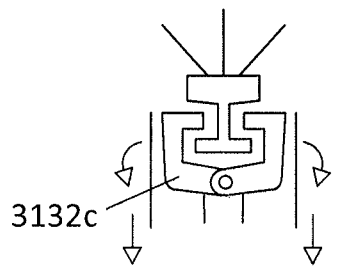
Figure 31D:
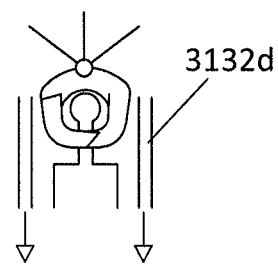
Figure 31E:
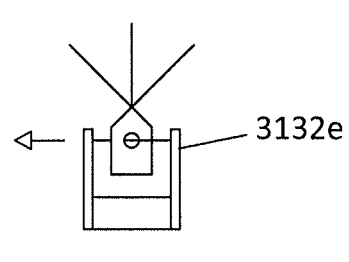

FIGS. 31A-31E show exemplary release mechanism for cables (e.g., strong sutures) or wires such as those shown in FIGS. 30A-30C. For example, FIG. 31A shows a releasable connection point 3132a that can be dissolved by electrolytic dissolution. FIG. 31B shows a releasable connection point 3132b that is released by twisting. FIGS. 31C and 31D show releasable connection points 3132c, 3132d that include releasable jaw clamps. FIG. 31E shows a releasable connection point 3132f that includes a pin that slides out for release.

Figure 32A:
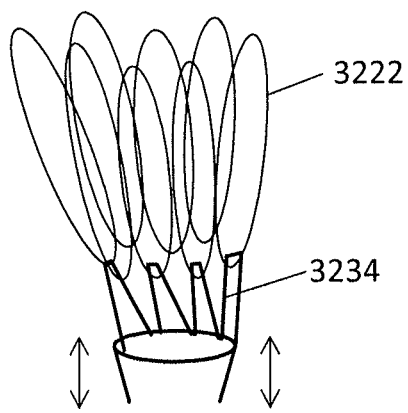
FIGS. 32A-32B show additional cable or wire mechanisms that can be part of a delivery device and looped through a valve to hold the valve in the retracted position.
Figure 32B:
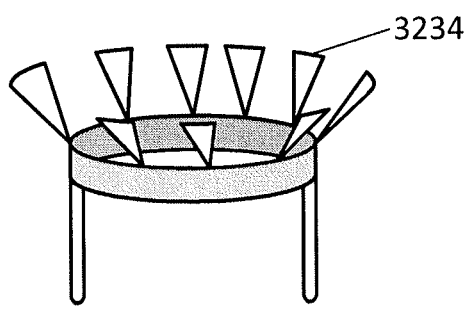
Figure 33A:
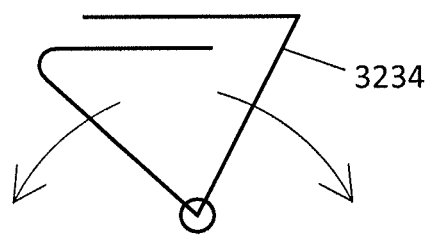
FIGS. 33A-33C show release mechanisms for cable or wire mechanisms such as those shown in FIGS. 32A-32B.
Figure 33B:
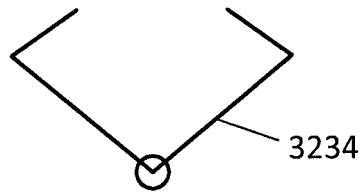
Figure 33C:
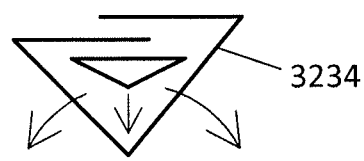
Figure 33D:
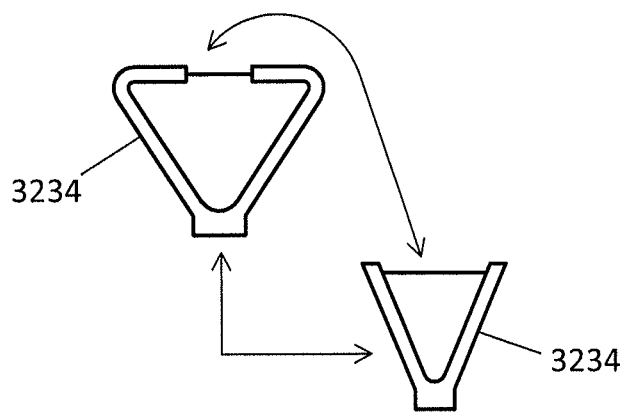
FIG. 33D shows dissolution of a cable or wire mechanism such as those shown in FIGS. 32A-32B.
Figure 34A:
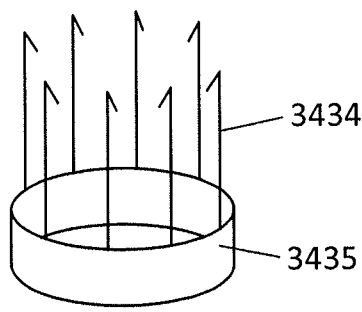
FIG. 34A-34C show another cable or wire mechanism that can be part of a delivery device and looped through a valve to hold the valve in the retracted position.
Figure 34C:
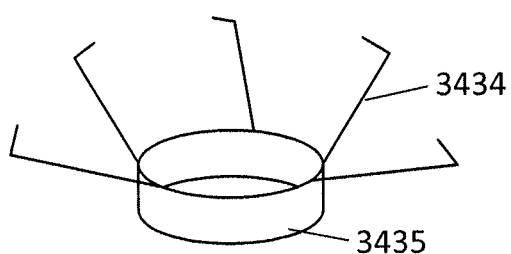
Figure 34B:
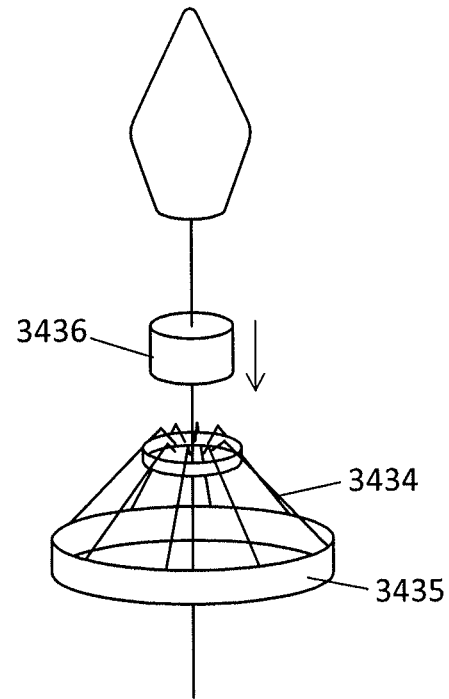

FIGS. 32A-32B show another cable (e.g., strong suture) or wire mechanism that can be configured to be looped through the valve for collapse. The mechanism includes a plurality of rings or clips 3234, each of which clips over one or more portions of a collapsed valve. As shown in FIGS. 33A-33C, the clips can be released by pulling two overlapping portions away. In another embodiment, as shown in FIG. 33D, the clips can have a portion that dissolves through electrolytic dissolution to allow release. FIGS. 34A-34C show another cable or wire mechanism that can be configured to be looped through the valve for collapse. The mechanism includes a plurality of hooks 3434 that extend from a proximal ring 3435 and lock together at a distal end.

Figure 35:
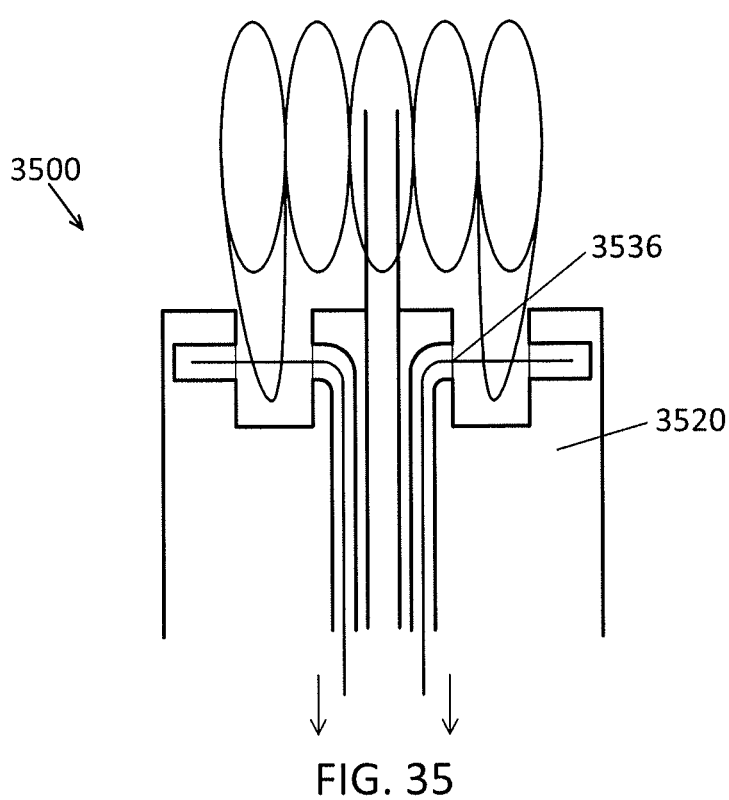
FIG. 35 shows an exemplary delivery device including a plurality of retractable cables or wires.

FIG. 35 shows another mechanism whereby a cable (e.g., strong suture) or wire mechanism can be configured to be looped through the valve. In this embodiment, the delivery device includes a plurality of retractable cables or wires 3536 that extend centrally through the device and curve at the distal end to be housed in the radially outermost portion of a suture retainer 3520. The suture retainer 3520 further includes a plurality of pockets at distal end thereof. The pockets are configured to house loops of the valve, which are held within the pocket by the retractable cables or wires 3536.

Figures 41A, 41B:
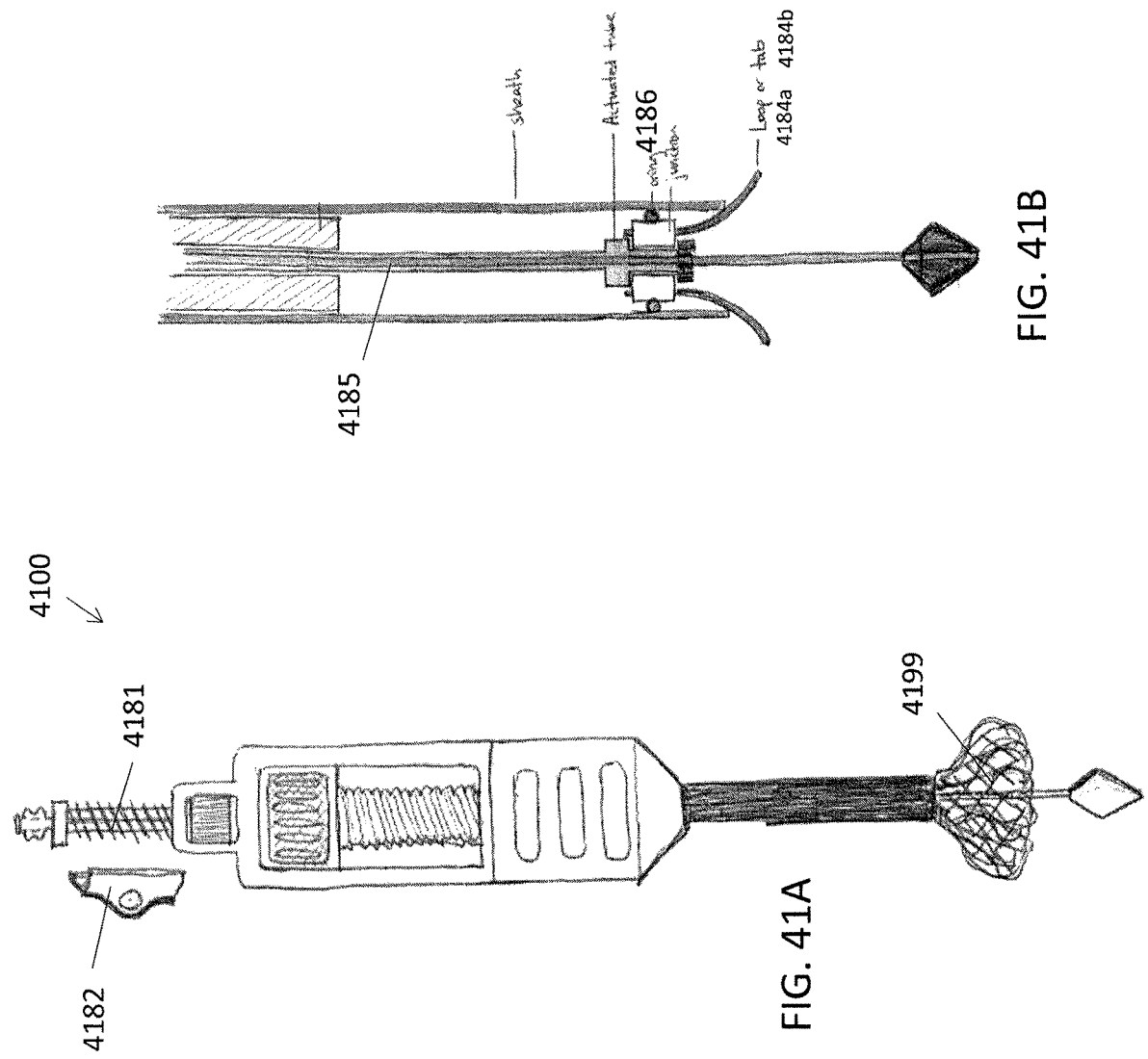
FIGS. 41A-41F show a delivery system including a cable or wire mechanism configured to loop through the valve.
Figure 41F:
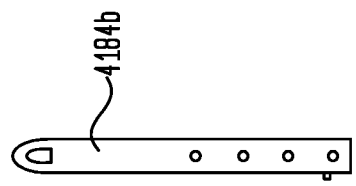
Figure 41D:
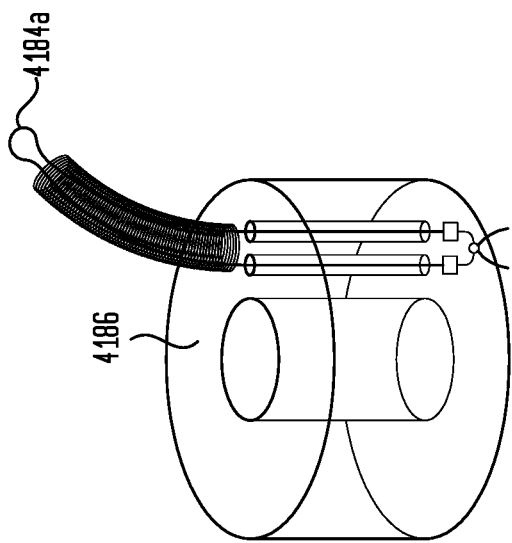
Figure 41E:
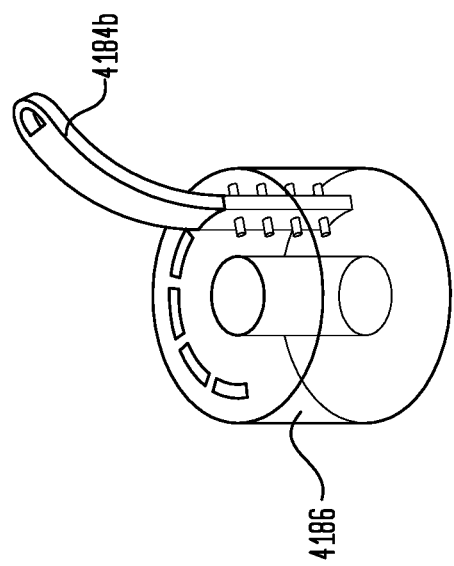
Figure 41C:
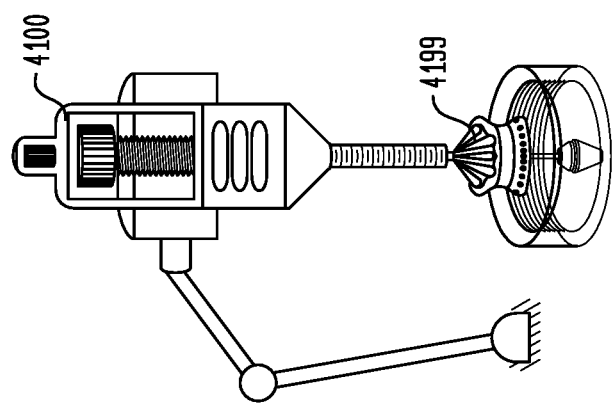

FIGS. 41A-41F show a delivery system 4100 including another retention mechanism whereby a cable (e.g., strong suture) or wire mechanism can be configured to loop through the valve. The system can include, for example, a telescoping threaded rod 4181 configured to activate the retention mechanism. A clip 4182 can hold the rod 4181 in place to prevent undesired movement. Further, the cable or mires can be loops or tabs 4184a,b, respectively, that are connected to a cylindrical member 4186 and actuated proximally and distally by a central shaft 4185. As shown in FIG. 41C, to load the device 4100, a grasper can be used to hold the device steady while loops 4184a or tabs 4184b are loaded through the valve 4199.

In some embodiments, the delivery devices described herein can be made of stainless steel. Stainless steel can advantageously be strong enough to avoid scratching by portions of the valve. Moreover, in some embodiments, an interior layer can be deposited on the outer sheath(s), i.e., the sheaths that house the valve. The interior layer can be, for example, a plasma vapor deposited carbon coating that increases hardness and reduces the coefficient of friction of the interior of the sheath. In some embodiments, the delivery devices described herein can be made of titanium (e.g., 6-4 titanium), which can be strong enough to avoid scratching and minimizes the risk of galvanic corrosion.

Aspects of the delivery devices and methods may be combined with aspects of the delivery devices and methods described in U.S. patent application Ser. No. 14/677,320, U.S. Pat. No. 8,870,948, or International Patent Application filed May 13, 2016 and titled "REPLACEMENT MITRAL VALVES," the entirety of which is incorporated by reference herein.

Although certain embodiments have been described herein as being used for a surgical (cardiopulmonary bypass) route and certain embodiments for a transatrial route, it should be understood that features of any embodiment can be combined with features of any other embodiment.

Further, although described as being used with the transatrial or surgical delivery methods, in some embodiments, the delivery devices described herein can be used to deliver the mitral valve prosthesis through the transseptal route, i.e., through the venous system and into the left atrium via a transseptal puncture.

Although described herein for use with a mitral valve prosthetic, the delivery systems described herein can be used with a variety of different implantable devices, including stents or other valve prosthetics.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A delivery device comprising:
   a handle;
   a central elongate member extending from the handle;
   a sheath configured to slide over and relative to the central elongate member;
   a distal tether retainer at a distal end of the central elongate member;
   a proximal tether retainer positioned along the central elongate member distal of the handle and proximal of the distal tether retainer, the proximal tether retainer including a mini clamp positioned within the sheath; and
   a plurality of tethers configured to extend from the proximal tether retainer to the distal tether retainer.

2. The delivery device of claim 1, wherein the proximal tether retainer is between 1 and 3 inches away from the distal tether retainer.

3. The delivery device of claim 1, wherein the mini clamp includes a set of washers around which proximal ends of the plurality of tethers are wound.

4. The delivery device of claim 3, further comprising a screw and nut within the sheath and sandwiching the washers, the nut configured to rotate relative to the screw to allow the washers to pull apart and release the proximal ends of the tethers.

5. The delivery device of claim 1, wherein the proximal tether retainer is configured to move axially to tighten or loosen the tethers.

6. The delivery device of claim 5, wherein the handle further comprises a tether control configured to axially move the proximal tether retainer.

7. The delivery device of claim 6, wherein the tether control is a knob.

8. The delivery device of claim 7, wherein the knob is configured to move axially from a proximal position to a distal position, the proximal position providing free spinning of the knob and the distal position providing ratcheting of the knob.

9. The delivery device of claim 7, wherein the knob in the proximal position is configured to rotate in both a first direction and a second direction to provide tightening and loosening of the plurality of tethers.

10. The delivery device of claim 9, wherein the knob in the distal position is configured to rotate only in the first direction to provide tightening of the plurality of tethers but not loosening of the plurality of tethers.

11. The delivery device of claim 1, further comprising a sheath control knob on the handle, the sheath control knob being rotatable to slide the sheath axially relative to the central elongate member.

12. The delivery device of claim 1, wherein the distal tether retainer includes a plurality of pockets.

13. The delivery device of claim 12, wherein the plurality of tethers each include a feature on the distal end thereof configured to fit within a pocket of the plurality of pockets to hold the distal end in place.

* * * * *